United States Patent
Chiang et al.

(10) Patent No.: US 6,545,018 B2
(45) Date of Patent: Apr. 8, 2003

(54) OXAMIC ACIDS AND DERIVATIVES AS THYROID RECEPTOR LIGANDS

(75) Inventors: Yuan-Ching Phoebe Chiang, East Lyme, CT (US); Robert L. Dow, Waterford, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/966,467

(22) Filed: Sep. 27, 2001

(65) Prior Publication Data

US 2002/0049226 A1 Apr. 25, 2002

Related U.S. Application Data

(62) Division of application No. 09/514,862, filed on Feb. 28, 2000, now Pat. No. 6,326,398.
(60) Provisional application No. 60/122,292, filed on Mar. 1, 1999.

(51) Int. Cl.[7] ..................... C07D 213/02; C07C 233/56; C07C 69/76; A61K 31/44
(52) U.S. Cl. .................. 514/307; 514/352; 514/535; 514/563; 514/617; 546/152; 546/336; 560/19; 560/143; 562/433; 564/155
(58) Field of Search .................. 514/535, 563, 514/617, 307, 352; 564/155; 562/433; 560/19, 143; 546/152, 336

(56) References Cited

U.S. PATENT DOCUMENTS

| | | | |
|---|---|---|---|
| 4,069,343 A | 1/1978 | Sellstedt et al. | 424/319 |
| 4,554,290 A | 11/1985 | Boger et al. | 514/487 |
| 4,766,121 A | 8/1988 | Ellis et al. | 514/247 |
| 4,826,876 A | 5/1989 | Ellis et al. | 514/535 |
| 4,910,305 A | 3/1990 | Ellis et al. | 544/239 |
| 5,061,798 A | 10/1991 | Emmett et al. | 544/239 |
| 5,232,947 A | 8/1993 | Sato et al. | 514/549 |
| 5,284,971 A | 2/1994 | Walker et al. | 562/429 |
| 5,401,772 A | 3/1995 | Yokoyama et al. | 514/539 |
| 5,569,674 A | 10/1996 | Yokoyama et al. | 514/539 |
| 5,654,468 A | 8/1997 | Yokoyama et al. | 560/43 |
| 6,326,398 B1 * | 12/2001 | Chiang et al. | 514/535 |

FOREIGN PATENT DOCUMENTS

| | | | |
|---|---|---|---|
| EP | 0580550 | 1/1994 | C07C/233/56 |
| WO | WO0007972 | 2/2000 | C07C/59/135 |
| WO | WO0058279 | 10/2000 | C07C/311/29 |

OTHER PUBLICATIONS

Chan et al., "New–N– and )O –Arylations with Phenylboronic Acids and Cupric Acetate", Tetrahedron Letters 39:2933–2936 (1998).

Steele et al., CSG 26214, "The Thyroxine Connection Revisited", Atherosclerosis X 321–324 (1995).

Stephan, et al., "Demonstration of Potent Lipid–Lowering Activity By Athyromimetic Agent Devoid of Cardiovascular and Thermogenic Agents", Atherosclerosis 126: 53–63 (1996).

Underwood, et al., "A Thyromimetic that Decreases Plasma Cholesterol Levels Without Increasing Cardiac Acitivty", Nature 324:425–429 (1986).

Yokoyama, N. et al., "Synthesis and Structure—Activity Relationships of Oxamic Acid and Acetic Acid Derivatives Related to L–Thyronine", J. Med. Chem 38 (4) 695–707 (1995).

Taylor A.H. et al., "Beneficial Effects of a Novel Thyromometic on Lipoprotein Metabolism", Molecular Pharmacology, 52: 542–547 (1997).

Stanton, J. L. et al., "Synthesis and Biological Activity of Phenoxyphenyl Oxamic Related to L–Thyronine", Bioorganic & Medicinal Chemistry Letters, 10: 1661–1663 (2000).

* cited by examiner

Primary Examiner—Zinna Northington Davis
(74) Attorney, Agent, or Firm—Peter C. Richardson; Gregg C. Benson; Martha A. Gammill

(57) ABSTRACT

The present invention provides novel compounds of the Formula

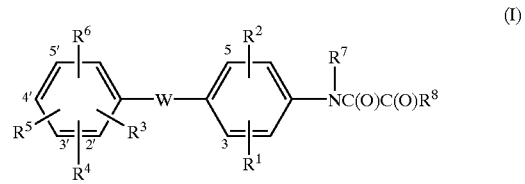

(I)

and prodrugs thereof, geometric and optical isomers thereof, and pharmaceutically acceptable salts of such compounds, prodrugs and isomers, wherein $R^1$–$R^8$ and W are as described herein. Pharmaceutical compositions containing such compounds, prodrugs, isomers or pharmaceutically acceptable salts thereof, and methods, pharmaceutical compositions and kits for treating obesity, hyperlipidemia, glaucoma, cardiac arrhythmia, skin disorders, thyroid disease, hypothyroidism and related disorders and diseases such as diabetes mellitus, atherosclerosis, hypertension, coronary heart disease, hypercholesteremia, depression and osteoporosis are also provided.

129 Claims, No Drawings

OXAMIC ACIDS AND DERIVATIVES AS THYROID RECEPTOR LIGANDS

CROSS-REFERENCE TO RELATED APPLICATION

This application is a divisional of U.S. patent application Ser. No. 09/514,862, filing date Feb. 28, 2000 now U.S. Pat. No. 6,326,398, which claims priority of U.S. provisional patent application No. 60/122,292, filed Mar. 1, 1999.

FIELD OF THE INVENTION

The present invention relates to novel thyroid receptor ligands and, more particularly, relates to novel oxamic acids, and derivatives thereof, which are useful in the treatment of obesity, hyperlipidemia, glaucoma, cardiac arrhythmia, skin disorders, thyroid disease, hypothyroidism and related disorders and diseases such as diabetes mellitus, atherosclerosis, hypertension, coronary heart disease, hypercholesteremia, depression and osteoporosis. Also provided are methods, pharmaceutical compositions and kits for treating such diseases and disorders.

BACKGROUND OF THE INVENTION

It is generally accepted that thyroid hormones, specifically, biologically active iodothyronines, are critical to normal development and to maintaining metabolic homeostasis. Thyroid hormones stimulate the metabolism of cholesterol to bile acids and enhance the lipolytic responses of fat cells to other hormones.

Thyroid hormones also affect cardiac function both directly and indirectly, e.g., by increasing the metabolic rate. For example, tachycardia, increased stroke volume, increased cardiac index, cardiac hypertrophy, decreased peripheral vascular resistance and increased pulse pressure are observed in patients with hyperthyroidism.

Disorders of the thyroid are generally treated with hormone replacement by administering either naturally occurring thyroid hormones or thyromimetic analogues thereof which mimic the effects of thyroid hormones.

Two naturally occurring thyroid hormones, namely, thyroxine or 3,5,3',5'-tetraiodo-L-thyronine (commonly referred to as "$T_4$") and 3,5,3'-triiodo-L-thyronine (commonly referred to as "$T_3$"), are shown below:

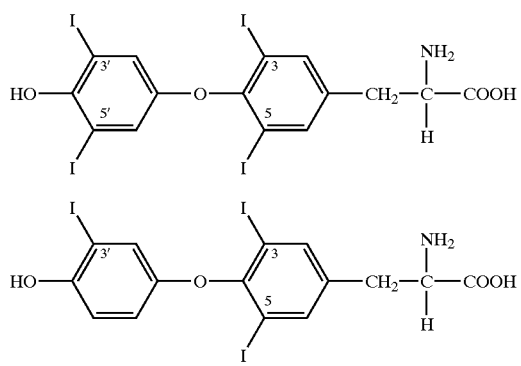

$T_3$ is the more biologically active of the two and, as will be appreciated from the structural formulae provided above, differs from $T_4$ by the absence of the 5' iodine.

$T_3$ may be produced directly from the thyroid gland, or, in peripheral tissues, by the removal of the 5' iodine by deiodinase enzymes. Thyromimetic analogs are often designed to be structurally similar to $T_3$. In addition, naturally occurring metabolites of $T_3$ are known.

As discussed above, thyroid hormones affect cardiac functioning, for example, by causing an increase in the heart rate and, accordingly, an increase in oxygen consumption. While the increase in oxygen consumption may result in certain desired metabolic effects, nonetheless, it does place an extra burden on the heart, which in some situations, may give rise to damaging side effects. Therefore, as is known in the art, such as described by A. H. Underwood et al. in an article published in *Nature,* Vol. 324: pp. 425–429 (1986), efforts have been made to synthesize thyroid hormone analogs which function to lower lipids and serum cholesterol without generating the adverse cardiac effects referred to above.

U.S. Pat. Nos. 4,766,121; 4,826,876; 4,910,305; and 5,061,798 disclose certain thyroid hormone mimetics, namely, 3,5-dibromo-3'-[6-oxo-3(1H)-pyridazinylmethyl]-thyronines.

U.S. Pat. No. 5,284,971 discloses certain thyromimetic cholesterol lowering agents, namely, 4-(3-cyclohexyl-4-hydroxy or -methoxy phenylsulfonyl)-3,5 dibromophenylacetic compounds.

U.S. Pat. Nos. 5,401,772; 5,654,468; and 5,569,674 disclose certain lipid lowering agents, namely, heteroacetic acid derivatives, which compete with radiolabeled $T_3$ in binding assays using rat liver nuclei and plasma membrane preparations.

Certain oxamic acids and derivatives thereof are known in the art, e.g., U.S. Pat. No. 4,069,343 describes the use of certain oxamic acids to prevent immediate type hypersensitivity reactions; U.S. Pat. No. 4,554,290 describes the use of certain oxamic acids to control pests on animals and plants; U.S. Pat. No. 5,401,772 discloses certain oxamic acids as lipid lowering agents; U.S. Pat. No. 5,232,947 describes the use of certain oxamic acids to improve damaged cerebral functions of the brain; and European Pat. Specification published as EP 580,550 discloses certain oxamic acid derivatives as hypocholesteremic agents.

In addition, certain oxamic acid derivatives of thyroid hormones are known in the art. For example, N. Yokoyama et al. in an article published in the *Journal of Medicinal Chemistry,* 38 (4): 695–707 (1995) describe replacing a —$CH_2$ group in a naturally occurring metabolite of $T_3$ with an —NH group resulting in —$HNCOCO_2H$. Likewise, R. E. Steele et al. in an article published in International Congressional Service (*Atherosclerosis* X) 1066: 321–324 (1995) and Z. F. Stephan et al. in an article published in *Atherosclerosis,* 126: 53–63 (1996), describe certain oxamic acid derivatives useful as lipid-lowering thyromimetic agents yet devoid of undesirable cardiac activities.

All of the documents cited herein, including the foregoing, are incorporated by reference herein in their entireties.

SUMMARY OF THE INVENTION

The present invention provides compounds of Formula I:

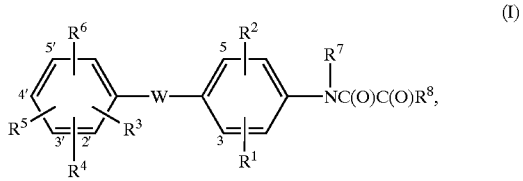

prodrugs thereof, geometric and optical isomers thereof, and pharmaceutically acceptable salts of said compounds, said prodrugs, and said isomers, wherein:

$R^1$, $R^2$ and $R^3$ are each independently hydrogen, halogen, $C_{1-6}$ alkyl, trifluoromethyl, —CN, —$OCF_3$ or —$OC_{1-6}$ alkyl;

$R^4$ is hydrogen, $C_{1-12}$ alkyl optionally substituted with one to three substituents independently selected from Group Z, $C_{2-12}$ alkenyl, halogen, —CN, aryl, heteroaryl, $C_{3-10}$ cycloalkyl, heterocycloalkyl, —$S(O)_2NR^9R^{10}$, —$C(O)NR^9R^{10}$, —($C_{1-6}$ alkyl)-$NR^9R^{10}$, —$NR^9C(O)R^{10}$, —$NR^9C(O)NR^9R^{10}$, —$NR^9S(O)_2R^{10}$, —($C_{1-6}$alkyl)-$OR^{11}$, —$OR^{11}$ or —$S(O)_aR^{12}$, provided that, where $R^5$ is not fluoro, $R^4$ is —$S(O)_2NR^9R^{10}$, $C(O)NR^9R^{10}$, —($C_{1-6}$ alkyl)-$NR^9R^{10}$, —$NR^9C(O)R^{10}$, —$NR^9C(O)NR^9R^{10}$, —$NR^9S(O)_2R^{10}$, —($C_{1-6}$ alkyl)-$OR^{11}$, —$OR^{11}$ or —$S(O)_aR^{12}$;

or $R^3$ and $R^4$ may be taken together to form a carbocyclic ring A of the formula —$(CH_2)_b$— or a heterocyclic ring A selected from the group consisting of —Q—$(CH_2)_c$— and —$(CH_2)_j$—Q—$(CH_2)_k$— wherein Q is O, S or $NR^{17}$, wherein said carbocyclic ring A and said heterocyclic ring A are each independently optionally substituted with one or more substituents independently selected from $C_{1-4}$ alkyl, halide or oxo;

$R^5$ is fluoro, hydroxy, $C_{1-4}$ alkoxy or $OC(O)R^9$;

or $R^4$ and $R^5$ may be taken together to form a heterocyclic ring B selected from the group consisting of —$CR^9$=$CR^{10}$—NH—, —N=$CR^9$—NH—, —$CR^9$=CH—O— and —$CR^9$=CH—S—;

$R^6$ is hydrogen, halogen, $C_{1-4}$ alkyl or trifluoromethyl;

$R^7$ is hydrogen or $C_{1-6}$ alkyl;

$R^8$ is —$OR^9$ or —$NR^{19}R^{20}$;

$R^9$ and $R^{10}$ for each occurrence are independently (A) hydrogen, (B) $C_{1-12}$ alkyl optionally substituted with one or more substituents independently selected from Group V, (C) $C_{2-12}$ alkenyl, (D) $C_{3-10}$ cycloalkyl optionally substituted with one or more substituents independently selected from $C_{1-6}$ alkyl, $C_{2-5}$ alkynyl, $C_{3-10}$ cycloalkyl, —CN, —$NR^{13}R^{14}$, oxo, —$OR^{18}$, —$COOR^{18}$ or aryl optionally substituted with X and Y, (E) aryl optionally substituted with X and Y, or (F) het optionally substituted with X and Y;

or $R^9$ and $R^{10}$ for any occurrence may be taken together to form a heterocyclic ring C optionally further containing a second hetero group selected from the group consisting of —O—, —$NR^{13}$— and —S—, and optionally further substituted with one or more substituents independently selected from $C_{1-5}$ alkyl, oxo, —$NR^{13}R^{14}$, —$OR^{18}$, —$C(O)_2R^{18}$, —CN, —$C(O)R^9$, aryl optionally substituted with X and Y, het optionally substituted with X and Y, $C_{5-6}$ spirocycloalkyl, and a carbocyclic ring B selected from the group consisting of 5-, 6-, 7- and 8-membered partially and fully saturated, and unsaturated carbocyclic rings, and including any bicyclic group in which said carbocyclic ring B is fused to a carbocyclic ring C selected from the group consisting of 5-, 6-, 7-and 8-membered partially and fully saturated, and unsaturated carbocyclic rings;

$R^{11}$ is $C_{1-12}$ alkyl optionally substituted with one or more substituents independently selected from Group V, $C_{2-12}$ alkenyl, $C_{3-10}$ cycloalkyl, trifluoromethyl, difluoromethyl, monofluoromethyl, aryl optionally substituted with X and Y, het optionally substituted with X and Y, —$C(O)NR^9R^{10}$ or —$C(O)R^9$;

$R^{12}$ is $C_{1-12}$ alkyl optionally substituted with one or more substituents independently selected from Group V, $C_{2-12}$ alkenyl, $C_{3-10}$ cycloalkyl, aryl optionally substituted with X and Y, or het optionally substituted with X and Y;

$R^{13}$ and $R^{14}$ for each occurrence are independently hydrogen, $C_{1-6}$ alkyl, $C_{2-6}$ alkenyl, —($C_{1-6}$ alkyl)-$C_{1-6}$ alkoxy, aryl optionally substituted with X and Y, het optionally substituted with X and Y, —($C_{1-4}$ alkyl)-aryl optionally substituted with X and Y, —($C_{1-4}$ alkyl)-heterocycle optionally substituted with X and Y, —($C_{1-4}$ alkyl)-hydroxy, —($C_{1-4}$ alkyl)-halo, —($C_{1-4}$ alkyl)-poly-halo, —($C_{1-4}$ alkyl)-$CONR^{15}R^{16}$ or $C_{3-10}$ cycloalkyl;

$R^{15}$ and $R^{16}$ for each occurrence are independently hydrogen, $C_{1-6}$ alkyl, $C_{3-10}$ cycloalkyl or aryl optionally substituted with X and Y;

$R^{17}$ is hydrogen, $C_{1-6}$ alkyl, —$COR^9$ or —$SO_2R^9$;

$R^{18}$ is hydrogen, $C_{1-6}$ alkyl, $C_{2-6}$ alkenyl, —($C_{1-6}$ alkyl)-$C_{1-6}$ alkoxy, aryl optionally substituted with X and Y, het optionally substituted with X and Y, —($C_{1-4}$ alkyl)-aryl optionally substituted with X and Y, —($C_{1-4}$ alkyl)-heterocycle optionally substituted with X and Y, —($C_{1-4}$ alkyl)-hydroxy, —($C_{1-4}$ alkyl)-halo, —($C_{1-4}$ alkyl)-poly-halo, —($C_{1-4}$ alkyl)-$CONR^{15}R^{16}$, —($C_{1-4}$ alkyl)-($C_{1-4}$ alkoxy) or $C_{3-10}$ cycloalkyl;

$R^{19}$ is hydrogen or $C_{1-6}$ alkyl;

$R^{20}$ is hydrogen or $C_{1-6}$ alkyl;

W is O, $S(O)_d$, $CH_2$ or $NR^9$;

Group Z is $C_{2-6}$ alkenyl, $C_{2-6}$ alkynyl, halogen, —$CF_3$, —$OCF_3$, hydroxy, oxo, —CN, aryl, heteroaryl, $C_{3-10}$ cycloalkyl, heterocycloalkyl, —$S(O)_aR^{12}$, —$S(O)_2NR^9R^{10}$, —$C(O)R^9R^{10}$, and —$NR^9R^{10}$;

Group V is halogen, —$NR^{13}R^{14}$, —$OCF_3$, —$OR^9$, oxo, trifluoromethyl, —CN, $C_{3-10}$ cycloalkyl, aryl optionally substituted with X and Y, and het optionally substituted with X and Y;

het for each occurrence is a heterocyclic ring D selected from the group consisting of 4-, 5-, 6-, 7- and 8-membered partially and fully saturated, and unsaturated, heterocyclic rings containing from one to four heteroatoms independently selected from the group consisting of N, O and S, and including any bicyclic group in which said heterocyclic ring D is fused to a benzene ring or a heterocyclic ring E selected from the group consisting of 4-, 5-, 6-, 7- and 8-membered partially and fully saturated, and unsaturated, heterocyclic rings containing from one to four heteroatoms independently selected from the group consisting of N, O and S;

X and Y for each occurrence are independently (A) hydrogen, (B) halogen, (C) trifluoromethyl, (D) —$OCF_3$, (E) —CN, (F) $C_{1-6}$ alkyl optionally substituted with one or more substituents independently selected from the group consisting of halogen, —$OCF_3$, —$CF_3$ and phenyl, (G) $C_{1-6}$ alkoxy, (H) aryl optionally substituted with one or more substituents independently selected from the group consisting of halogen, —$OCF_3$, —$CF_3$, $C_{1-4}$ alkyl and $C_{1-4}$ alkoxy, (I) —$C(O)_2R^{13}$, (J) —$C(O)NR^{13}R^{14}$, (K)—$C(O)R^{13}$, (L) —$NR^{13}C(O)NR^{13}R^{14}$ and (M) —$NR^{13}C(O)R^{14}$; or X and Y for any occurrence in the same variable may be taken together to form (a) a carbocyclic ring D of the formula —$(CH_2)_e$— or (b) a heterocyclic ring F selected from the group consisting of —$O(CH_2)_fO$—, $(CH_2)_gNH$— and —CH=CHNH—;

a and d are each independently 0, 1 or 2;

b is 3, 4, 5, 6 or 7;

c, f, g, j and k are each independently 2, 3, 4, 5 or 6; and e is 3, 4, 5, 6 or 7.

A preferred group of compounds and pharmaceutically acceptable salts of such compounds, designated the A Group, contains those compounds of Formula I and pharmaceutically acceptable salts of such compounds, as shown above, wherein W is O.

A preferred group of compounds and pharmaceutically acceptable salts of such compounds, of the A Group, designated the B Group, contains those compounds of Formula I and pharmaceutically acceptable salts of such compounds, as shown above, wherein $R^1$ is located at the 3 position, $R^2$ is located at the 5 position, $R^3$ is located at the 2' position, $R^4$ is located at the 3' position, $R^5$ is located at the 4' position, and $R^6$ is located at the 5' position.

A preferred group of compounds and pharmaceutically acceptable salts of such compounds, of the B Group, designated the C Group, contains those compounds of Formula I and pharmaceutically acceptable salts of such compounds, as shown above, wherein $R^3$ is hydrogen, or $R^3$ and $R^4$ are taken together to form a carbocyclic ring A of the formula —$(CH_2)_b$— or a heterocyclic ring A selected from the group consisting of —Q—$(CH_2)_c$— and —$(CH_2)_j$—Q—$(CH_2)_k$— wherein Q is O, S or $NR^{17}$, wherein said carbocyclic ring A and said heterocyclic ring A are each independently optionally substituted with one or more substituents independently selected from $C_{1-4}$ alkyl, halide or oxo, $R^5$ is hydroxy, $R^6$ is hydrogen and $R^7$ is hydrogen.

A preferred group of compounds pharmaceutically acceptable salts of such compounds, of the C Group, designated the D Group, contains those compounds of Formula I and pharmaceutically acceptable salts of such compounds, as shown above, wherein $R^1$ and $R^2$ are each independently methyl, bromo or chloro, and $R^8$ is hydroxy, methoxy, ethoxy, isopropoxy, $NH_2$ or $NH(CH_3)$.

A preferred group of compounds and pharmaceutically acceptable salts of such compounds, of the D Group, designated the E Group, contains those compounds of Formula I and pharmaceutically acceptable salts of such compounds, as shown above, wherein $R^4$ is $S(O)_2NR^9R^{10}$, and $R^{10}$ is hydrogen or methyl.

Particularly preferred compounds of the E Group are compounds wherein (a) $R^1$ is chloro, $R^2$ is methyl, $R^8$ is ethoxy or hydroxy, $R^9$ is ethyl and $R^{10}$ is hydrogen, (b) $R^1$ is chloro, $R^2$ is methyl, $R^8$ is ethoxy or hydroxy, $R^9$ is n-butyl and $R^{10}$ is hydrogen, (c) $R^1$ is chloro, $R^2$ is methyl, $R^8$ is ethoxy or hydroxy, $R^9$ is —$CH_2$—cyclopropyl and $R^{10}$ is hydrogen and (d) $R^1$ is chloro, $R^2$ is methyl, $R^8$ is isopropoxy or hydroxy, $R^9$ is cyclopropyl and $R^{10}$ is hydrogen; and pharmaceutically acceptable salts of said compounds.

Another preferred group of compounds and pharmaceutically acceptable salts of such compounds, of the D Group, designated the F Group, contains those compounds of Formula I and pharmaceutically acceptable salts of such compounds, as shown above, wherein $R^4$ is $S(O)_2NR^9R^{10}$, and $R^9$ and $R^{10}$ are taken together with the nitrogen atom to which they are attached to form $N(CH_2)_4$, $N(CH_2)_5$, morpholinr or

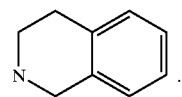

Particularly preferred compounds of the F Group are those wherein $R^9$ and $R^{10}$ are taken together with the nitrogen atom to which they are attached to form $N(CH_2)_4$.

A preferred group of compounds and pharmaceutically acceptable salts of such compounds, of the E Group, designated the G Group, contains those compounds of Formula I and pharmaceutically acceptable salts of such compounds, as shown above, wherein $R^9$ is hydrogen, isopropyl, —$CH_2$-2-thienyl, —$CH_2$-cyclopropyl, cyclopropyl, —$(CH_2)_2OH$, exo-2-norbornyl, methyl, ethyl, 4-fluorophenyl, cyclobutyl, cyclopentyl, cyclohexyl, n-propyl, n-butyl, n-pentyl, n-hexyl, n-octyl or n-decyl.

Particularly preferred compounds of the G Group are compounds wherein (a) $R^1$ is chloro, $R^2$ is methyl, $R^8$ is hydroxy or ethoxy, $R^9$ is cyclopropyl and $R^{10}$ is hydrogen, (b) $R^1$ is methyl, $R^2$ is methyl, $R^8$ is hydroxy or ethoxy, $R^9$ is cyclopropyl and $R^{10}$ is methyl, (c) $R^1$ is methyl, $R^2$ is methyl, $R^8$ is hydroxy or ethoxy, $R^9$ is cyclobutyl and $R^{10}$ is methyl, (d) $R^1$ is methyl, $R^2$ is methyl, $R^8$ is hydroxy or ethoxy, $R^9$ is cyclopropyl and $R^{10}$ is hydrogen and (e) $R^1$ is methyl, $R^2$ is methyl, $R^8$ is hydroxy or ethoxy, $R^9$ is cyclobutyl and $R^{10}$ is hydrogen; and pharmaceutically acceptable salts of said compounds.

A preferred group of compounds and pharmaceutically acceptable salts of such compounds, of the D Group, designated the J Group, contains those compounds of Formula I and pharmaceutically acceptable salts of such compounds, as shown above, wherein $R^4$ is —$C(O)NR^9R^{10}$, and $R^{10}$ is hydrogen, methyl or ethyl.

A preferred group of compounds and pharmaceutically acceptable salts of such compounds, of the J Group, designated the K group, contains those compounds of Formula I and pharmaceutically acceptable salts of such compounds, as shown above, wherein $R^9$ is methyl, ethyl, isopropyl, n-propyl, isobutyl, n-butyl, n-pentyl, n-hexyl, 4-fluorophenyl, —$CH_2$-2-thienyl, cyclopropyl, —$CH_2$-cyclopropyl, cyclobutyl, cyclopentyl, cyclohexyl, —$CH_2$-cyclohexyl, endo-2-norbornyl, exo-2-norbornyl, (S)-1-phenylethyl, (R)-1-phenylethyl, —$CH_2$-2-chlorophenyl, —$CH_2$-4-chlorophenyl, —$CH_2$-4-fluorophenyl, —$CH_2$-3-chloro-4-fluorophenyl, —$CH_2$-2-chloro-4-fluorophenyl, —$CH_2$-2-fluoro-4-chlorophenyl, —$CH_2$-3,4-difluorophenyl, —$CH_2$-4-isopropylphenyl, —$CH_2$-2,3-dichlorophenyl, —$CH_2$-2,4-dichlorophenyl, —$CH_2$-3,4-dichlorophenyl, —$CH_2$-3-trifluoromethyl-4-chlorophenyl, 4-phenylphenyl, 3-(2,4-dimethyl)pentyl, (R)-1-(1-naphthyl)ethyl, 1,1-dimethylpropyl, 1,2-dimethylpropyl, 2,2-dimethylpropyl, (R)-1-(2-naphthyl)ethyl, (R)-2-(1-naphthyl)ethyl, —$CH_2$-(1-naphthyl), (R)-1-cyclohexylethyl, (S)-1-cyclohexylethyl, —$CH_2$-3,4-methylenedioxyphenyl, —$CH_2$-4-t-butylphenyl, —$CH_2$-2,3-dichlorophenyl, 1-indanyl, (R)-1-indanyl, (S)-1-indanyl, 5-indanyl, 1-(1,2,3,4-tetrahydronaphthyl) or (R)-1-cyclohexylethyl.

Particularly preferred compounds of the K Group are compounds wherein (a) $R^1$ is chloro, $R^2$ is chloro, $R^8$ is hydroxy or ethoxy, $R^9$ is 3-(2,4-dimethyl)pentyl and $R^{10}$ is hydrogen, (b) $R^1$ is methyl, $R^2$ is methyl, $R^8$ is hydroxy or ethoxy, $R^9$ is cyclopropyl and $R^{10}$ is methyl, (c) $R^1$ is methyl, $R^2$ is methyl, $R^8$ is hydroxy or ethoxy, $R^9$ is cyclobutyl and $R^{10}$ is methyl, (d) $R^1$ is methyl, $R^2$ is methyl, $R^8$ is hydroxy or ethoxy, $R^9$ is 3-(2,4-dimethyl)pentyl and $R^{10}$ is hydrogen, (e) $R^1$ is methyl, $R^2$ is methyl, $R^8$ is hydroxy or ethoxy, $R^9$ is n-pentyl and $R^{10}$ is methyl, (g) $R^1$ is methyl, $R^2$ is methyl, $R^8$ is hydroxy or ethoxy, $R^9$ is isopropyl and $R^{10}$ is methyl, (h) $R^1$ is methyl, $R^2$ is methyl, $R^8$ is hydroxy, ethoxy or $NH_2$, $R^9$ is cyclobutyl and $R^{10}$ is methyl and (i) $R^1$ is chloro, $R^2$ is chloro, $R^8$ is hydroxy or ethoxy, $R^9$ is cyclobutyl and $R^{10}$ is methyl; and pharmaceutically acceptable salts of said compounds.

Another preferred group of compounds and pharmaceutically acceptable salts of such compounds, designated the L Group, contains those compounds of Formula I and pharmaceutically acceptable salts of such compounds, as shown above, wherein $R^4$ is —C(O)$NR^9R^{10}$, and $R^9$ and $R^{10}$ are taken together with the nitrogen atom to which they are attached to form $N(CH_2)_7$, $N(CH_2)_6$, $N(CH_2)_5$, $N(CH_2)_4$, morpholine,

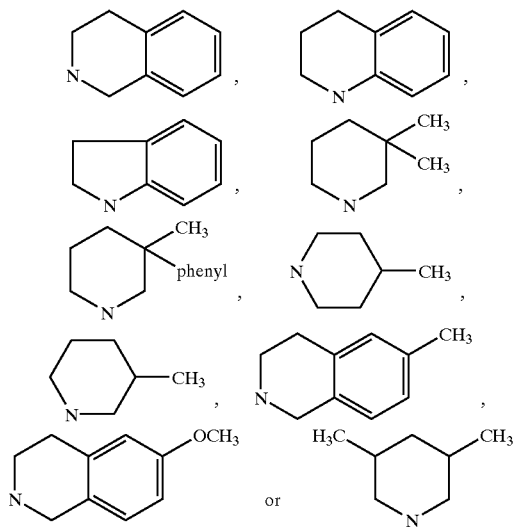

A preferred group of compounds and pharmaceutically acceptable salts of such compounds, of the D Group, designated the M Group, contains those compounds of Formula I and pharmaceutically acceptable salts of such compounds, as shown above, wherein $R^4$ is —$CH_2NR^9R^{10}$, and $R^{10}$ is hydrogen, methyl or —$COCH_3$.

A preferred group of compounds and pharmaceutically acceptable salts of such compounds, of the M Group, designated the N group, contains those compounds of Formula I and pharmaceutically acceptable salts of such compounds, as shown above, wherein $R^9$ is methyl, n-propyl, isopropyl, cyclopropyl, cyclobutyl, cyclopentyl, cyclohexyl, exo-2-norbornyl, —$CH_2$-4-fluorophenyl, —$CH_2$-4-chlorophenyl, —$CH_2$-4-isopropylphenyl, —$CH_2$-3,4-methylenedioxyphenyl, (R)-1-(1-naphthyl)ethyl, (R)-1-phenylethyl, (S)-1-phenylethyl, (R)-1-cyclohexylethyl, 1-(1,2,3,4-tetrahydronaphthyl), 1-indanyl or —$CH_2$-(1-naphthyl).

A preferred group of compounds and pharmaceutically acceptable salts of such compounds, of the D Group, designated the O group, contains those compounds of Formula I and pharmaceutically acceptable salts of such compounds, as shown above, wherein $R^4$ is —$CH_2NR^9R^{10}$ and $R^9$ and $R^{10}$ are taken together with the nitrogen atom to which they are attached to form $N(CH_2)_6$, morpholine,

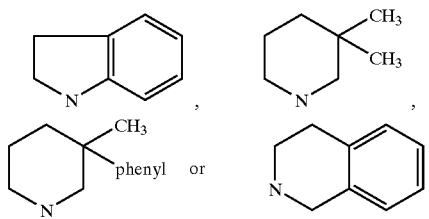

A preferred group of compounds and pharmaceutically acceptable salts of such compounds, of the D Group, designated the P Group, contains those compounds of Formula I and pharmaceutically acceptable salts of such compounds, as shown above, wherein $R^4$ is —$NHCOR^9$.

A preferred group of compounds and pharmaceutically acceptable salts of such compounds, of the P Group, designated the Q Group, contains those compounds of Formula I and pharmaceutically acceptable salts of such compounds, as shown above, wherein $R^9$ is cyclopropyl or cyclobutyl.

A preferred group of compounds and pharmaceutically acceptable salts of such compounds, of the D Group, designated the R Group, contains those compounds of Formula I and pharmaceutically acceptable salts of such compounds, as shown above, wherein $R^4$ is —$S(O)_2R^{12}$, and $R^{12}$ is 4-chlorophenyl, phenyl, 1-naphthyl, 2-naphthyl, $CH_2$-cyclopropyl, isopropyl, $CH_2$-cyclobutyl, $CH_2$-cyclohexyl, cyclopentyl, $CH_2$-4-fluorophenyl, 4-tolyl, methyl, ethyl, n-butyl, $CH_2$-phenyl or n-propyl.

Particularly preferred compounds of the R Group are compounds wherein (a) $R^1$ is chloro, $R^2$ is chloro, $R^8$ is hydroxy or ethoxy, and $R^{12}$ is ethyl, (b) $R^1$ is chloro, $R^2$ is chloro, $R^8$ is hydroxy or ethoxy and $R^{12}$ is —$CH_2$-cyclobutyl, (c) $R^1$ is chloro, $R^2$ is chloro, $R^8$ is hydroxy or ethoxy and $R^{12}$ is —$CH_2$-cyclohexyl, (d) $R^1$ is chloro, $R^2$ is chloro, $R^8$ is hydroxy or ethoxy and $R^{12}$ is cyclopentyl, (e) R is chloro, $R^2$ is chloro, $R^8$ is hydroxy or ethoxy, and $R^{12}$ is —$CH_2$-cyclopropyl, (f) $R^1$ is chloro, $R^2$ is chloro, $R^8$ is hydroxy or ethoxy, and $R^{12}$ is —$CH_2$-cyclobutyl, and (g) $R^1$ is methyl, $R^2$ is methyl, $R^8$ is hydroxy or ethoxy, and $R^{12}$ is —$CH_2$-cyclopropyl; and pharmaceutically acceptable salts of said compounds.

A preferred group of compounds and pharmaceutically acceptable salts of such compounds, of the B Group, designated the S Group, contains those compounds of Formula I and pharmaceutically acceptable salts of such compounds, as shown above, wherein $R^1$ and $R^2$ are each independently methyl, bromo or chloro, $R^3$ is hydrogen, $R^4$ and $R^5$ are taken together to form

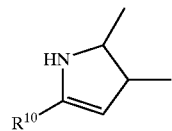

$R^6$ is hydrogen, $R^7$ is hydrogen, $R^8$ is ethoxy, hydroxy or $NH_2$, and $R^{10}$ is hydrogen or methyl.

A preferred group of compounds and pharmaceutically acceptable salts of such compounds, of the D Group, designated the T Group, contains those compounds of Formula I and pharmaceutically acceptable salts of such compounds, as shown above, wherein $R^3$ is hydrogen, and $R^4$ is —$OR^{11}$.

A preferred group of compounds and pharmaceutically acceptable salts of such compounds, of the T Group, designated the U Group, contains those compounds of Formula I and pharmaceutically acceptable salts of such compounds, as shown above, wherein $R^{11}$ is phenyl, 4-chlorophenyl or 4-fluorophenyl.

A preferred group of compounds and pharmaceutically acceptable salts of such compounds, of the D Group, designated the V Group, contains those compounds of Formula I and pharmaceutically acceptable salts of such compounds, as shown above, wherein $R^3$ is hydrogen, and $R^4$ is —($C_{1-6}$ alkyl)-$OR^{11}$. Particularly preferred compounds of the V Group are compounds wherein $R^4$ is —$CH_2$—$OR^{11}$.

A preferred group of compounds and pharmaceutically acceptable salts of such compounds, of the V Group, designated the W Group, contains those compounds of Formula I and pharmaceutically acceptable salts of such compounds, as shown above, wherein $R^{11}$ is phenyl or 4-fluorophenyl.

A preferred group of compounds and pharmaceutically acceptable salts of such compounds, of the D Group, designated the X Group, contains those compounds of Formula I and pharmaceutically acceptable salts of such compounds, as shown above, wherein $R^3$ and $R^4$ are taken together to form a carbocyclic ring A of the formula —$(CH_2)_b$— or a heterocyclic ring A selected from the group consisting of —Q—$(CH_2)_c$ and —$(CH_2)_j$—Q—$(CH_2)_k$— wherein Q is O, S or $NR^{17}$, wherein said carbocyclic ring A and said heterocyclic ring A are each independently optionally substituted with one or more substituents independently selected from $C_{1-4}$ alkyl, halide or oxo.

A preferred group of compounds and pharmaceutically acceptable salts of such compounds, of the X Group, designated the Y Group, contains those compounds of Formula I and pharmaceutically acceptable salts of such compounds, as shown above, wherein $R^3$ and $R^4$ are taken together to form said carbocyclic ring A.

A preferred group of compounds and pharmaceutically acceptable salts of such compounds, of the Y Group, designated the Z Group, contains those compounds of Formula I and pharmaceutically acceptable salts of such compounds, as shown above, wherein $R^3$ and $R^4$ are taken together to form —$(CH_2)_3$—, —$CH_2$—$C(CH_3)_2$—$CH_2$— or —$(CH_2)_4$—.

Particularly preferred compounds of the Z Group are compounds wherein (a) $R^1$ is methyl, $R^2$ is methyl, $R^8$ is hydroxy or ethoxy, and $R^3$ and $R^4$ are taken together to form —$(CH_2)_3$—, (b) $R^1$ is chloro, $R^2$ is methyl, $R^8$ is hydroxy or ethoxy, and $R^3$ and $R^4$ are taken together to form —$(CH_2)_3$— and (c) $R^1$ is methyl, $R^2$ is methyl, $R^8$ is hydroxy or ethoxy, and $R^3$ and $R^4$ are taken together to form —$(CH_2)_4$—; and pharmaceutically acceptable salts of said compounds.

A preferred group of compounds and pharmaceutically acceptable salts of such compounds, designated the AA Group, contains those compounds of Formula I and pharmaceutically acceptable salts of such compounds, as shown above, wherein $R^8$ is —$OR^9$.

A preferred group of compounds and pharmaceutically acceptable salts of such compounds, of the AA Group, designated the AB Group, contains those compounds of Formula I and pharmaceutically acceptable salts of such compounds, as shown above, wherein $R^9$ is $C_{1-12}$ alkyl.

A preferred group of compounds and pharmaceutically acceptable salts of such compounds, of the AB Group, designated the AC Group, contains those compounds of Formula I and pharmaceutically acceptable salts of such compounds, as shown above, wherein $R^9$ is methyl, isopropyl or ethyl.

A preferred group of compounds and pharmaceutically acceptable salts of such compounds, of the AC Group, designated the AD Group, contains those compounds of Formula I and pharmaceutically acceptable salts of such compounds, as shown above, wherein $R^9$ is ethyl.

A preferred group of the pharmaceutically acceptable salts of the compounds of Formula I, and the prodrugs, geometric and optical isomers thereof, contains those pharmaceutically acceptable salts of the compounds, prodrugs, and geometric and optical isomers wherein the salt is a potassium or a sodium salt.

A preferred group of compounds of Formula I, designated the AE Group, includes the specific compounds:
N-[3-chloro-4-(3-cyclopropylsulfamoyl-4-hydroxy-phenoxy)-5-methyl-phenyl]-oxamic acid,
N-[4-(3-cyclopropylsulfamoyl-4-hydroxy-phenoxy)-3,5-dimethyl-phenyl]-oxamic acid,
N-{4-[3-(cyclobutyl-methyl-carbamoyl)-4-hydroxy-phenoxy]-3,5-dimethyl-phenyl}-oxamic acid,
N-{3-chloro-4-[3-(cyclobutyl-methyl-carbamoyl)-4-hydroxy-phenoxy]-5-methyl-phenyl}-oxamic acid,
N-[4-(7-hydroxy-indan-4-yloxy)-3,5-dimethyl-phenyl]-oxamic acid,
N-{3,5-dichloro-4-[3-(cyclobutyl-methyl-carbamoyl)-4-hydroxy-phenoxy]-phenyl}-oxamic acid,
N-[3,5-dichloro-4-(3-cyclopentanesulfonyl-4-hydroxy-phenoxy)-phenyl]-oxamic acid,
N-[3,5-dichloro-4-(3-cyclopropylmethanesulfonyl-4-hydroxy-phenoxy)-phenyl]-oxamic acid,
N-[3,5-dichloro-4-(3-cyclobutylmethanesulfonyl-4-hydroxy-phenoxy)-phenyl]-oxamic acid,
N-[4-(3-cyclopropylmethanesulfonyl-4-hydroxy-phenoxy)-3,5-dimethyl-phenyl]-oxamic acid,
N-[3-chloro-4-(3-cyclobutylmethanesulfonyl-4-hydroxy-phenoxy)-5-methyl-phenyl]-oxamic acid,
N-[4-(3-cyclobutylmethanesulfonyl-4-hydroxy-phenoxy)-3,5-dimethyl-phenyl]-oxamic acid,
N-[4-(3-cyclopentylmethanesulfonyl-4-hydroxy-phenoxy)-3,5-dimethyl-phenyl]-oxamic acid,
N-[3-chloro-4-(3-cyclopentylmethanesulfonyl-4-hydroxy-phenoxy)-5-methyl-phenyl]-oxamic acid,
N-[3,5-dichloro-4-(3-cyclopentylmethanesulfonyl-4-hydroxy-phenoxy)-phenyl]-oxamic acid,
N-[4-(3-cyclohexylmethanesulfonyl-4-hydroxy-phenoxy)-3,5-dimethyl-phenyl]-oxamic acid,
N-[3-chloro-4-(3-cyclohexylmethanesulfonyl-4-hydroxy-phenoxy)-5-methyl-phenyl]-oxamic acid,
N-[3,5-dichloro-4-(3-cyclohexylmethanesulfonyl-4-hydroxy-phenoxy)-phenyl]-oxamic acid,
N-[3,5-dichloro-4-3-(4-fluoro-benzenesulfonyl)-4-hydroxy-phenoxy)-phenyl]-oxamic acid,
N-{4-[3-(4-fluoro-benzenesulfonyl)-4-hydroxy-phenoxy]-3,5-dimethyl-phenyl}-oxamic acid,
N-{3-chloro-4-[3-(4-fluoro-benzenesulfonyl)-4-hydroxy-phenoxy]-5-methyl-phenyl}-oxamic acid, and the prodrugs and geometric and optical isomers thereof, and the pharmaceutically acceptable salts of the compounds, prodrugs and isomers.

A preferred group of the pharmaceutically acceptable salts of the compounds, prodrugs, and geometric and optical isomers of the AE Group, designated the AF Group, contains those pharmaceutically acceptable salts of the compounds, prodrugs, and geometric and optical isomers wherein the salt is a potassium or a sodium salt.

A preferred group of the compounds, and geometric and optical isomers thereof, of the compounds of the AE group, designated the AG Group, contains the ethyl esters of those compounds.

A preferred group of compounds and pharmaceutically acceptable salts of such compounds, of the B Group, designated the AH Group, contains those compounds of Formula I and pharmaceutically acceptable salts of such compounds, as shown above, wherein $R^5$ is fluoro.

A preferred group of compounds and pharmaceutically acceptable salts of such compounds, of the AH Group, designated the AI Group, contains those compounds of Formula I and pharmaceutically acceptable salts of such compounds, as shown above, wherein $R^4$ is hydrogen, fluoro, chloro, methyl or cyclobutyl-methyl-carbamoyl.

A preferred group of compounds and pharmaceutically acceptable salts of such compounds, of the AI Group, designated the AJ Group, contains those compounds of Formula I and pharmaceutically acceptable salts of such compounds, as shown above, wherein $R^1$ and $R^2$ are each independently methyl or chloro.

A preferred group of compounds and pharmaceutically acceptable salts of such compounds, of the AJ Group, designated the AK Group, contains those compounds of Formula I and pharmaceutically acceptable salts of such compounds, as shown above, wherein $R^1$ and $R^2$ are each methyl.

A preferred group of compounds and pharmaceutically acceptable salts of such compounds, of the AJ Group, designated the AL Group, contains those compounds of Formula I and pharmaceutically acceptable salts of such compounds, as shown above, wherein $R^1$ and $R^2$ are each chloro.

A preferred group of compounds and pharmaceutically acceptable salts of such compounds, of the AJ Group, designated the AM Group, contains those compounds of Formula I and pharmaceutically acceptable salts of such compounds, as shown above, wherein $R^7$ is hydrogen, and $R^8$ is hydrogen or —$OR^9$.

A preferred group of compounds and pharmaceutically acceptable salts of such compounds, of the AM Group, designated the AN Group, contains those compounds of Formula I and pharmaceutically acceptable salts of such compounds, as shown above, wherein $R^9$ is methyl or ethyl.

A preferred group of compounds of Formula I, designated the AO Group, includes the specific compounds:

N-[4-(4-Fluoro-phenoxy)-3,5-dimethyl-phenyl]-oxamic acid,
N-[3,5-Dichloro-4-(4-fluoro-phenoxy)-phenyl]-oxamic acid,
N-[3,5-Dichloro-4-(3,4-difluoro-phenoxy)-phenyl]-oxamic acid,
N-[4-(3-Methyl-4-Fluoro-phenoxy)-3,5-dichloro-phenyl]-oxamic acid,
N-[3,5-Dichloro-4-(3-chloro-4-fluoro-phenoxy)-phenyl]-oxamic acid,
N-[4-(3,4-Difluoro-phenoxy)-3,5-dimethyl-phenyl]-oxamic acid,
N-[4-(3-Chloro-4-fluoro-phenoxy)-3,5-dimethyl-phenyl]-oxamic acid,
N-[4-(3-Methyl-4-fluoro-phenoxy)-3,5-dimethyl-phenyl]-oxamic acid,
N-[3,5-Dichloro-4-(4-fluoro-phenoxy)-phenyl]-oxamic acid,
N-[3,5-Dichloro-4-(3,4-difluoro-phenoxy)-phenyl]-oxamic acid,
N-{4-[3-(Cyclobutyl-methyl-carbamoyl)-4-fluoro-phenoxy)-3,5-dimethyl-phenyl]-oxamic acid,
N-[4-(4-Fluoro-phenoxy)-3,5-dimethyl-phenyl]-oxamic acid, and the prodrugs and geometric and optical isomers thereof, and the pharmaceutically acceptable salts of the compounds, prodrugs and isomers.

A preferred group of the pharmaceutically acceptable salts of the compounds, prodrugs, and geometric and optical isomers of the AO Group, designated the AP Group, contains those pharmaceutically acceptable salts of the compounds, prodrugs, and geometric and optical isomers wherein the salt is a potassium or a sodium salt.

A preferred group of the compounds, and geometric and optical isomers thereof, of the compounds of the AO group, designated the AQ Group, contains the ethyl esters of those compounds.

This invention provides methods of treating a condition selected from obesity, hyperlipidemia, glaucoma, cardiac arrhythmia, skin disorders, thyroid disease, hypothyroidism, diabetes mellitus, atherosclerosis, hypertension, coronary heart disease, hypercholesteremia, depression and osteoporosis, in a mammal (including a human being) which comprise administering to said mammal an effective treating amount of a compound of Formula I, or a prodrug thereof, or a geometric or an optical isomer thereof, or a pharmaceutically acceptable salt of such compound, such prodrug, or such isomer, as described above.

In another aspect, this invention provides methods of treating a condition selected from obesity, hyperlipidemia, glaucoma, cardiac arrhythmia, skin disorders, thyroid disease, hypothyroidism, diabetes mellitus, atherosclerosis, hypertension, coronary heart disease, hypercholesteremia, depression and osteoporosis, in a mammal (including a human being) which comprise administering to said mammal effective treating amounts of a compound of Formula I, or a prodrug thereof, or a geometric or an optical isomer thereof, or a pharmaceutically acceptable salt of such compound, such prodrug, or such isomer, as described above, and an anorectic agent.

In another aspect, this invention provides methods of treating a condition selected from obesity, hyperlipidemia, glaucoma, cardiac arrhythmia, skin disorders, thyroid disease, hypothyroidism, diabetes mellitus, atherosclerosis, hypertension, coronary heart disease, hypercholesteremia, depression and osteoporosis, in a mammal (including a human being) which comprise administering to said mammal effective treating amounts of a compound of Formula I, or a prodrug thereof, or a geometric or an optical isomer thereof, or a pharmaceutically acceptable salt of such compound, such prodrug, or such isomer, as described above, and a lipase inhibitor.

In a preferred aspect, this invention provides methods of treating obesity in mammals (including a human being) which comprise administering to said mammal an obesity treating effective amount of compound of Formula I, or a prodrug thereof, or a geometric or an optical isomer thereof, or a pharmaceutically acceptable salt of such compound, prodrug, or isomer, as described above.

In another aspect, this invention provides methods of treating obesity in mammals (including a human being) which comprise administering to said mammal obesity treating effective amounts of a compound of Formula I, or a prodrug thereof, or a geometric or an optical isomer thereof, or a pharmaceutically acceptable salt of such compound, prodrug, or isomer, as described above, and an anorectic agent.

In another aspect, this invention provides methods of treating obesity, in a mammal (including a human being) which comprise administering to said mammal obesity treating effective amounts of a compound of Formula I, or a prodrug thereof, or a geometric or an optical isomer thereof, or a pharmaceutically acceptable salt of such compound, such prodrug, or such isomer, as described above, and a lipase inhibitor.

In another aspect, this invention provides pharmaceutical compositions comprising a compound of Formula I, or a prodrug thereof, or a geometric or an optical isomer thereof, or a pharmaceutically acceptable salt of such compound, prodrug, or isomer, as described above, and a pharmaceutically acceptable vehicle, diluent or carrier.

In another aspect, this invention provides pharmaceutical compositions comprising a compound of Formula I, or a prodrug thereof, or a geometric or an optical isomer thereof, or a pharmaceutically acceptable salt of such compound, prodrug, or isomer, as described above, an anorectic agent and a pharmaceutically acceptable vehicle, diluent or carrier.

In another aspect, this invention provides pharmaceutical compositions comprising a compound of Formula I, or a prodrug thereof, or a geometric or an optical isomer thereof, or a pharmaceutically acceptable salt of such compound, prodrug, or isomer, as described above, a lipase inhibitor and a pharmaceutically acceptable vehicle, diluent or carrier.

In another aspect, this invention provides pharmaceutical compositions for treating a condition selected from obesity, hyperlipidemia, glaucoma, cardiac arrhythmia, skin disorders, thyroid disease, hypothyroidism, diabetes mellitus, atherosclerosis, hypertension, coronary heart disease, hypercholesteremia, depression and osteoporosis, in a mammal (including a human being) comprising a compound of Formula I, or a prodrug thereof, or a geometric or an optical isomer thereof, or a pharmaceutically acceptable salt of such compound, prodrug, or isomer, as described above, and a pharmaceutically acceptable vehicle, diluent or carrier.

In another aspect, this invention provides pharmaceutical compositions for treating a condition selected from obesity, hyperlipidemia, glaucoma, cardiac arrhythmia, skin disorders, thyroid disease, hypothyroidism, diabetes mellitus, atherosclerosis, hypertension, coronary heart disease, hypercholesteremia, depression and osteoporosis, in a mammal (including a human being) comprising a compound of Formula I, or a prodrug thereof, or a geometric or an optical isomer thereof, or a pharmaceutically acceptable salt of such compound, prodrug, or isomer, as described above, an anorectic agent, and a pharmaceutically acceptable vehicle, diluent or carrier.

In another aspect, this invention provides pharmaceutical compositions for treating a condition selected from obesity, hyperlipidemia, glaucoma, cardiac arrhythmia, skin disorders, thyroid disease, hypothyroidism, diabetes mellitus, atherosclerosis, hypertension, coronary heart disease, hypercholesteremia, depression and osteoporosis, in a mammal (including a human being) comprising a compound of Formula I, or a prodrug thereof, or a geometric or an optical isomer thereof, or a pharmaceutically acceptable salt of such compound, prodrug, or isomer, as described above, a lipase inhibitor, and a pharmaceutically acceptable vehicle, diluent or carrier.

In another preferred aspect, this invention provides pharmaceutical compositions for treating obesity in a mammal (including a human being) comprising a compound of Formula I, or a prodrug thereof, or a geometric or an optical isomer thereof, or a pharmaceutically acceptable salt of such compound, prodrug, or isomer, as described above, and a pharmaceutically acceptable vehicle, diluent or carrier.

In yet another aspect, this invention provides pharmaceutical compositions for treating obesity in a mammal (including a human being) comprising a compound of Formula I, or a prodrug thereof, or a geometric or an optical isomer thereof, or a pharmaceutically acceptable salt of such compound, prodrug, or isomer, as described above, an anorectic agent, and a pharmaceutically acceptable vehicle, diluent or carrier.

In yet another aspect, this invention provides pharmaceutical compositions for treating obesity in a mammal (including a human being) comprising a compound of Formula I, or a prodrug thereof, or a geometric or an optical isomer thereof, or a pharmaceutically acceptable salt of such compound, prodrug, or isomer, as described above, a lipase inhibitor, and a pharmaceutically acceptable vehicle, diluent or carrier.

In another aspect, this invention provides kits for the treatment of a condition selected from obesity, hyperlipidemia, glaucoma, cardiac arrhythmia, skin disorders, thyroid disease, hypothyroidism, diabetes mellitus, atherosclerosis, hypertension, coronary heart disease, hypercholesteremia, depression and osteoporosis which comprise: a first compound, said first compound being a compound of Formula I, or a prodrug thereof, or a geometric or an optical isomer thereof, or a pharmaceutically acceptable salt of such compound, prodrug, or isomer, as described above, and a pharmaceutically acceptable vehicle, carrier or diluent, in a first unit dosage form; a second compound, said second compound being an anorectic agent or a lipase inhibitor, and a pharmaceutically acceptable vehicle, carrier or diluent, in a second unit dosage form; and a container.

In another preferred aspect, this invention provides kits for the treatment of a obesity which comprise: a first compound, said first compound being a compound of Formula I, or a prodrug thereof, or a geometric or an optical isomer thereof, or a pharmaceutically acceptable salt of such compound, prodrug, or isomer, as described above, and a pharmaceutically acceptable vehicle, carrier or diluent, in a first unit dosage form; a second compound, said second compound being an anorectic agent or a lipase inhibitor, and a pharmaceutically acceptable vehicle, carrier or diluent, in a second unit dosage form; and a container.

Unless otherwise provided herein:

"alkyl" means a straight or branched hydrocarbon chain radical, including as the case may be, for example, methyl, ethyl, n-propyl, isopropyl, n-butyl and the like;

"alkenyl" means a straight or branched unsaturated, univalent aliphatic radical;

"alkoxy" means an alkyl radical which is attached to the remainder of the molecule by oxygen, including as the case may be, for example, methoxy;

"alkynyl" means a straight or branched acyclic hydrocarbon radical with one triple bond, including as the case may be, for example, acetylene;

"carbocyclic" (carbocycle) means an unsaturated, or a partially or fully saturated, ring having only carbon atoms in its nucleus, including as the case may be an aryl (an organic radical derived from an aromatic hydrocarbon by the removal of one atom, e.g., phenyl from benzene, also including, for example, naphthyl);

"cycloalkane" means a saturated, monocyclic hydrocarbon, including as the case may be, for example, cyclohexane;

"cycloalkyl" means a monocyclic or polycyclic radical derived from a cycloalkane, including as the case may be, for example, cyclohexyl;

"halo" or "halogen" means a radical derived from the elements fluorine, chlorine, bromine or iodine;

"heterocyclic" ("heterocycle") means a radical derived from an unsaturated, or a partially or fully saturated, monocyclic or polycyclic ring of different types of atoms, and includes aromatic and non-aromatic heterocyclic groups containing one or more heteroatoms each selected from O, S and N; examples of heterocyclic groups include, e.g., benzimidazolyl, benzofuranyl, benzothiophenyl, benzoxazolyl, furyl, imidazolyl, indolyl, isoquinolyl, isothiazolyl, isoxazolyl, morpholinyl, oxadiazolyl, oxazolyl, piperazinyl, piperidyl, pyranyl, pyrazinyl, pyrazolyl, pyridyl, pyrimidyl, pyrrolyl, quinolyl, tetrahydroisoquinoly, tetrahydroquinolyl, tetrahydrothienyl, tetrazolyl, thiadiazolyl, thiazolyl, thienyl, thiomorpholinyl, thiophenyl and triazolyl; where heterocyclic groups are specifically recited or covered as substituents for the compounds of Formula I, it is understood that, unless specifically noted otherwise, all suitable isomers of such heterocyclic groups are intended;

a "hydrate" is a crystalline substance containing one or more molecules of water of crystallization, i.e., a substance containing water combined in the molecular form;

"pharmaceutically acceptable" means that the carrier, diluent, vehicle excipients, and/or salt must be compatible with the other ingredients of the formulation, and not deleterious to the recipient thereof;

"pharmaceutically acceptable salts" of the compounds of this invention may be formed of the compound itself, prodrugs, e.g. esters, isomers and the like, and include all of the pharmaceutically acceptable salts which are most often used in pharmaceutical chemistry; for example, salts may be formed with inorganic or organic acids such as hydrochloric acid, hydrobromic acid, hydroiodic acid, carboxylic acids, sulfonic acids including such agents as naphthalenesulfonic, ethanesulfonic, hydroxyethanesulfonic, methanesulfonic ("mesylate"), benzenesulfonic ("besylate") and toluenesulfonic acids, e.g., p-toluenesulfonic ("tosylate"), sulfuric acid, nitric acid, phosphoric acid, tartaric acid, pyrosulfuric acid, metaphosphoric acid, succinic acid, formic acid, phthalic acid, malic acid, maleic acid, lactic acid, ascorbic acid, glycollic acid, gluconic acid, mandelic acid, glutamic acid, aspartic acid, fumaric acid, pyruvic acid, phenylacetic acid, pamoic acid, nicotinic acid, and the like; suitable pharmaceutically acceptable salts also include alkali metal salts (e.g. sodium, potassium salts), alkaline earth metal salts (e.g. magnesium, calcium salts), amine salts (e.g. ammonium, alkylammonium, dialkylammonium, trialkylammonium, tetraalkylammonium, diethanolaminium, tri-ethanolaminium and guanidinium salts); preferred salts include salts of organic acids selected from formic, acetic, trifluoroacetic, propionic, benzoic, citric, maleic, tartaric, methanesulfonic, benzenesulfonic or toluenesulfonic, salts of inorganic acids selected from hydrochloric, hydrobromic, sulfuric or phosphoric, amino acids selected from aspartic and glutamic, and salts of sodium and potassium;

a "polymorph" is a substance that occurs in two or more forms;

a "prodrug" is a drug precursor which, following administration, releases the drug in vivo via some chemical or physiological process (e.g., a prodrug on being brought to the physiological pH or through enzyme action is converted to the desired drug form); exemplary prodrugs upon cleavage release the corresponding free acid, and such hydrolyzable ester-forming residues of the compounds of Formula I include but are not limited to those having a carboxyl moiety wherein the free hydrogen is replaced by $(C_1-C_4)$alkyl, $(C_2-C_7)$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxy-carbonyloxy)ethyl having from 4 to 7 carbon atoms, 1-methyl-1-(alkoxy-carbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as b-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl;

a "radical" is a group of atoms that behaves as a single atom in a chemical reaction, e.g., an organic radical is a group of atoms which confers characteristic properties on a compound containing it, or which remains unchanged during a series of reactions;

a "solvate" is a molecular or ionic complex of molecules or ions of a solvent with those of a solute; a "solvate" wherein the solvent is water, forms "hydrates" or hydrated ions;

"spirocycloalkyl" means cycloalkyl having a spiro union (the union formed by a single atom which is the only common member of the rings); and "treating," "treat" or "treatment" includes, inter alia, preventative (e.g., prophylactic), palliative and curative treatment.

DETAILED DESCRIPTION OF THE INVENTION

Unless otherwise noted, throughout this document: ° C. is degrees Centigrade, % is percent, Calc. is calculated data, cm is centimeter, DEE is diethyl ether, DME is dimethyl ether, DMF is dimethylformamide, DMSO is dimethylsulfoxide, DTT is dithiothreitol, EtOAc is ethyl acetate, EtOH is ethanol, Found is found data, g is gram or grams, h is hour or hours, kg is kilogram or kilograms, KOH is potassium hydroxide, L is liter or liters, M is molar (concentration), MeOH is methanol, mg is milligram or milligrams, min is minute or minutes, mL is milliliter or milliliters, mm is millimole or millimoles, mM is millimolar (concentration), MS is mass spectrum, N is normal (concentration), NaOH is sodium hydroxide, nM is nanomolar (concentration), NMR is proton nuclear magentic resonance spectrum, psi is pounds per square inch, RT is room temperature, TEA is triethylamine, TFA is trifluoroacetic acid, THF is tetrahydrofuran, $\mu$g is microgram or micrograms, and $\mu$L is microliter or microliters.

As disclosed herein, a compound within the scope of Formula I shall at all times be understood to include all active forms of such compounds, including, for example, the free form thereof, e.g., the free acid or base form and also, all prodrugs, polymorphs, hydrates, solvates, stereoisomers, e.g., diastereomers and enantiomers, and the like, and all pharmaceutically acceptable salts as described above. It will also be appreciated that suitable active metabolites of compounds within the scope of Formula I, in any suitable form, are also included herein.

More specifically, certain compounds suitable for use in the present invention such as, for example, certain compounds of Formula I may have asymmetric centers and therefore exist in different enantiomeric forms. All suitable optical isomers and stereoisomers of such compounds, and mixtures thereof, are considered to be within the scope of the invention. With respect to such compounds, the present invention includes the use of a racemate, a single enantiomeric form, a single diastereomeric form, or mixtures thereof, as suitable. Moreover, such compounds may also exist as tautomers. Accordingly, the present invention relates to the use of all such suitable tautomers and mixtures thereof.

In addition, those skilled in the art will easily recognize that physiologically active compounds which have accessible hydroxy groups are frequently administered in the form of pharmaceutically acceptable esters. The compounds of this invention can be administered as esters, formed on the hydroxy groups. While the mechanism has not yet been investigated and not wishing to be bound by theory, it is believed that such esters are metabolically cleaved in the body, and that the actual drug is the hydroxy compound itself. It is possible, as has long been known in pharmaceutical chemistry, to adjust the rate or duration of action of the compound by suitable choices of ester groups.

Those skilled in the art will understand from this disclosure how to prepare the compounds of the present invention using any suitable known method. Moreover, the reaction SCHEMES of the present description illustrate the preparation of the compounds of the present invention and, unless otherwise indicated, $R^1$, $R^2$, $R^3$, $R^4$, $R^6$, $R^7$, $R^9$, $R^{10}$, X and Y in the reaction SCHEMES are as described above, Q of compound 14 of SCHEME A is preferably sodium or potassium, $X^1$ of SCHEMES D, I and L is preferably halide or sulfonate, T of SCHEMES K and L is as described below. In addition, the Examples provided herein further illustrate the preparation of the compounds of the present invention.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e.,$^2H$, can afford certain therapeutic advantages resulting from greater metabolic stability, for example increased in vivo half-life or reduced dosage requirements and, hence, may be preferred in some circumstances. Isotopically-labelled compounds of Formula I of this invention and prodrugs thereof can generally be prepared by carrying out the procedures disclosed in the SCHEME and/or in the EXAMPLES below, by substituting a readily available isotopically-labelled reagent for a non-isotopically labelled reagent.

The starting materials for each synthetic SCHEME and EXAMPLE provided by this description are either commercially available or can be prepared according to methods known to those skilled in the art such as described, for example, in the aforementioned U.S. Pat. Nos. 5,401,772; 5,569,674; and 5,654,468, and European Patent Specification published as EP 580,550.

The compounds of the present invention can be prepared from a common intermediate 1 as described below

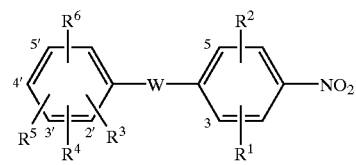

which itself may be synthesized according to any suitable method known in the art. More specifically, those skilled in the art will understand based upon the present disclosure how to prepare the common intermediate 1 wherein W is oxygen, $(SO_2)_d$, $CH_2$ or $NR^9$ where d and $R^9$ are as described above. It is particularly preferred that W is oxygen.

For example, common intermediate 1 wherein W is oxygen ("1(a)") can be prepared by either (a)

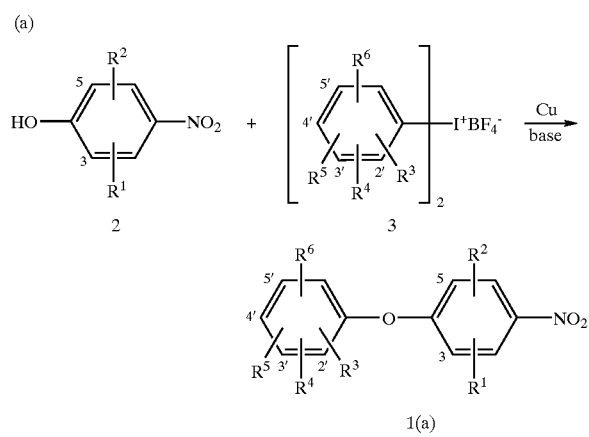

coupling a 4-nitrophenol (or a corresponding thiophenol) 2 with a bis-aryl iodonium tetrafluoroborate 3 at about RT in a suitable organic solvent such as, for example, dichloromethane, chloroform, DMF or DMSO, in the presence of a suitable copper catalyst such as, for example, copper bronze and a suitable base such as, for example, TEA, potassium-t-butoxide or sodium hydride (*J. Med. Chem*, 38: 695–707 (1995));

(b)

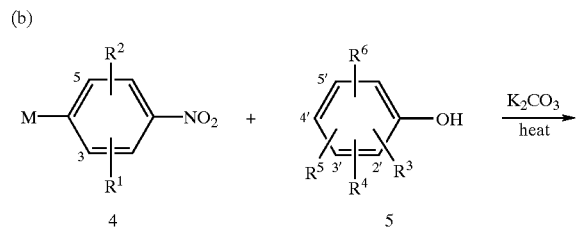

-continued

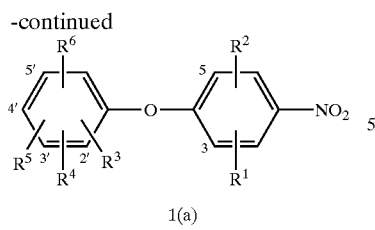

1(a)

coupling a 4-halonitrobenzene 4 (M is halogen), such as, for example, a 4-iodonitrobenzene, a 4-bromonitrobenzene, or a 4-chloronitrobenzene, with a phenol (or a thiophenol) 5 such as, for example, a 4-fluorophenol, at a suitable elevated temperature (greater than about 120° C., e.g., about 130° C.) in the presence of a suitable base such as, for example, potassium carbonate, potassium hydroxide, or potassium-t-butoxide, in a polar inert solvent such as, for example, DMSO or N-methylpyrrolidone (NMP); or (c)

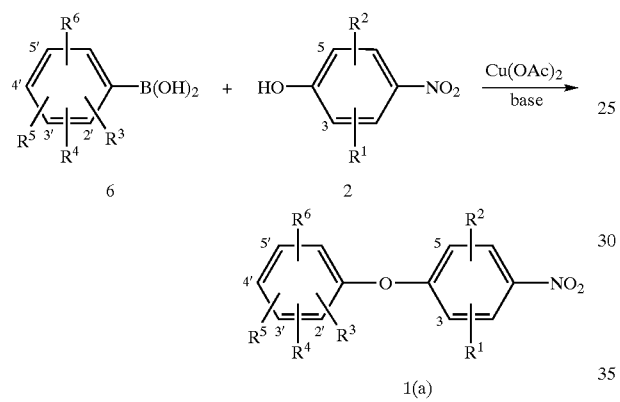

coupling (at RT in dichloromethane) a phenylboronic acid 6 with a 4-nitrophenol 2 in the presence of copper (II) acetate and a suitable base such as, for example, TEA, pyridine or a mixture of TEA and pyridine. (*Tetrahedron. Left.*, 39:2933–2936, 2937–2940 (1998)).

Embodiments of the present invention wherein $R^4$ of a compound of Formula I is located at the 3' position and is sulfonamide, amide, e.g., carboxamide, methylamino, carbamoyl or sulfamoyl, aryloxy, e.g., phenyloxy or benzyloxy, phenylsulfone or alkylsulfone, can be prepared, e.g., according to SCHEMES A and B, C and D, E, F, G and J, H, and I, respectively, provided by the present description hereinbelow.

In addition, a compound of Formula I wherein $R^4$ is located at the 3' position and $R^3$ is located at the 2' position and taken together are indanyl or tetrahydronaphthalyl can be prepared according to SCHEMES K and L, also provided by the present description hereinbelow.

Further, a compound of Formula I wherein $R^4$ is located at the 3' position and $R^5$ is located at the 4' position and $R^4$ and $R^5$ are taken together to form an indolyl can be prepared according to SCHEME M, provided hereinbelow.

Further yet, a compound of Formula I wherein $R^5$ is located at the 4' position and is fluoro can be prepared according to SCHEME N, provided hereinbelow.

In SCHEMES A and C described hereinbelow, the starting material ("A") is the common intermediate 1 wherein $R^5$ is located at the 4' position and is methoxy or ("MeO"). In SCHEMES E, H and I described hereinbelow, the starting material ("B") is the common intermediate 1 wherein $R^5$ is located at the 4' position and is MeO and $R^4$ is located at the 3' position and is hydrogen. In SCHEME N, the starting material ("C") is compound 5 wherein $R^5$ is at the 4' position and is fluoro.

It should be understood that the following SCHEMES are provided solely for the purposes of illustration and do not limit the invention which is defined by the claims.

SCHEME A

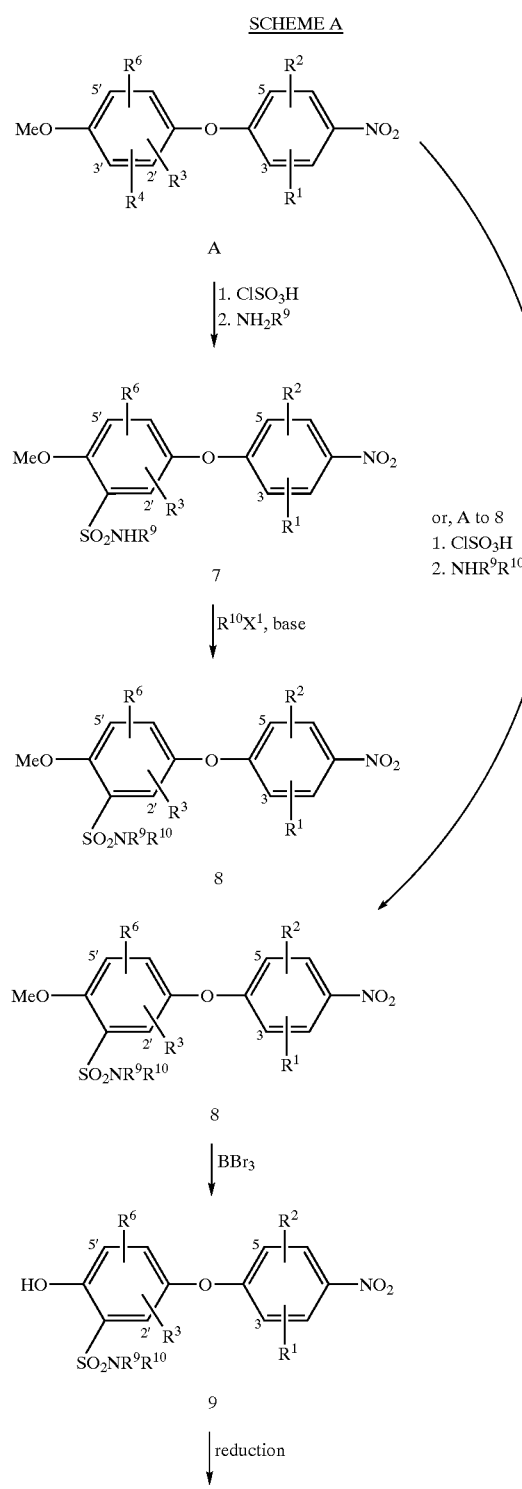

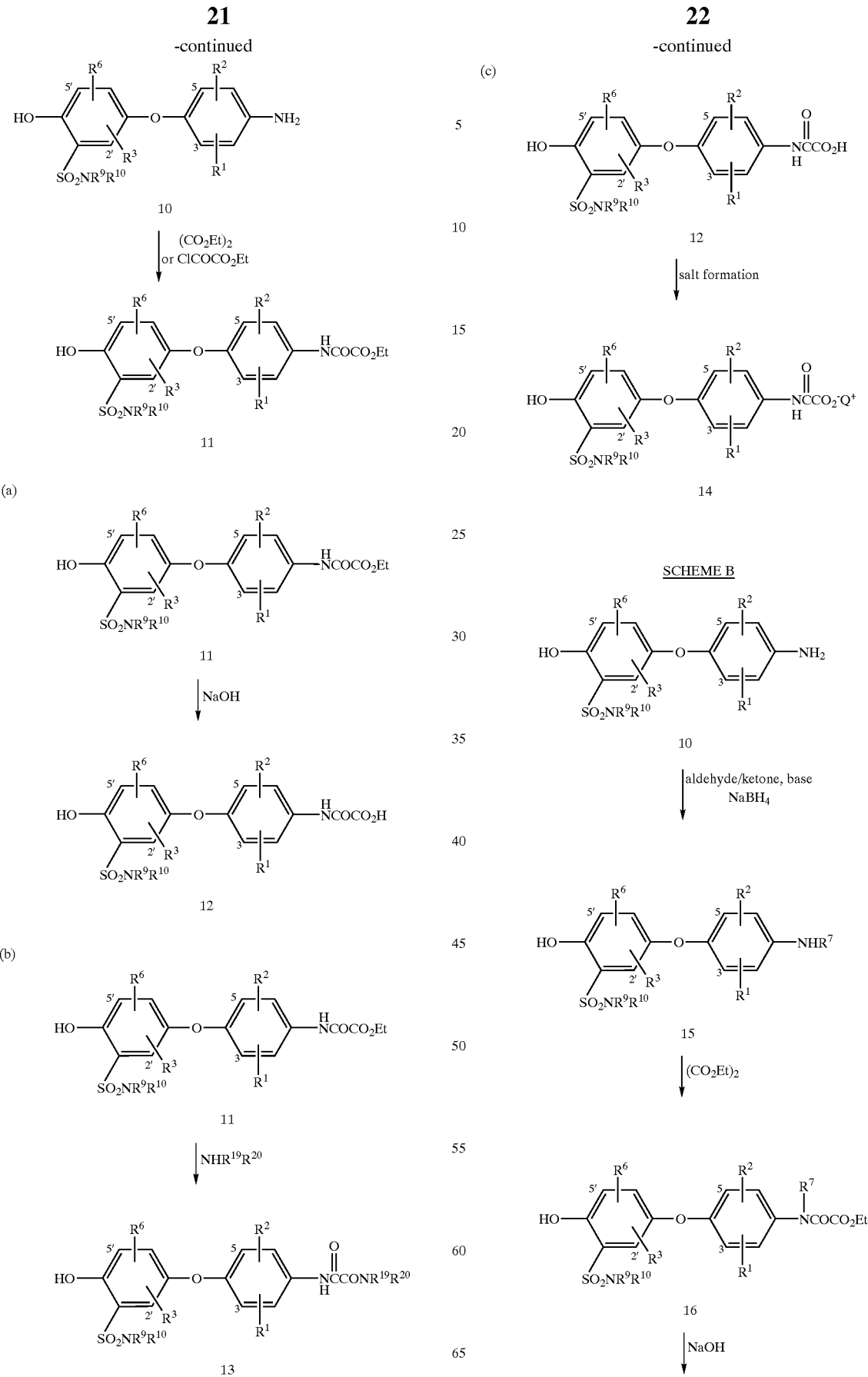

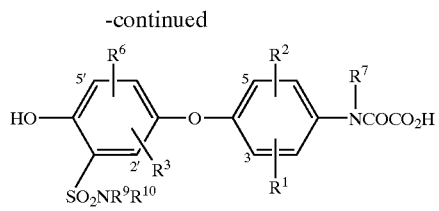
17
SCHEME C
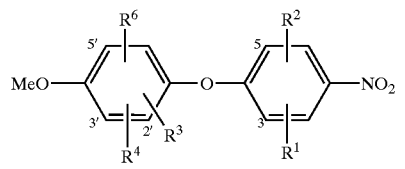
A
↓ formylation
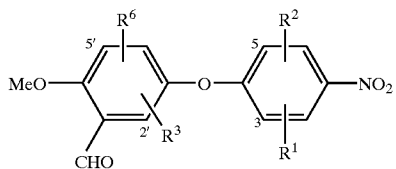
18
↓ oxidation
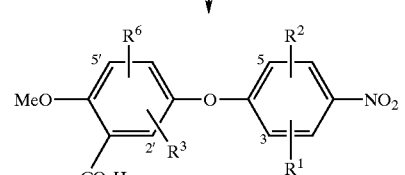
19
↓ 1. BBr₃
  2. H₂
  3. (CO₂Et)₂
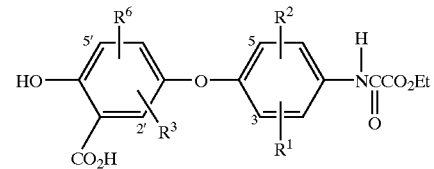
20
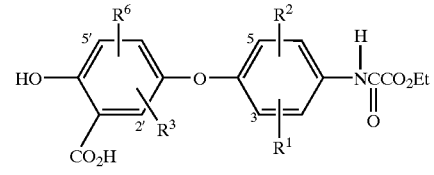
20
↓ coupling conditions/NHR⁹R¹⁰
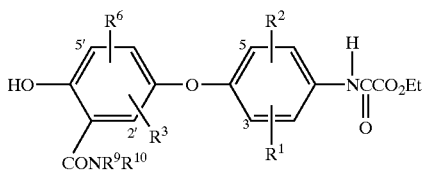
21
↓ NaOH
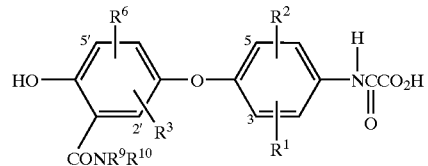
22
SCHEME D
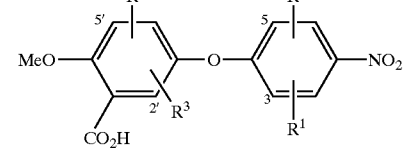
19
↓ coupling conditions
  NH₂R⁹
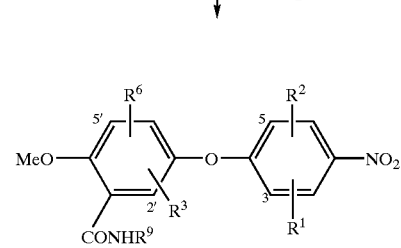
23
↓ R¹⁰X¹, base
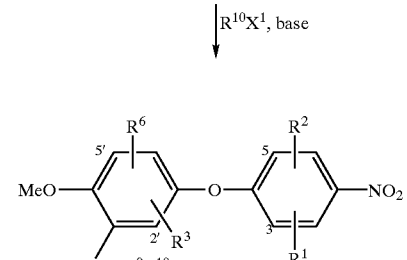
24
↓ 1. BBr₃
  2. H₂
  3. (CO₂Et)₂
or, 19 to 24 coupling conditions NHR⁹R¹⁰

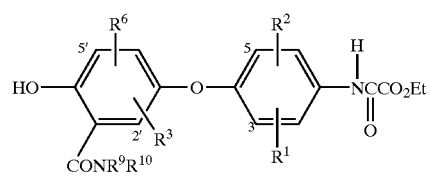
21
SCHEME E
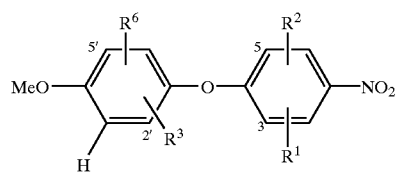
B
1. BBr₃
2. H₂
3. (CO₂Et)₂
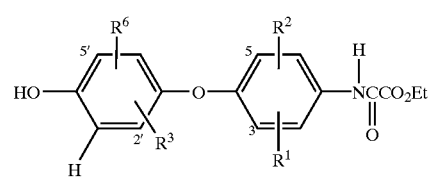
25
formylation
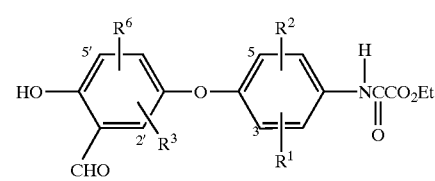
26
NHR⁹R¹⁰
NaBH₃CN
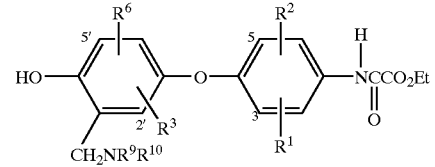
27
SCHEME F
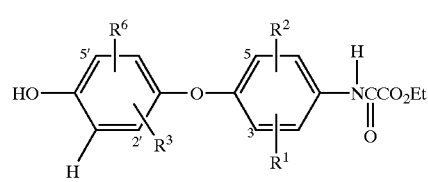
25
HNO₃
acetic acid
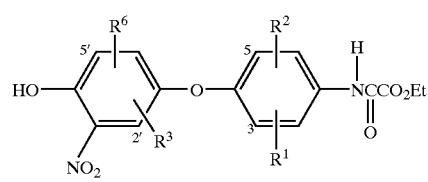
28
H₂
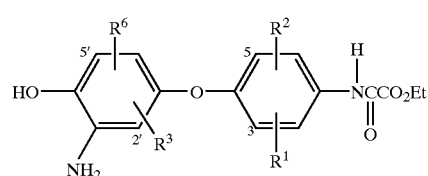
29
R¹⁰COCl
base
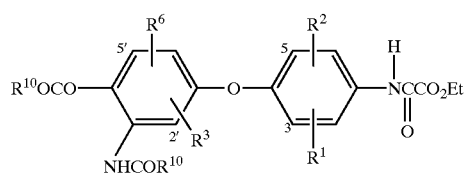
30
NaOH
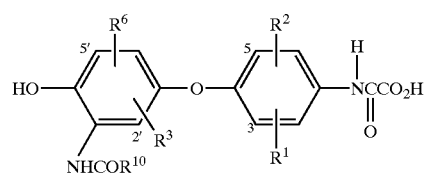
32

-continued
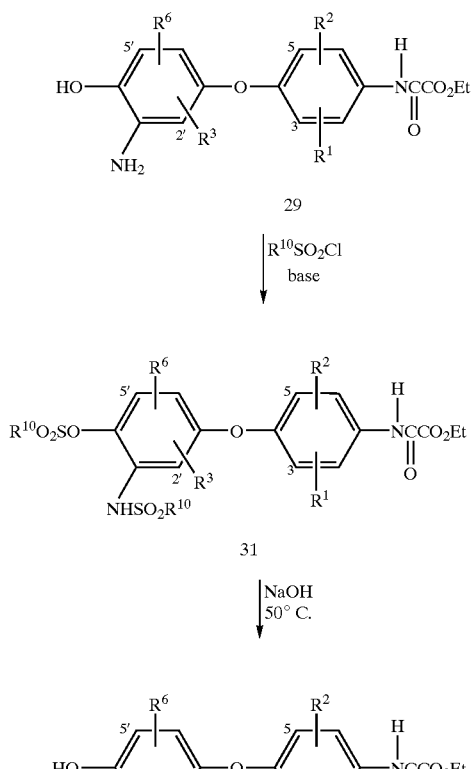
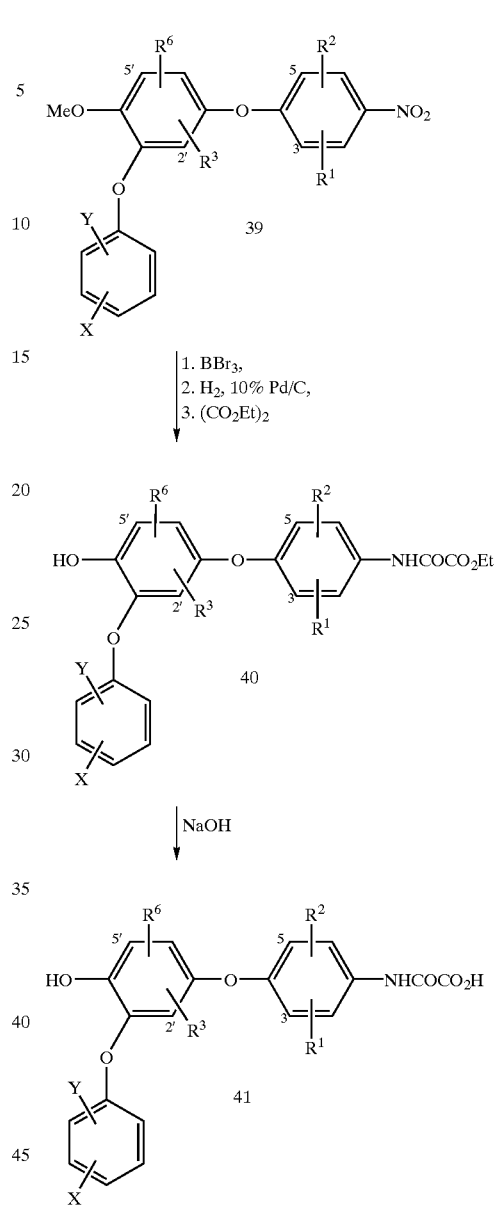
SCHEME G
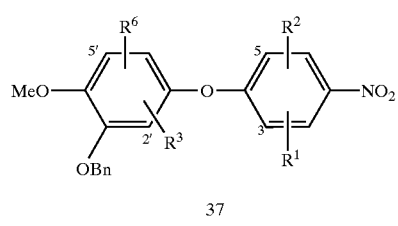
SCHEME H
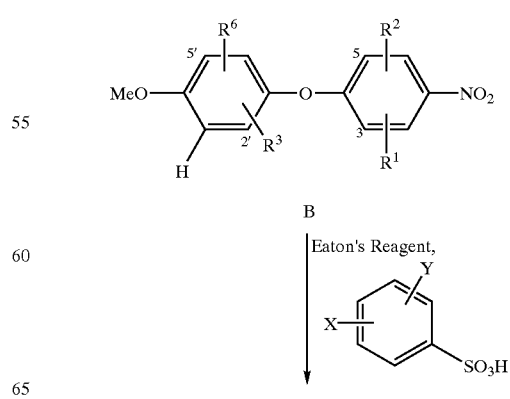

-continued
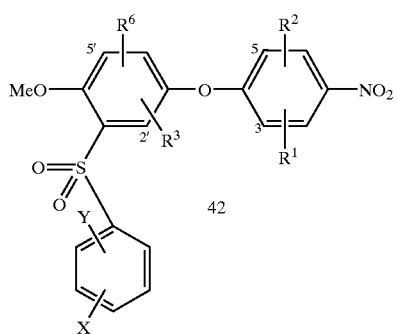
42
| 1. BBr₃,
| 2. H₂,
| 3. ClCOCOEt
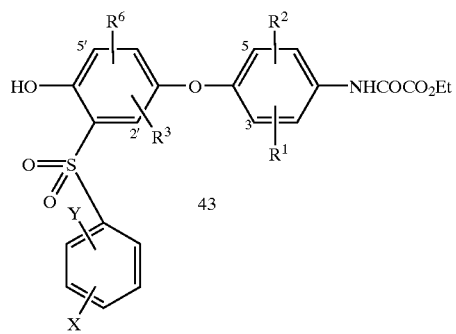
43
| hydrolysis
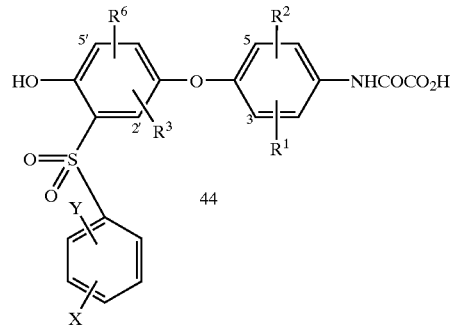
44
SCHEME I
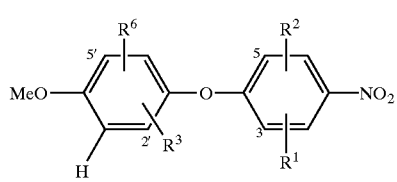
B
| 1. ClSO₂OH
| 2. Na₂SO₃, base, H₂O
-continued
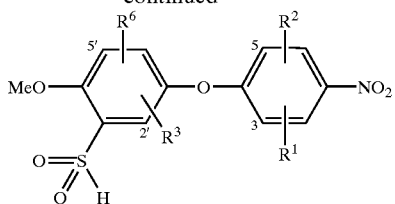
45
| R¹²X¹, base, EtOH
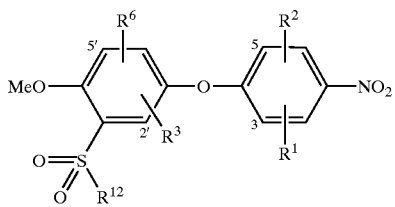
46
| 1. BBr₃,
| 2. H₂,
| 3. ClCOCO₂Et
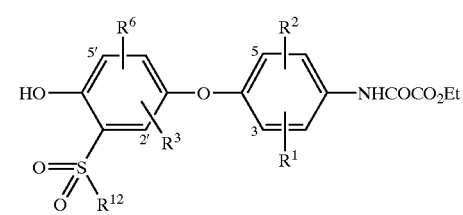
47
| hydrolysis
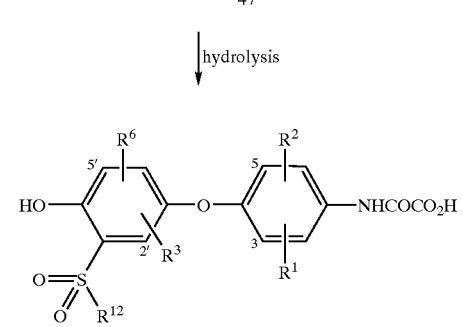
48
SCHEME J
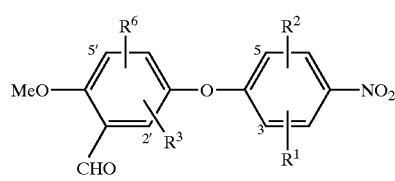
18
| BBr₃

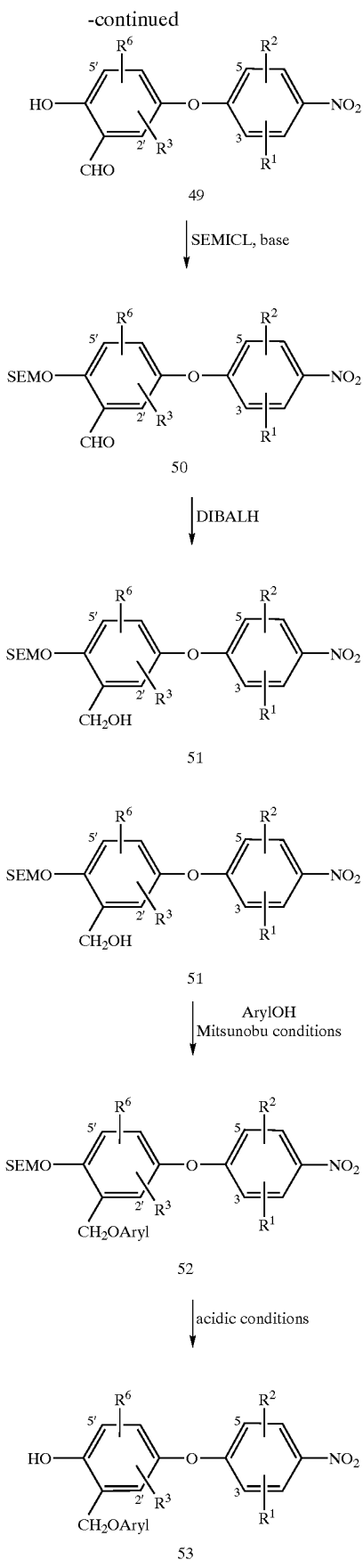
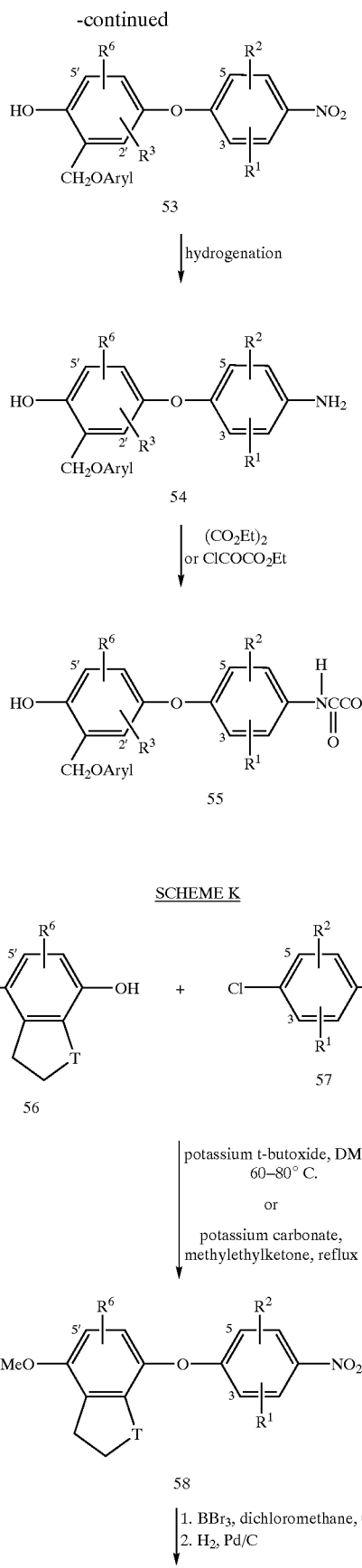

-continued
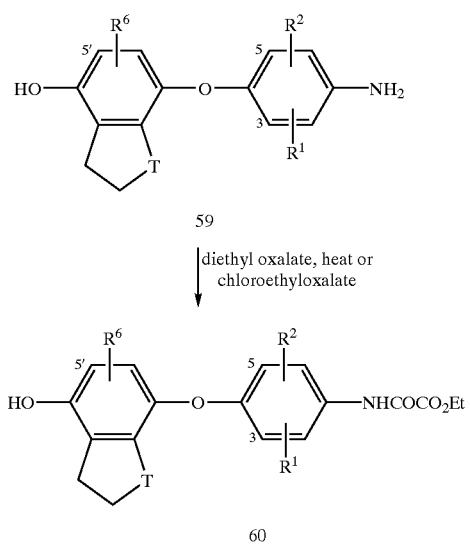
(a) 59 → (diethyl oxalate, heat or chloroethyloxalate) → 60
60 → (ammonia, methanol) → 62
(b) 60 → (NaOH, EtOH, H₂O) → 61
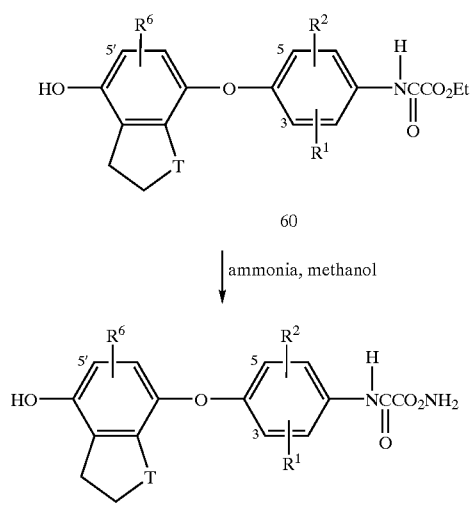
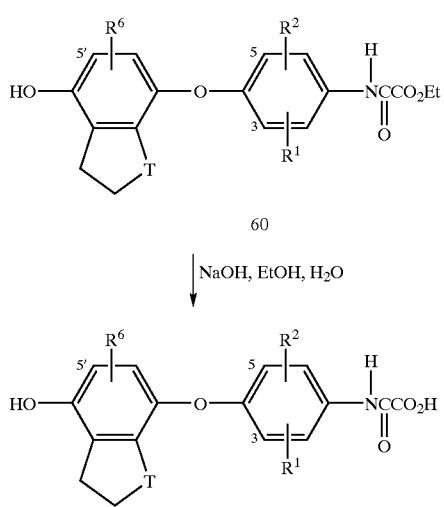
SCHEME L
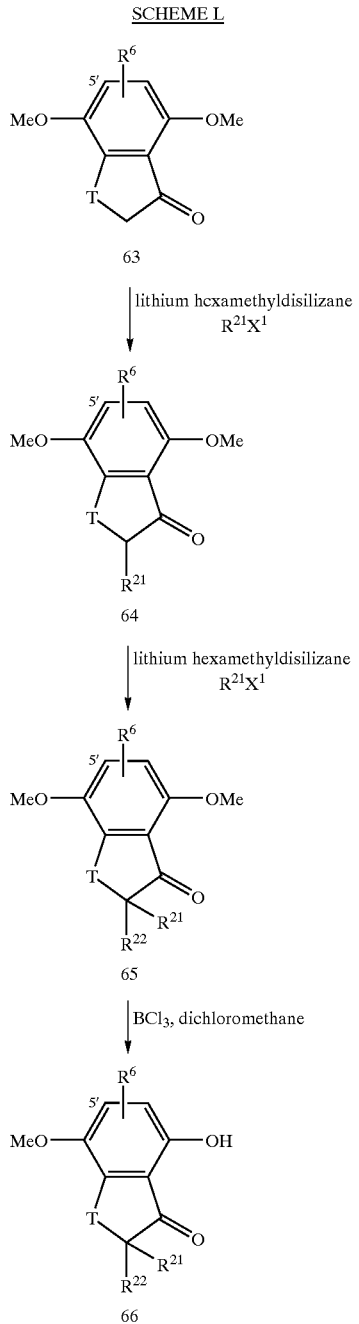
63 → (lithium hexamethyldisilizane, R²¹X¹) → 64 → (lithium hexamethyldisilizane, R²¹X¹) → 65 → (BCl₃, dichloromethane) → 66
SCHEME M
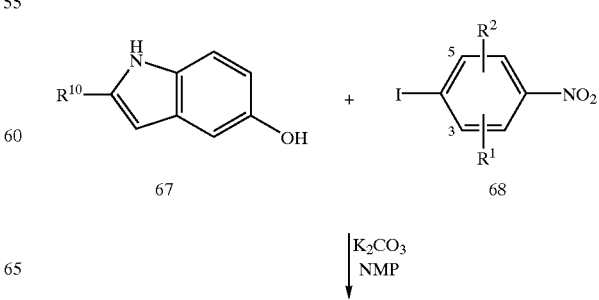
67 + 68 → (K₂CO₃, NMP)

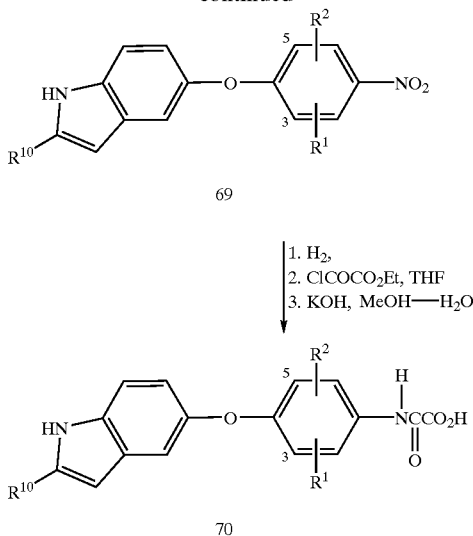

69

1. H₂,
2. ClCOCO₂Et, THF
3. KOH, MeOH—H₂O

70

SCHEME N

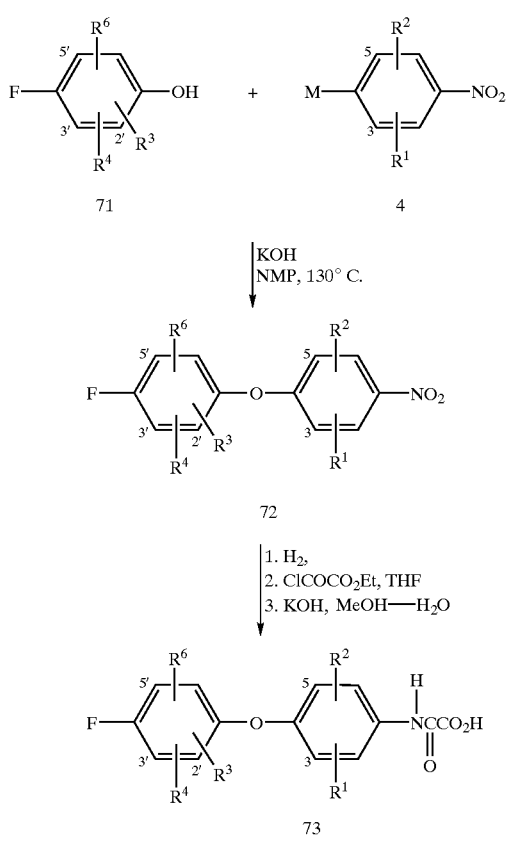

By Scheme A

The nitro intermediate A can be converted to the 3'-sulfonamide 7 or 8 by reaction of a 3'-chlorosulfonylated intermediate of A and a primary or secondary amine in a suitable solvent such as, for example, dichloromethane, THF, MeOH, EtOH or acetonitrile, in the presence of a suitable base such as, for example, TEA or diisopropylethylamine. Chlorosulfonylation of A can be performed by stirring a solution of A in a neat chlorosulfonic acid at from about 0° C. to about 25° C.

The sulfonamide 7 can be converted to the sulfonamide 8 by alkylation. A preferred alkylation method uses a suitable alkylated agent such as, for example, an alkyl halide, in the presence of a suitable base such as, for example, potassium carbonate, sodium hydride, potassium t-butoxide, NaOH or KOH, in a suitable organic solvent such as, for example, acetone, THF, DMSO, 2-propanol or an aqueous MeOH solution.

Demethylation of 8 to the phenol 9 can be accomplished by reaction of 8 with a suitable boron trihalide such as, for example, boron tribromide or boron trichloride, in a suitable organic solvent such as, for example, dichloromethane or chloroform. Nitro reduction of 9 to the aniline 10 can be effected using methods well known in the art such as, for example, hydrogenation or reduction with zinc dust or tin (II) chloride.

The aniline 10 can be converted to the oxamate 11 by reaction of 10 with diethyl oxalate at about 120° C. for from about 5 to about 24 h, or with ethyl oxalyl chloride at about RT in a suitable anhydrous aprotic solvent such as, for example, DEE, dichloromethane, chloroform or THF.

The oxamate 11 may be converted to the oxamic acid 12 and the oxamide 13 using conventional methods well known in the relevant art. For example, the ester 11 may be hydrolyzed to the acid 12 using suitable aqueous alkalides such as, for example, alkali metal carbonates or hydroxides in an aqueous MeOH solution. The oxamide 13 can be synthesized by reacting the ester 11 with an amine in a suitable solvent such as, for example, dichloromethane, chloroform, THF or MeOH.

The acid 12 can be converted to salts 14 such as, for example, metal or ammonium salts by treatment of 12 with an equivalent amount of the corresponding base such as, for example, alkali or ammonium hydroxides, or by exchange with carboxylic acid salts or alkali siloxides, or, by ion exchange methods known in the art.

By Scheme B

The primary aniline 10 can be converted to the secondary aniline 15 according to methods well known in the art for conversion of a primary to a secondary amine such as, for example, by reductive alkylation. A preferred reductive alkylation method employs an aldehyde, or a ketone, and a reducing agent in a suitable solvent and is best performed in the presence of about 3□ molecular sieves. Preferred reducing agents are sodium cyanoborohydride, sodium triacetoxyborohydride and sodium borohydride. Preferred organic solvents are EtOH and MeOH.

The resultant aniline 15 can be converted to the oxamate 16 and then the acid 17 by, e.g., methods analogous to those that have been previously described in SCHEME A discussed above.

By Scheme C

The nitro intermediate A can be converted to the aldehyde 18 by formylation. A preferred formylation method can be accomplished by reaction of A with hexamethylenetetramine at about 65° C. in a suitable solvent such as, for example, TFA.

The aldehyde 18 can be oxidized to the carboxylic acid 19 by methods well known in the art, e.g., Jones oxidation. Preferred oxidation methods include Jones oxidation and those employing sodium hypochlorite. Reaction of the aldehyde 18 with Jones reagent (chromic acid/aqueous sulfuric acid) in acetone affords the carboxylic acid 19.

The nitro containing carboxylic acid compound 19 can be converted to the oxamate 20 in three steps (demethylation, nitro reduction and oxamate formation) by, e.g., procedures analogous to those described in SCHEME A provided hereinabove.

The oxamate 20 can be converted to the 3'-carboxamide derivative 21 according to methods known in the art. For example, employment of an acid chloride or anhydride (symmetrical or mixed) of 20 with an amine in a suitable dried aprotic solvent such as, for example, dichloromethane, THF, DME or DEE, in the presence of a base such as TEA, dimethylaminopyridine or pyridine, are two commonly used methods. Another method utilizes the reaction of 20 and the requisite amine in an aprotic solvent with any of the standard carbodiimide coupling reagents such as, for example, dicyclohexylcarbodiimide, 2-ethoxy-1-ethoxycarbonyl-1,2-dihydroquinolone and benzotriazol-1-yloxytris(dimethylamino)-phosphonium-hexafluorophosphate.

The ester 21 can be hydrolyzed to the oxamic acid 22 by, e.g., the procedure analogous to that described in SCHEME A discussed above.

By Scheme D

The amide 23 can be prepared by reaction of an acid chloride or anhydride (symmetrical or mixed) of 19 with a primary amine in a suitable solvent such as, for example, dichloromethane, THF, DME, DEE in the presence of a base such as, for example, TEA, DMAP or pyridine.

The amide 23 can be alkylated to the amide 24 by reaction of carboxamide anion of 23 with a suitable alkylation agent such as, for example, an alkyl halide. The carboxamide anion of 23 can be generated in DMF with a suitable base such as, for example, sodium hydride or potassium hydride. The alkylation of 23 can also be performed by phase transfer catalysis without solvent or with a suitable solvent such as, for example, DMF or DMSO. The phase transfer reaction uses tetrabutylammonium bromide ("TBAB") as the phase transfer agent and potassium carbonate, KOH or NaOH as the base.

The amide 24 can be converted to the corresponding compound 21, e.g., in three steps by procedures analogous to those described in SCHEME A discussed above.

By Scheme E

The compound B can be converted to the oxamate 25, e.g., in three steps by procedures analogous to those described in SCHEME A provided hereinabove.

Formylation of 25 can be accomplished by a formylation procedure analogous to that described in SCHEME C provided hereinabove.

The aldehyde 26 can be converted to the, e.g., methylamino, derivative 27 by methods known in the art. A preferred method utilizes reductive amination. For example, the reductive amination can be accomplished by the reaction of the aldehyde 26 with an amine and a reducing agent in a suitable solvent and is best performed in the presence of 3□ molecular sieves. Preferred reducing agents are sodium cyanoborohydride, sodium triacetoxyborohydride and sodium borohydride. Preferred organic solvents include EtOH, MeOH and 1,2-dichloroethane.

By Scheme F

The oxamate 25 can be converted to the nitro compound 28 by nitration. The nitro compound 28 can be reduced to the corresponding aniline 29 by, e.g., catalytic hydrogenation or chemical reduction with zinc dust or tin (II) chloride. Acylation of 29 with carbonyl chloride in the presence of a suitable base such as, for example, TEA or N,N-diisopropylethylamine, affords diacylated compound 30. The diacylated oxamate 30 can be converted to the oxamic acid 32 by hydrolysis with a suitable base such as, for example, NaOH or KOH in an aqueous MeOH solution. Sulfonylation of 29 with sulfonyl chloride in the presence of a suitable base such as, for example, TEA or N,N-diisopropylethyl amine, yields disulfonylated compound 31.

Hydrolysis of 31 with a suitable base such as, for example, NaOH or KOH, in an aqueous MeOH solution at about 50° C. produces the oxamic acid 33.

By Scheme G

The benzyl ether 37 can be converted to the phenol 38 by debenzylation. Treatment of 37 with thioanisole in TFA at ambient temperature affords 38. Conversion of 38 to the phenyl ether 39 can be accomplished by coupling 38 with aryliodonium tetrafluoroborate and copper bronze in the presence of triethyl amine in dichloromethane or coupling 38 with arylboronic acid and copper (II) acetate in the presence of a suitable base such as, for example, TEA, pyridine, or a mixture of TEA and pyridine. Conversion of 39 to the oxamate 40 can be accomplished, e.g., in three steps (demethylation, nitro reduction and oxamate formation) according to procedures analogous to those described in Scheme A discussed above. The oxamic acid 41 is prepared by alkaline hydrolysis of ester 40.

By Scheme H

Treatment of B with an arylsulfonic acid in the presence of Eaton's Reagent at elevated temperature provides a 3'-aryl sulfone 42. Demethylation of 42 followed by hydrogenation and then reaction with ethyl oxalyl chloride provides the oxamate 43. The oxamate 43 may be hydrolysed to the oxamic acid 44 using a base, such as, for example, NaOH or KOH.

By Scheme I

The nitro compound B can be converted to the 3'-sulfinic acid 45 by treatment with chlorosulfonic acid followed by reduction with sodium sulfite in the presence of a base such as, for example, sodium bicarbonate or NaOH. Treatment of the sulfinic acid 45 with alkyl halide in the presence of a base such as, for example, NaOH, KOH, potassium t-butoxide, sodium hydride or sodium methoxide, provides the alkyl sulfone 46. The nitro compound 46 can be converted to the oxamate 47 via demethylation, hydrogenation and oxamate formation. Hydrolysis of the oxamate 47 under basic conditions provides the oxamic acid 48.

By Scheme J

The methyl ether 18 can be converted to the phenol 49 using procedures analogous to those described in SCHEME A. The phenol 49 can be protected as the trimethylsilylethoxymethyl ether 50 by treatment with a strong base such as, for example, sodium hydride or potassium t-butoxide in an aprotic solvent, e.g., THF, followed by treatment with trimethylsilylethoxymethyl chloride ("SEMCL").

Treatment of the aldehyde 50 with a reducing agent such as, for example, diisobutylaluminum hydride ("DIBALH") in an aprotic solvent, e.g., dichloromethane or THF affords 51. Reaction of alcohol 51 with a suitable phenol utilizing an azodicarbonyl compound, e.g., 1,1'-(azodicarbonyl) dipiperidine or diethylazo-dicarboxylate and a phosphine such as, for example, triphenyl- or tributylphosphine in an aprotic solvent, e.g., THF or toluene, provides the ether 52.

Removal of the "SEM" protecting group present in 52 under acidic conditions such as, for example, sulfuric or mineral acid in an alcoholic solvent, e.g., MeOH or EtOH, or alternatively, fluoride-mediated conditions (tetrabutylammonium fluoride/THF, hydrogen fluoride/acetonitrile) affords phenol 53. Reduction of the nitro group present in 53 by refluxing in acetic acid with a powdered metal, e.g., zinc or iron, provides the amine 54. Conversion to the oxamate 55 and the associated oxamic acids and oxamides is accomplished utilizing procedures analogous to those detailed in SCHEME A.

By Scheme K

Compounds 56–62 can be prepared according to procedures analogous to those described above in accordance with well known methods in the art. Those skilled in the art would understand from the present disclosure and, in particular, from SCHEME A, how to convert compound 62 to the oxamate derivatives detailed in SCHEME K. T completes, as discussed above where $R^3$ and $R^4$ are taken together, a carbocyclic ring A of the formula —$(CH_2)_b$— or a heterocyclic ring A selected from the group consisting of —Q—$(CH_2)_c$— and —$(CH_2)_j$—Q—$(CH_2)_k$— wherein b, Q, c, j and k are as described above, and wherein said carbocyclic ring A and said heterocyclic ring A are each independently optionally substituted with one or more substituents (e.g., $R^{21}$, $R^{22}$) independently selected from $C_{1-4}$ alkyl, halide or oxo, as also described above.

By Scheme L

Exhaustive treatment of 63 with a strong base such as, for example, lithium hexamethyidisilizane, lithium diisopropylamide or potassium t-butoxide and a suitable alkyl halide in an aprotic solvent, e.g., THF, affords the bis-alkylated intermediate 65. This process is carried out in a stepwise manner where $R^{21}$ and $R^{22}$ are different, and in a single reaction flask where $R^{21}$ and $R^{22}$ are the same.

One of the methyl ethers present in 65 can be selectively deprotected by utilizing boron trichloride or aluminum chloride in an aprotic solvent, e.g., dichloromethane or toluene.

Reduction of the ketone functionality present in 66 can be accomplished by treatment with a hydrosilane, preferably, triethylsilane, in the presence of an acid, e.g., methanesulfonic acid or TFA, with or without a solvent present. Solvents can be either protic or aprotic, with dichloromethane being preferred. Those skilled in the art will understand from the present disclosure how to convert the resultant reduced compounds to target oxamate derivatives. T is as described for SCHEME K.

By Scheme M

The indole 69 can be prepared by coupling the commercially available 5-hydroxy indole 67 with the 4-iodonitrobenzene 68 at about 125° C. in the presence of potassium carbonate for about 3 h. The nitro compound 69 is converted to the target compound 70 via hydrogenation and oxamate formation.

By Scheme N

The diaryl ether 72 is prepared by coupling of the commercially available fluorophenol 71 with the 4-halonitrobenzene 4 at 130° C. in NMP in the presence of KOH. The oxamic acid 73 is synthesized from the nitro compound 72 via hydrogenation, acylation, and hydrolysis.

In the preparation of the compounds of Formula I it is noted that, as would be appreciated by those skilled in the art, some of the methods useful for the preparation of such compounds, e.g., as exemplified by SCHEMES J and L discussed above, may require protection of a particular functionality, e.g., to prevent interference by such functionality in reactions at other sites within the molecule or to preserve the integrity of such functionality. The need for, and type of, such protection is readily determined by one skilled in the art, and will vary depending on, for example, the nature of the functionality and the conditions of the selected preparation method. See, e.g., T. W. Greene, *Protective Groups in Orqanic Svnthesis*, John Wiley & Sons, New York, 1991. Suitable protecting groups for any particular functionality would include those which are not substantially chemically reactive under the reaction conditions described and which can be removed without substantially chemically altering other functionalities of any given intermediate of the compound of Formula I, or of the compound of Formula I itself. The protecting group can be removed as so desired in any given preparation method, e.g., in a subsequent step.

Some of the Formula I compounds of this invention are acidic and they form a salt with a pharmaceutically acceptable cation. Some of the Formula I compounds of this invention are basic and they form a salt with a pharmaceutically acceptable anion. All such salts are within the scope of this invention and they can be prepared by conventional methods such as combining the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate. The compounds can be obtained in crystalline form by dissolution in an appropriate solvent(s) such as ethanol, hexanes or water/ethanol mixtures.

Preferred anorectic agents in the compositions, methods and kits of this invention include phenylpropanolamine, ephedrine, pseudoephedrine, phentermine, a neuropeptide Y antagonist, a cholecystokinin-A agonist, a monoamine reuptake inhibitor, a sympathiomimetic agent, a serotoninergic agent, a dopamine agonist, a melanocyte-stimulating hormone receptor agonist or mimetic, a cannabinoid receptor antagonist, a melanocyte-stimulating hormone analog, a melanin concentrating hormone antagonist, the OB protein, a leptin analog, a galanin antagonist and an orexin receptor antagonist.

A preferred monoamine reuptake inhibitor is sibutramine.
Preferred serotoninergic agents include dexfenfluramine and fenfluramine.
A preferred dopamine agonist is bromocriptine.
A preferred lipase inhibitor is tetrahydrolipstatin.

Suitable anorectic agents for the compositions, methods and kits of this invention can be prepared using methods known to those skilled in the art, for example, phentermine can be prepared as described in U.S. Pat. No. 2,408,345; sibutramine can be prepared as described in U.S. Pat. No. 4,929,629; fenfluramine and dexfenfluramine can be prepared as described in U.S. Pat. No. 3,198,834; and bromocriptine can be prepared as described in U.S. Pat. Nos. 3,752,814 and 3,752,888.

Suitable lipase inhibitors can be prepared using methods known to those skilled in the art, for example, tetrahydrolipstatin {(2S,3S,5S)-5-[(S)-2-formamido-4-methyl-valeryloxy]-2-hexyl-3-hydroxy-hexadecanoic 1,3 acid lactone} can be prepared as described in, e.g., U.S. Pat. Nos. 5,274,143; 5,420,305; 5,540,917; and 5,643,874.

The administration of a compound, prodrug, isomer or pharmaceutically acceptable salt of the present invention and an anorectic agent or a lipase inhibitor, as the case may be, according to this invention can be sequential in time or simultaneous with the simultaneous method being generally preferred. For sequential administration, a compound, a prodrug, an isomer or a pharmaceutically acceptable salt of the present invention and an anorectic agent or a lipase inhibitor, as the case may be, can be administered in any order. In addition, for sequential administration, the compound, prodrug, isomer or pharmaceutically acceptable salt of the present invention and the anorectic agent (or the lipase inhibitor as the case may be), can be administered in any order. It is generally preferred that such administration be oral. It is even more preferred that the administration be oral and simultaneous. However, for example, if the subject being treated is unable to swallow, or oral absorption is otherwise impaired or undesirable, parenteral or transdermal administration will be appropriate. Where the administration is sequential, the administration of a compound, prodrug, isomer or pharmaceutically acceptable salt of the present invention and an anorectic agent or a lipase inhibitor, as the case may be, can be by the same method or by different methods.

The dose of a compound, prodrug, isomer or pharmaceutically acceptable salt of this invention to be administered to a human or animal is rather widely variable and subject to the judgment of the attending physician or veterinarian. As would be understood by those skilled in the art, it may be necessary to adjust the dose of a compound, prodrug or isomer of this invention when it is administered in the form of a salt, e.g., where the salt forming moiety of which has an appreciable molecular weight. The general range of effective administration rates of the compounds, prodrugs, isomers or pharmaceutically acceptable salts of this invention is from about 0.001 mg/kg body weight to about 100 mg/kg body weight of the subject per day. A preferred range of effective administration rates of the compounds, prodrugs, isomers or pharmaceutically acceptable salts of this invention is from about 0.01 mg/kg body weight to about 50 mg/kg body weight of the subject per day. While it may be practical to administer the daily dose of a compound, prodrug, isomer or pharmaceutically acceptable salt of this invention, in portions, at various hours of the day, in any given case, the amount of compound, prodrug, isomer or pharmaceutically acceptable salt administered will depend on such factors as the solubility of the compound, prodrug, isomer or pharmaceutically acceptable salt of this invention, the formulation used and the route of administration (e.g., orally, transdermally, parenterally or topically).

Dosages of the compounds, prodrugs, isomers and pharmaceutically acceptable salts of the present invention can be administered to humans by any suitable route, with oral administration being preferable. Individual tablets or capsules should generally contain from about 0.1 mg to about 100 mg of compound, prodrug, isomer or pharmaceutically acceptable salt of this invention, in a suitable pharmaceutically acceptable vehicle, diluent or carrier. Dosages for intravenous administration are generally within the range of from about 0.1 mg to about 10 mg per single dose as required. For intranasal or inhaler administration, the dosage is generally formulated as from about a 0.1% to about a 1% (w/v) solution. In practice, the physician will determine the actual dosage which will be most suitable for an individual patient and it will vary with, e.g., age, weight and response of the particular patient. The above dosages are exemplary of the average case but there can, of course, be individual instances where higher or lower dosage ranges are merited, and all such dosages of compounds, prodrugs, isomers and pharmaceutically acceptable salts of this invention, are within the scope of the present invention.

Any suitable dosage of an anorectic agent can be used in aspects of the present invention comprising such agents. The dosage of the anorectic agent is generally in the range of from about 0.01 to about 50 mg/kg body weight of the subject per day, preferably from about 0.1 to about 10 mg/kg body weight of the subject per day, administered singly or as a divided dose. For example, where the anorectic agent is phentermine, the dosage of phentermine is from about 0.01 to 50 mg/kg body weight of the subject per day, preferably from about 0.1 to about 1 mg/kg body weight of the subject per day. In addition, where the anorectic agent is sibutramine, the dosage range is from about 0.01 to about 50 mg/kg body weight of the subject per day, preferably from about 0.1 to about 1 mg/kg body weight of the subject per day; where the anorectic agent is dexfenfluramine or fenfluramine, the dosage range is from about 0.01 to about 50 mg/kg body weight of the subject per day, preferably from about 0.1 to about 1 mg/kg body weight of the subject per day; and where the anorectic agent is bromocriptine, the dosage range is from about 0.01 to about 10 mg/kg body weight of the subject per day, preferably from about 0.1 to about 10 mg/kg body weight of the subject per day. In practice, the physician will determine the actual dosage of anorectic agent which will be most suitable for an individual patient and it will vary with, e.g., age, weight and response of the particular patient. The above dosages of anorectic agents are exemplary but there can, of course, be individual instances where higher or lower dosage ranges of such anorectic agents are merited, and all such dosages are within the scope of the present invention.

Any suitable dosage of a lipase inhibitor can be used in aspects of the present invention comprising such inhibitors. The dosage of the lipase inhibitor is generally in the range of from about 0.01 to about 50 mg/kg body weight of the subject per day, preferably from about 0.05 to about 10 mg/kg body weight of the subject per day, administered singly or as a divided dose. For example, where the lipase inhibitor is tetrahydrolipstatin, the dosage of tetrahydrolipstatin is preferably from about 0.05 to 2 mg/kg body weight of the subject per day. In practice, the physician will determine the actual dosage of lipase inhibitor which will be most suitable for an individual patient and it will vary with, e.g., age, weight and response of the particular patient. The above dosages of lipase inhibitors are exemplary but there can, of course, be individual instances where higher or lower dosage ranges of such lipase inhibitors are merited, and all such dosages are within the scope of the present invention.

Any suitable route of administration may be used in the present invention. It is usually preferred to administer the compounds, prodrugs, isomers and pharmaceutically acceptable salts of this invention orally for reasons of convenience; however, they may be administered, for example, percutaneously, or as suppositories for absorption by the rectum, as desired in a given instance. As described above, the administration may be carried out in single or multiple doses, as appropriate.

The compounds, prodrugs, isomers and pharmaceutically acceptable salts of this invention may be administered alone, and are preferably administered as pharmaceutical compositions comprising a pharmaceutically acceptable vehicle, carrier or diluent. The pharmaceutical compositions of the invention will comprise a suitable amount of a compound, prodrug, isomer or pharmaceutically acceptable salt of this invention, i.e., an amount sufficient to provide the desired dosage.

The compounds, prodrugs, isomers and pharmaceutically acceptable salts of this invention can be administered in a wide variety of different dosage forms, i.e., they may be combined with various pharmaceutically acceptable inert carriers in any suitable form. Such carriers include solid diluents or fillers, sterile aqueous media and various non-toxic organic solvents. The pharmaceutical compositions can be formulated to contain a daily dose, or a convenient fraction of a daily dose, in a dosage unit, which may be a single tablet or a capsule or a convenient volume of a liquid.

All of the usual types of pharmaceutical compositions may be used in the present invention, including tablets, lozenges, hard candies, chewable tablets, granules, powders, sprays, capsules, pills, microcapsules, solutions, parenteral solutions, troches, injections (e.g., intravenous, intraperitoneal, intramuscular or subcutaneous), suppositories, elixirs, syrups and suspensions.

For parenteral administration, the compounds, prodrugs, isomers and pharmaceutically acceptable salts of this invention may be used as solutions in sesame or peanut oil, or as aqueous solutions (e.g., aqueous propyleneglycol), as the case may be, and they are best used in the form of a sterile aqueous solution which may contain other substances; for example, enough salts or glucose to make the solution isotonic, the pH of the solution being suitably adjusted and buffered, where necessary, and surfactants such as, for example, hydroxypropylcellulose. Such oily solutions are suitable for intra-articular, intramuscular and subcutaneous injection purposes. Such aqueous solutions are suitable for intravenous injection purposes.

The compounds, prodrugs, isomers and pharmaceutically acceptable salts of this invention may also be administered topically and this may be done by way of, e.g., creams, jellies, salves, lotions, gels, pastes, ointments, and the like, in accordance with standard pharmaceutical practice. The compounds, prodrugs, isomers and pharmaceutically acceptable salts of this invention of the present invention may also be administered transdermally (e.g., through the use of a patch). Any suitable formulation for transdermal application comprising a compound of the present invention may be employed and such formulations would generally also contain a suitable transdermal carrier, e.g., an absorbable pharmacologically acceptable solvent to promote and assist passage of the compounds through the subject's skin. For example, suitable transdermal devices may comprise the form of a bandage having a backing member and a reservoir containing the subject compound. Such bandage-type transdermal devices may further include suitable carriers, rate-controlling barriers, and means for securing the transdermal device to the subject's skin.

As will be described in detail hereinbelow, the pharmaceutical compositions can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate, or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone, or aluminum stearate), a dispersing agent (e.g., hydroxypropylmethylcellulose), a diluent (e.g., water), a coloring agent, an emulsifying agent, and a base wax (e.g., cocoa butter, white petrolatum or polyethylene glycol).

Any of the compounds, prodrugs, isomers or pharmaceutically acceptable salts of this invention may be readily formulated as tablets, capsules, and the like. It is preferable to prepare solutions from water-soluble salts, such as the hydrochloride salt.

In general, all of the pharmaceutical compositions are prepared according to methods usual in pharmaceutical chemistry.

Capsules can be prepared by mixing a compound, prodrug, isomer or pharmaceutically acceptable salt of the invention with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as a compound, prodrug, isomer or pharmaceutically acceptable salt of this invention. Common diluents include, for example, various types of starch, lactose, mannitol, kaolin, calcium phosphate or sulfate, inorganic salts such as sodium chloride and powdered sugar. Powdered cellulose derivatives may also be used. Common tablet binders include substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is generally necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators include substances which swell when wetted to break up the tablet and release a compound, prodrug, isomer or pharmaceutically acceptable salt of this invention. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used as well as sodium lauryl sulfate.

Tablets are often coated with sugar as a flavor and sealant, or with film-forming protecting agents to modify the dissolution properties of the tablet. The compounds, prodrugs, isomers and pharmaceutically acceptable salts of this invention may also be formulated as chewable tablets, by using large amounts of pleasant-tasting substances such as mannitol in the formulation, as is now well-established in the art.

Where it is desired to administer a compound, prodrug, isomer or pharmaceutically acceptable salt of this invention as a suppository, any suitable base can be used. Cocoa butter is a traditional suppository base, which may be modified by the addition of waxes to raise its melting point. Water-miscible suppository bases comprising, particularly, polyethylene glycols of various molecular weights are in wide use.

As discussed above, the effect of a compound, prodrug, isomer or pharmaceutically acceptable salt of this invention may be delayed or prolonged by proper formulation. For example, a slowly soluble pellet of a compound, prodrug, isomer or pharmaceutically acceptable salt of this invention may be prepared and incorporated in a tablet or capsule. The technique may be improved by making pellets of several different dissolution rates and filling capsules with a mixture of the pellets. Tablets or capsules may be coated with a film which resists dissolution for a predictable period of time. The parenteral preparations may also be made long-acting by dissolving or suspending a compound, prodrug, isomer or pharmaceutically acceptable salt of this invention, as the case may be, in oily or emulsified vehicles which allow it to disperse only slowly in the serum.

The compounds, prodrugs, isomers and pharmaceutically acceptable salts of this invention may also be administered to a mammal other than a human. The method of administration and the dosage to be administered to such a mammal will depend, for example, on the animal species and the disease or disorder being treated. The compounds, prodrugs, isomers and pharmaceutically acceptable salts of this invention may be administered to animals in any suitable manner, e.g., orally, parenterally or transdermally, in any suitable form such as, for example, a capsule, bolus, tablet, pellet, e.g., prepared by admixing a compound, prodrug, isomer or pharmaceutically acceptable salt of this invention with a suitable diluent such as carbowax or carnuba wax together with a lubricant, liquid drench or paste, e.g., prepared by dispersing a compound, prodrug, isomer or pharmaceutically acceptable salt of this invention in a pharmaceutically acceptable oil such as peanut oil, sesame oil or corn oil. The compounds, prodrugs, isomers and pharmaceutically acceptable salts of this invention may also be administered to animals as an implant. Such formulations are prepared in a conventional manner in accordance with standard veterinary practice. As an alternative, the compounds, prodrugs, isomers and pharmaceutically acceptable salts of this invention may be administered with the water supply, e.g., in the form of a liquid or water-soluble concentrate. In addition, the compounds, prodrugs, isomers and pharmaceutically acceptable salts of this invention, e.g., within the pharmaceutical compositions of the invention, may be administered in the animal feedstuff, e.g., a concentrated feed additive or premix may be prepared for mixing with the normal animal feed, commonly along with a suitable carrier therefor. The carrier facilitates uniform distribution of a compound, prodrug, isomer or pharmaceutically acceptable salt of this invention in the, e.g., finished feed with which the premix is blended. Suitable carriers include, but are not limited to, liquids, e.g., water, oils such as soybean, corn, cottonseed, or volatile organic solvents, and solids, e.g., a small portion of the feed or various suitable meals including alfalfa, soybean, cottonseed oil, linseed oil, corncob, corn, molasses, urea and bone, and mineral mixes.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I, or a prodrug thereof, or a geometric or optical isomer thereof, or a pharmaceutically acceptable salt of such compound, prodrug, or isomer, and a second compound as described above. The kit comprises a container for containing the separate compositions such as a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . Second Week, Monday, Tuesday, . . . " etc. Other variations of memory aids will be readily apparent. A "daily dose" can be a single tablet or capsule or several tablets or capsules to be taken on a given day. Also, a daily dose of a compound of Formula I, or a prodrug thereof, or a geometric or optical isomer thereof, or a pharmaceutically acceptable salt of such compound, prodrug or isomer, can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Utility of the compounds of Formula I, or the isomers thereof, or the pharmaceutically acceptable salts of such compounds, or isomers thereof, can be evidenced by activity in at least one of the two assays described below.

Assay 1

Oxygen Consumption

As would be appreciated by those skilled in the relevant art, during increased energy expenditure, animals generally consume more oxygen. In addition, metabolic fuels such as, for example, glucose and fatty acids, are oxidized to $CO_2$ and $H_2O$ with the concomitant evolution of heat, commonly referred to in the art as thermogenesis. Thus, the measurement of oxygen consumption in animals, including humans and companion animals, is an indirect measure of thermogenesis. Indirect calorimetry is commonly used in animals, e.g., humans, by those skilled in the relevant art to measure such energy expenditures.

Those skilled in the art understand that increased energy expenditure and the concomitant burning of metabolic fuels resulting in the production of heat may be efficacious with respect to the treatment of, e.g., obesity. As is well known by those skilled in the art, thyroid hormones affect cardiac functioning, for example, by causing an increase in the heart rate and, accordingly, an increase in oxygen consumption with concomitant heat production.

The ability of the compounds, isomers thereof, and pharmaceutically acceptable salts of said compounds and isomers of this invention to generate a thermogenic response may be demonstrated according to the following protocol.

A. Experimental

This in vivo screen is designed to evaluate the efficacy and cardiac effects of compounds that are tissue-selective thyroid hormone agonists. The efficacy endpoints measured are whole body oxygen consumption and the activity of liver mitochondrial alpha-glycerophosphate dehydrogenase ("mGPDH"). The cardiac endpoints that are measured are heart weight and heart mGPDH activity. The protocol involves: (a) dosing fatty Zucker rats for about 6 days, (b) measuring oxygen consumption and (c) harvesting tissue for preparation of mitochondria and subsequent assaying of enzyme activity thereby.

B. Preparation of Rats

Male fatty Zucker rats having a body weight range of from about 400 g to about 500 g are housed for from about 3 to about 7 days in individual cages under standard laboratory conditions prior to the initiation of the study.

A compound of Formula I, or an isomer thereof, or a pharmaceutically acceptable salt of such compound or isomer, vehicle or $T_3$ sodium salt, is administered by oral gavage as a single daily dose given between about 3 p.m. to about 6 p.m. for about 6 days. A compound of Formula I, or an isomer thereof, or a pharmaceutically acceptable salt of such compound or isomer, or $T_3$ sodium salt is dissolved in a suitably small volume of about 1N NaOH and then brought up to a suitable volume with about 0.01N NaOH containing about 0.25% of methyl cellulose (10:1, 0.01N NaOH/MC:1N NaOH). The dosing volume is about 1 ml.

C. Oxygen Consumption

About 1 day after the last dose of the compound is administered, oxygen consumption is measured using an open circuit, indirect calorimeter (Oxymax, Columbus Instruments, Columbus, Ohio 43204). The Oxymax gas sensors are calibrated with $N_2$ gas and a gas mixture (about 0.5% of $CO_2$, about 20.5% of $O_2$, about 79% of $N_2$) before each experiment.

The subject rats are removed from their home cages and their body weights recorded. The rats are placed into the sealed chambers (43×43×10 cm) of the Oxymax, the chambers are placed in the activity monitors, and the air flow rate through the chambers is then set at from about 1.6 L/min to about 1.7 L/min.

The Oxymax software then calculates the oxygen consumption (mL/kg/h) by the rats based on the flow rate of air through the chambers and the difference in oxygen content at the inlet and output ports. The activity monitors have 15 infrared light beams spaced about one inch apart on each axis, and ambulatory activity is recorded when two consecutive beams are broken, and the results are recorded as counts.

Oxygen consumption and ambulatory activity are measured about every 10 min for from about 5 h to about 6.5 h. Resting oxygen consumption is calculated on individual rats by averaging the values excluding the first 5 values and the values obtained during time periods where ambulatory activity exceeds about 100 counts.

Assay 2

Binding to Thyroid Hormone Receptors

The ability of a compound of Formula I, or an isomer thereof, or a pharmaceutically acceptable salt of such compound or isomer, ("the test thyromimetic compounds"), to bind to thyroid hormone receptors can be demonstrated in the following protocol.

A. Preparation of Insect Cell Nuclear Extracts

High Five cell pellets (BTI-TN-5B1-4, catalogue number B855-02, Invitrogen®, Carlsbad, Calif.) obtained about 48 h after infection with baculovirus (GibcoBRL®, Gaithersburg, Md.) expressing either human TRα or TRβ were suspended in ice cold Sample Buffer (10 mM Tris, pH 8.0; 1 mM $MgCl_2$; 1 mM DTT; 0.05% Tween 20; 1 mM 4-(2-aminoethyl)-benzenesulfonylfluoride; 25 µg/mL leupeptin). After about 10 min incubation on ice, the suspension was homogenized by 20 strokes with a Dounce homogenizer (VWR® Scientific Products, West Chester, Pa.) and centrifuged at 800×g for about 15 min at 4° C. The pellet (nuclei) was suspended in a hypertonic buffer (0.4 M KCl; 10 mM Tris, pH 8.0; 1 mM $MgCl_2$; 1 mM DTT; 0.05% Tween 20) and incubated for about 30 min on ice. The suspension was centrifuged at 100,000×g for about 30 min at 4° C. The supernatant (nuclear extract) was stored in 0.5 mL aliquots at −80° C.

B. Binding Assay

Competition binding assays to measure the interaction of the test thyromimetic compounds with thyroid hormone receptor α1 and β1 (TRα and TRβ) are carried out according to the following protocol.

Solutions of test thyromimetic compounds (final compound concentration of 20 mM) are prepared using 100% DMSO as a solvent. Each compound is serially diluted in an assay buffer (5 mM Tris-HCl, pH 8.0; 50 mM NaCl; 2 mM EDTA; 10% (v/v) glycerol; 1 mM DTT, "assay buffer") containing 0.4 nM $^{125}$I-$T_3$ (specific activity of about 220 Ci/mmol) to yield solutions that varied in compound concentration from about 10 µM to about 0.1 nM.

High Five insect cell nuclear extract containing either TRα or TRβ is diluted to a total protein concentration of 0.0075 mg/mL using the assay buffer as diluent.

One volume (100 µL) of each thyromimetic compound dilution (containing 0.4 nM $^{125}$I-T3) is combined with an equal volume (100 µL) of diluted nuclear extract containing TRα1 or TRβ1 and incubated at RT for about 90 min. 150 µL sample of the binding reaction is removed and placed into a 96-well filter plate (Millipore®, Bedford, Mass.) that had been pre-washed with ice-cold assay buffer. The plate is subjected to vacuum filtration using a filtration manifold (Millipore®). Each well is washed five times by the addition of 200 µL of ice-cold assay buffer and subsequent vacuum filtration. The plate is removed from the vacuum filtration manifold, the bottom of the plate is briefly dried on paper towels, then 25 µL of Wallac® (EG&G Wallac®, Gaithersburg, Md.) Optiphase Supermix scintillation cocktail is added to each well and the top of the plate is covered with plastic sealing tape (Microplate Press-on Adhesive Sealing Film, Packard® Instrument Co., Inc., Downers Grove, Ill.) and the radioactivity is quantitated using a Wallac® Microbeta 96-Well plate scintillation counter.

The following EXAMPLES are provided solely for the purposes of illustration and do not limit the invention which is defined by the claims.

EXAMPLE 1

N-{3,5-Dichloro-4-[4-hydroxy-3-(pyrrolidine-1-sulfonyl)-phenoxy]-phenyl}-oxamic acid Step A 2',6'-Dichloro-4-methoxy-4'-nitrodiphenyl ether was prepared by coupling of 2,6-dichloro-4-nitrophenol with (4,4'- dimethoxydiphenyl)iodonium tetrafluoroborate in the presence of copper powder and TEA according to the procedure described in the *J. Med. Chem.*, 38: 695–707(1995).

Step B

A solution of neat 2',6'-dichloro-4-methoxy-4'-nitrodiphenyl ether (500 mg, 1.6 mmol) at 0° C. was treated with chlorosulfonic acid (877 mL, 7.5 mmol) and the reaction mixture became immediately dark brown. The mixture was stirred for 5 min at 0° C. and allowed to warm to RT. After stirring for 30 min at RT, the reaction mixture was slowly dropped into 100 mL of ice water with stirring. The brown precipitate was extracted with ethyl acetate (3×75 mL). The combined organic extracts were washed with sodium bicarbonate (1×100 mL), water (1×100 mL), dried and concentrated to give a brown solid. The crude product was used in the next step without further purification. NMR (400 MHz, CDCl$_3$) d 8.32 (s, 2H), 7.40 (d, 1H), 7.20–7.25 (dd, 1H), 7.09 (d, 1H), 4.04 (s, 3H). MS Calc.: 410.9, Found: 392.1 [M−1 for 5-(2,6-dichloro-4-nitrophenoxy)-2-methoxy-benzenesulfonic acid].

Step C

To a solution of 5-(2,6-dichloro-4-nitro-phenoxy)-2-methoxy-benzenesulfonyl chloride (200 mg, 0.48 mmol) in 5 mL of CH$_2$Cl$_2$ at RT was added pyrrolidine (85 mL, 1.0 mmol). After stirring for 2 h at RT, the reaction mixture was quenched with 1N HCl (5 mL) and extracted with CH$_2$Cl$_2$ (3×10 mL). The combined extracts were washed with 1N HCl (3×5 mL), saturated aqueous NaHCO$_3$ (2×5 mL), dried and concentrated. The residue was purified by preparative TLC (Hexane: EtOAC=2:1) to afford a white solid. NMR (400 MHz, CDCl$_3$) d 8.30 (s, 2H), 7.39 (d, 1H), 7.02–7.05 (dd, 1H), 6.95–6.98 (d, 1H), 3.91 (s, 3H), 3.35–3.38 (m, 4H), 1.82–1.87 (m, 4H). MS Calc.: 446.0, Found: 447.0 (M+1).

Step D

To a solution of 1-[5-(2,6-dichloro-4-nitro-phenoxy)-2-methoxy-benzene-sulfonyl]-pyrrolidine (178.5 mg, 0.4 mmol) in 8 mL of chloroform at RT was added dropwise boron tribromide (1N in CH$_2$Cl$_2$, 2.4 mL, 2.4 mmol). After stirring for 16 h at RT, the reaction mixture was quenched with 10 mL of water. The mixture was stirred for 1 h at RT, extracted with CH$_2$Cl$_2$ (1×5 mL) and EtOAc (2×10 mL). The combined organic extracts were dried and concentrated. The product was used in the next step without further purification. NMR (400 MHz, CD$_3$OD) d 8.31 (s, 2H), 7.09 (d, 1H), 6.96–7.02 (m, 2H), 3.28–3.31 (m, 4H), 1.79–1.82 (m, 4H). MS Calc.: 432.0, Found: 431.1 (M−1).

Step E

A mixture of 4-(2,6-dichloro-4-nitro-phenoxy)-2-(pyrrolidine-1-sulfonyl)-phenol (166 mg, 0.38 mmol) and catalyst about 10% Pd/C (17 mg) in a mixture of EtOAc (5 mL) and MeOH (10 mL) was hydrogenated under 40 psi at RT for 1 h. The solution was filtered through Celite® and concentrated to give a brown solid. The product was used in the next step without further purification. NMR (400 MHz, CDCl$_3$) d 8.34 (s, 2H), 6.96–7.22 (broad S+m, 5H), 3.19 (m, 4H), 1.73 (m, 4H), MS Calc.: 402, Found: 401.1 (M−1).

Step F

A mixture of 4-(4-amino-2,6-dichloro-phenoxy)-2-(pyrrolidine-1-sulfonyl)-phenol (154 mg, 0.38 mmol) and diethyl oxalate (1.49 g, 10.2 mmol) was stirred at 120° C. for 4 h. The excess diethyl oxalate was distilled off in vacuo. The residue was purified by preparative TLC (0.5% MeOH in CH$_2$Cl$_2$) to give an off-white solid. NMR (400 MHz, CDCl$_3$) d 9.06 (s, 1H), 8.60 (s, 1H), 7.76 (s, 2H), 7.03–7.06 (dd, 1H), 6.96–6.98 (d, 1H), 6.90 (d, 1H), 4.36–4.40 (q, 2H), 3.18–3.21 (m, 4H), 1.74–1.78 (m, 4H), 1.39 (t, 3H). MS Calc.: 502, Found: 501.1 (M−1).

Step G

A solution of N-{3,5-dichloro-4-[4-hydroxy-3-(pyrrolidine-1-sulfonyl)-phenoxy]-phenyl}-oxamic acid ethyl ester (10 mg, 0.02 mmol) in a mixture of H$_2$O (0.5 mL) and MeOH (0.5 mL) was added 2 drops of 3N KOH. The reaction mixture was stirred at RT for 2 h, acidified with 1N HCl and extracted with EtOAc (4×5 mL). The combined organic extracts were dried and concentrated to afford the title compound as an off-white solid. NMR (400 MHz, CD$_3$OD) d 7.96 (s, 2H), 7.02–7.06 (m, 2H), 6.95–6.98 (d, 1H), 3.28–3.31 (m, 4H), 1.78–1.81 (m, 4H). MS Calc.: 474.3 Found: 473.1 (M−1).

Using the appropriate starting materials, EXAMPLES 1-1 to 1-57 were prepared in an analogous manner to that described in EXAMPLE 1.

EXAMPLE 1-1

N-[4-(3-Cyclopropylsulfamoyl-4-hydroxy-phenoxy)-3,5-dimethyl-phenyl]-oxamic acid ethyl ester, MS Calc.: 448.5 Found: 447.3 (M−1).

EXAMPLE 1-2

N-[4-(4-Hydroxy-3-methylsulfamoyl-phenoxy)-3,5-dimethyl-phenyl]-oxamic acid ethyl ester, MS Calc.: 422.5 Found: 421.3 (M−1).

EXAMPLE 1-3

N-{4-[3-(4-Fluoro-phenylsulfamoyl)-4-hydroxy-phenoxy]-3,5-dimethyl-phenyl}-oxamic acid ethyl ester, MS Calc.: 502.5 Found: 501.1 (M−1).

EXAMPLE 1-4

N-[4-(3-Dimethylsulfamoyl-4-hydroxy-phenoxy)-3,5-dimethyl-phenyl]-oxamic acid ethyl ester, MS Calc.: 436.5 Found: 435.3 (M−1).

EXAMPLE 1-5

N-{4-[3-(Cyclopropyl-methyl-sulfamoyl)-4-hydroxy-phenoxy]-3,5-dimethyl-phenyl}-oxamic acid ethyl ester, MS Calc.: 462.5 Found: 461.2 (M−1).

EXAMPLE 1-6

N-{4-[3-(Cyclobutyl-methyl-sulfamoyl)-4-hydroxy-phenoxy]-3,5-dimethyl-phenyl}- oxamic acid ethyl ester, MS Calc.: 476.6 Found: 475.3 (M−1).

EXAMPLE 1-7

N-[4-(3-Cyclobutylsulfamoyl-4-hydroxy-phenoxy)-3,5-dimethyl-phenyl]-oxamic acid ethyl ester, MS Calc.: 462.5 Found: 461.2 (M−1).

EXAMPLE 1-8

N-[4-(3-Cyclopentylsulfamoyl-4-hydroxy-phenoxy)-3,5-dimethyl-phenyl]-oxamic acid ethyl ester, MS Calc.: 476.6 Found: 475.3 (M−1).

EXAMPLE 1-9

N-{4-[4-Hydroxy-3-(pyrrolidine-1-sulfonyl)-phenoxy]-3,5-dimethyl-phenyl}-oxamic acid ethyl ester, MS Calc.: 462.5 Found: 461.3 (M−1).

EXAMPLE 1-10

N-{4-[4-Hydroxy-3-(piperidine-1-sulfonyl)-phenoxy]-3,5-dimethyl-phenyl}-oxamic acid ethyl ester, MS Calc.: 476.6 Found: 475.2 (M−1).

EXAMPLE 1-11

N-[4-(3-Cyclohexylsulfamoyl-4-hydroxy-phenoxy)-3,5-dimethyl-phenyl]-oxamic acid ethyl ester, MS Calc.: 490.6 Found: 489.3 (M−1).

EXAMPLE 1-12

N-[4-(4-Hydroxy-3-propylsulfamoyl-phenoxy)-3,5-dimethyl-phenyl]-oxamic acid ethyl ester, MS Calc.: 450.5 Found: 449.3 (M−1).

EXAMPLE 1-13

N-[4-(3-Butylsulfamoyl-4-hydroxy-phenoxy)-3,5-dimethyl-phenyl]-oxamic acid ethyl ester, MS Calc.: 464.5 Found: 463.3 (M−1).

EXAMPLE 1-14

N-{4-[3-(Cyclopropyl-methyl-sulfamoyl)-4-hydroxy-phenoxy]-3,5-dimethyl-phenyl}-oxamic acid, MS Calc.: 434.5 Found: 433.3 (M−1).

EXAMPLE 1-15

N-{4-[3-(Cyclobutyl-methyl-sulfamoyl)-4-hydroxy-phenoxy]-3,5-dimethyl-phenyl}-oxamic acid, MS Calc.: 448.5 Found: 447.3 (M−1).

EXAMPLE 1-16

N-[4-(3-Cyclopropylsulfamoyl-4-hydroxy-phenoxy)-3,5-dimethyl-phenyl]-oxamic acid, MS Calc.: 420.4 Found: 419.3 (M−1).

EXAMPLE 1-17

N-[4-(3-Cyclobutylsulfamoyl-4-hydroxy-phenoxy)-3,5-dimethyl-phenyl]-oxamic acid, MS Calc.: 434.5 Found: 433.2 (M−1).

EXAMPLE 1-18

N-[3-Chloro-4-(3-cyclopropylsulfamoyl-4-hydroxy-phenoxy)-5-methyl-phenyl]-oxamic acid ethyl ester, MS Calc.: 468.1 Found: 466.5 (M−1).

EXAMPLE 1-19

N-[3-Chloro-4-(3-cyclobutylsulfamoyl-4-hydroxy-phenoxy)-5-methyl-phenyl]-oxamic acid ethyl ester, MS Calc.: 482.1 Found: 480.4 (M−1).

EXAMPLE 1-20

N-[3-Chloro-4-(3-cyclopentylsulfamoyl-4-hydroxy-phenoxy)-5-methyl-phenyl]-oxamic acid ethyl ester, MS Calc.: 496.2 Found: 494.9 (M−1).

EXAMPLE 1-21

N-[3-Chloro-4-(3-cyclohexylsulfamoyl-4-hydroxy-phenoxy)-5-methyl-phenyl]-oxamic acid ethyl ester, MS Calc.: 510.2 Found: 508.8 (M−1).

EXAMPLE 1-22

N-[3-Chloro-4-(4-hydroxy-3-sulfamoyl-phenoxy)-5-methyl-phenyl]-oxamic acid ethyl ester, MS Calc.: 428.1 Found: 426.7 (M−1).

EXAMPLE 1-23

N-{3-Chloro-4-[4-hydroxy-3-(piperidine-1-sulfonyl)-phenoxy]-5-methyl-phenyl}- oxamic acid ethyl ester, MS Calc.: 496.1 Found: 495.1 (M−1).

EXAMPLE 1-24

N-{3-Chloro-4-[3-(4-fluoro-phenylsulfamoyl)-4-hydroxy-phenoxy]-5-methyl-phenyl}-oxamic acid ethyl ester, MS Calc.: 522.1 Found: 520.4 (M−1).

EXAMPLE 1-25

N-[3-Chloro-4-(3-dimethylsulfamoyl-4-hydroxy-phenoxy)-5-methyl-phenyl]-oxamic acid ethyl ester, MS Calc.: 456.1 Found: 457.3 (M+1).

EXAMPLE 1-26

N-[3-Chloro-4-(4-hydroxy-3-methylsulfamoyl-phenoxy)-5-methyl-phenyl]-oxamic acid ethyl ester, MS Calc.: 442.1 Found: 441.2 (M−1).

EXAMPLE 1-27

N-[3-Chloro-4-(4-hydroxy-3-propylsulfamoyl-phenoxy)-5-methyl-phenyl]-oxamic acid ethyl ester, MS Calc.: 470.1 Found: 469.2 (M−1).

EXAMPLE 1-28

N-[3-Chloro-4-(4-hydroxy-3-pentylsulfamoyl-phenoxy)-5-methyl-phenyl]-oxamic acid ethyl ester, MS Calc.: 498.2 Found: 497.2 (M−1).

EXAMPLE 1-29

N-[3-Chloro-4-(3-hexylsulfamoyl-4-hydroxy-phenoxy)-5-methyl-phenyl]-oxamic acid ethyl ester, MS Calc.: 512.2 Found: 511.2 (M−1).

EXAMPLE 1-30

N-[3-Chloro-4-(4-hydroxy-3-octylsulfamoyl-phenoxy)-5-methyl-phenyl]-oxamic acid ethyl ester, MS Calc.: 540.3 Found: 539.2 (M−1).

EXAMPLE 1-31

N-[3-Chloro-4-(3-decylsulfamoyl-4-hydroxy-phenoxy)-5-methyl-phenyl]-oxamic acid ethyl ester, MS Calc.: 568.3 Found: 567.3 (M−1).

EXAMPLE 1-32

N-[4-(3-Butylsulfamoyl-4-hydroxy-phenoxy)-3-chloro-5-methyl-phenyl]-oxamic acid ethyl ester, MS Calc.: 484.2 Found: 483.2 (M−1).

EXAMPLE 1-33

N-{3-Chloro-4-[3-(ethyl-methyl-sulfamoyl)-4-hydroxy-phenoxy]-5-methyl-phenyl}-oxamic acid ethyl ester, MS Calc.: 470.1 Found: 469.2 (M−1).

EXAMPLE 1-34

N-{3-Chloro4-[4-hydroxy-3-(methyl-propyl-sulfamoyl)-phenoxy]-5-methyl-phenyl}-oxamic acid ethyl ester, MS Calc.: 484.2 Found: 483.2 (M−1).

EXAMPLE 1-35

N-{4-[3-(Butyl-methyl-sulfamoyl)-4-hydroxy-phenoxy]-3-chloro-5-methyl-phenyl}-oxamic acid ethyl ester, MS Calc.: 498.2 Found: 497.2 (M−1).

EXAMPLE 1-36

N-{3-Chloro-4-[4-hydroxy-3-(morpholine-4-sulfonyl)-phenoxy]-5-methyl-phenyl}-oxamic acid ethyl ester, MS Calc.: 498.1 Found: 497.2 (M−1).

EXAMPLE 1-37

N-{3-Chloro-4-[3-(cyclopropylmethyl-sulfamoyl)-4-hydroxy-phenoxy]-5-methyl-phenyl}-oxamic acid ethyl ester, MS Calc.: 482.1 Found: 481.2 (M−1).

EXAMPLE 1-38

N-{3-Chloro-4-[4-hydroxy-3-(2-hydroxy-ethylsulfamoyl)-phenoxy]-5-methyl-phenyl}-oxamic acid ethyl ester, MS Calc.: 472.1 Found: 471.2 (M−1).

EXAMPLE 1-39

N-[3-Chloro-4-(3-cyclopropylsulfamoyl-4-hydroxy-phenoxy)-5-methyl-phenyl]-oxamic acid isopropyl ester, MS Calc.: 482.1 Found: 481.2 (M−1).

EXAMPLE 1-40

N-[3-Chloro-4-(3-cyclopropylsulfamoyl-4-hydroxy-phenoxy)-5-methyl-phenyl]-oxamic acid, MS Calc.: 440.1 Found: 439.2 (M−1).

EXAMPLE 1-41

N-[3-Chloro-4-(3-cyclobutylsulfamoyl-4-hydroxy-phenoxy)-5-methyl-phenyl]-oxamic acid, MS Calc.: 454.1 Found: 452.8 (M−1).

EXAMPLE 1-42

N-[3-Chloro-4-(3-cyclopentylsulfamoyl-4-hydroxy-phenoxy)-5-methyl-phenyl]-oxamic acid, MS Calc.: 468.1 Found: 466.9 (M−1).

EXAMPLE 1-43

N-[3-Chloro-4-(3-cyclohexylsulfamoyl-4-hydroxy-phenoxy)-5-methyl-phenyl]-oxamic acid, MS Calc.: 482.1 Found: 481.0 (M−1).

EXAMPLE 1-44

N-[3-Chloro-4-(4-hydroxy-3-sulfamoyl-phenoxy)-5-methyl-phenyl]-oxamic acid, MS Calc.: 400.0 Found: 398.9 (M−1).

EXAMPLE 1-45

N-{3-Chloro-4-[3-(4-fluoro-phenylsulfamoyl)-4-hydroxy-phenoxy]-5-methyl-phenyl}-oxamic acid, MS Calc.: 494.1 Found: 493.1 (M−1).

EXAMPLE 1-46

N-[3-Chloro-4-(4-hydroxy-3-propylsulfamoyl-phenoxy)-5-methyl-phenyl]-oxamic acid, MS Calc.: 442.1 Found: 441.2 (M−1).

EXAMPLE 1-47

N-[4-(3-Butylsulfamoyl-4-hydroxy-phenoxy)-3-chloro-5-methyl-phenyl]-oxamic acid, MS Calc.: 456.1 Found: 455.1 (M−1).

EXAMPLE 1-48

N-{3-Chloro-4-[4-hydroxy-3-(morpholine-4-sulfonyl)-phenoxy]-5-methyl-phenyl}-oxamic acid, MS Calc.: 470.1 Found: 469.2 (M−1).

EXAMPLE 1-49

N-{3,5-Dichloro-4-[4-hydroxy-3-(pyrrolidine-1-sulfonyl)-phenoxy]-phenyl}-oxamic acid ethyl ester, MS Calc.: 502.0 Found: 501.1 (M−1).

EXAMPLE 1-50

N-{3,5-Dichloro-4-[3-(3,4-dihydro-1H-isoquinoline-2-sulfonyl)-4-hydroxy-phenoxy]-phenyl}-oxamic acid ethyl ester, MS Calc.: 564.1 Found: 562.8 (M−1).

EXAMPLE 1-51

N-[3,5-Dichloro-4-(3-cyclobutylsulfamoyl-4-hydroxy-phenoxy)-phenyl]-oxamic acid ethyl ester, MS Calc.: 502.0 Found: 500.3 (M−1).

EXAMPLE 1-52

N-{4-[3-(Bicyclo[2.2.1]hept-2-ylsulfamoyl)-4-hydroxy-phenoxy]-3,5-dichloro-phenyl}-oxamic acid ethyl ester, MS Calc.: 542.0 Found: 540.6 (M−1).

EXAMPLE 1-53

N-(3,5-Dichloro-4-{4-hydroxy-3-[(thiophen-2-ylmethyl)-sulfamoyl]-phenoxy}-phenyl)-oxamic acid ethyl ester, MS Calc.: 544.0 Found: 542.3 (M−1).

EXAMPLE 1-54

N-[3,5-Dichloro-4-(4-hydroxy-3-isopropylsulfamoyl-phenoxy)-phenyl]-oxamic acid ethyl ester, MS Calc.: 490.0 Found: 488.9 (M−1).

EXAMPLE 1-55

N-[3,5-Dichloro4-(3-dimethylsulfamoyl-4-hydroxy-phenoxy)-phenyl]-oxamic acid ethyl ester, MS Calc.: 476.1 Found: 475.1 (M−1).

EXAMPLE 1-56

N-{3,5-Dichloro-4-[4-hydroxy-3-(pyrrolidine-1-sulfonyl)-phenoxy]-phenyl}-oxamic acid, MS Calc.: 474.1 Found: 473.1 (M−1).

EXAMPLE 1-57

N-[3,5-Dichloro-4-(4-hydroxy-3-isopropylsulfamoyl-phenoxy)-phenyl]-oxamic acid, MS Calc.: 462.0 Found: 461.1 (M−1).

EXAMPLE 2

N-{3,5-Dichloro-4-[3-(3,3-dimethyl-piperidine-1-carbonyl)-4-hydroxy-phenoxy]-phenyl}-oxamic acid ethyl ester Step A A mixture of 2′, 6′-dichloro-4-methoxy-4′-nitrodiphenyl ether (5.0 g, 16 mmol), TFA (50 mL) and hexamethylene-tetramine (3.35 g, 24 mmol) was stirred at 70° C. for 3 h to give a yellow solution. TFA was removed by rotavap to give a viscous yellow oil which was diluted with H$_2$O (100 mL)

and stirred at RT for 0.5 h. Saturated aqueous $NaHCO_3$ (300 mL) was added and the mixture was extracted with EtOAc (3×100 mL). The combined organic extracts are washed with brine (200 mL), dried and concentrated to give a yellow solid. MS Calc.: 341.0 Found: 340.4 (M−1).

Step B

To a solution of 5-(2,6-dichloro-4-nitro-phenoxy)-2-methoxy-benzaldehyde (1.0 g, 2.9 mmol) in acetone (30 mL) was added slowly Jones reagent (3.0 mL). The resulting solution was stirred at RT for 1 h and quenched with isopropanol (4 mL). The solid was removed by filtration through Celite®. The bluish solution was concentrated to give yellow solid with blue supernatant. The solid was dissolved in EtOAc and dried over $Na_2SO_4$, filtered and concentrated. The resulting yellow oily solid was partially dissolved in EtOAc (25 mL) and extracted with saturated aqueous $NaHCO_3$ (5×75 mL). The combined aqueous extracts were acidified with 2N HCl, extracted with EtOAc (4×100 mL), dried and concentrated to give a yellow solid. MS Calc.: 356.9 Found: 357.8 (M−1).

Step C

To a solution of 5-(2,6-dichloro-4-nitro-phenoxy)-2-methoxy-benzoic acid (0.81 g, 2.3 mmol) in chloroform (20 mL) at RT was added dropwise tribromide (1 N in $CH_2Cl_2$, 4.5 mL, 4.5 mmol). The resulting mixture was stirred at RT for 1 h and quenched with $H_2O$ (20 mL). After stirring at RT for 0.5 h, the aqueous phase was basified with saturated aqueous $NaHCO_3$ (30 mL). The organic phase was extracted with saturated aqueous $NaHCO_3$ (4×50 mL). The combined aqueous extracts were acidified with concentrated HCl to give a white precipitate which was extracted with EtOAc (4×100 mL). The combined organic extracts were dried and concentrated to give a yellow-white solid. MS Calc.: 342.9 Found: 341.8 (M−1).

Step D

To a solution of 5-(2,6-dichloro-4-nitro-phenoxy)-2-hydroxybenzoic acid (0.69 g, 2 mmol) in a mixture of EtOAc (4 mL) and MeOH (12 mL) was added 10% Pd/C (70 mg). The solution was hydrogenated under 40 psi of pressure at RT for 2 h then filtered through Celite®. The filtrate was concentrated. The product was used in the next step without further purification. MS Calc.: 312.9 Found: 311.9 (M−1).

Step E

A mixture of 5-(2,6-dichloro-4-amino-phenoxy)-2-hydroxybenzoic acid (0.63 g, 2 mmol) and diethyl oxalate (4.4 g, 30 mmol) was stirred at 140° C. for 3 h. The excess diethyl oxalate was removed under vacuum to give a brown oily solid which was triturated with hexanes to remove the remaining diethyl oxalate. The tan solid was collected by filtration and washed with $CH_2Cl_2$/hexanes (5% $CH_2Cl_2$ in hexanes). The product was used in the next step without further purification. MS Calc.: 413.0 Found: 411.8 (M−1).

Step F

To a solution of 5-[2,6-dichloro-4-(ethoxyoxalyl-amino)-phenoxy]-2-hydroxy-benzoic acid (29 mg, 0.07 mmol) in THF at RT was added thionyl chloride (25 mg, 0.21 mmol). The resulting mixture was stirred at 60° C. for 1 h and concentrated in vacuum to give the acid chloride as a tan solid. The acid chloride was dissolved in chloroform (0.5 mL) and to which was added diisopropylethylamine (18 mg, about 0.14 mmol) and 3,3-dimethylpiperidine (9.4 mg, 0.083 mmol). The resulting mixture was stirred at RT for 17 h and concentrated. The crude product was purified by preparative TLC (6% acetone in $CH_2Cl_2$) to give the title compound as a white solid. MS Calc.: 509.4 Found: 507.2 (M−1).

Using the appropriate starting materials, EXAMPLES 2-1 to 2-109 were prepared in an analogous manner to that described in EXAMPLE 2.

EXAMPLE 2-1

N-{4-[3-(3,4-Dihydro-1H-isoquinoline-2-carbonyl)-4-hydroxy-phenoxy]-3,5-dimethyl-phenyl}-oxamic acid ethyl ester, MS Calc.: 488.6 Found: 486.6 (M−1).

EXAMPLE 2-2

N-{4-[3-(3,4-Dihydro-2H-quinoline-1-carbonyl)-4-hydroxy-phenoxy]-3,5-dimethyl-phenyl}-oxamic acid ethyl ester, MS Calc.: 488.6 Found: 486.5 (M−1).

EXAMPLE 2-3

N-{4-[3-(2,3-Dihydro-indole-1-carbonyl)-4-hydroxy-phenoxy]-3,5-dimethyl-phenyl}-oxamic acid ethyl ester, MS Calc.: 474.5 Found: 473.3 (M−1).

EXAMPLE 2-4

N-{4-[3-(3,3-Dimethyl-piperidine-1-carbonyl)-4-hydroxy-phenoxy]-3,5-dimethyl-phenyl}-oxamic acid ethyl ester, MS Calc.: 468.6 Found: 466.7 (M−1).

EXAMPLE 2-5

N-{4-[4-Hydroxy-3-(3-methyl-3-phenyl-piperidine-1-carbonyl)-phenoxy]-3,5-dimethyl-phenyl}-oxamic acid ethyl ester, MS Calc.: 530.6 Found: 528.7 (M−1).

EXAMPLE 2-6

N-{4-[3-(Azepane-1-carbonyl)-4-hydroxy-phenoxy]-3,5-dimethyl-phenyl}-oxamic acid ethyl ester, MS Calc.: 454.5 Found: 453.2 (M−1).

EXAMPLE 2-7

N-{4-[4-Hydroxy-3-(1-naphthalen-1-yl-(1R)-ethylcarbamoyl)-phenoxy]-3,5-dimethyl-phenyl}-oxamic acid ethyl ester, MS Calc.: 526.6 Found: 525.2 (M−1).

EXAMPLE 2-8

N-{4-[4-Hydroxy-3-(1-phenyl-(1R)-ethylcarbamoyl)-phenoxy]-3,5-dimethyl-phenyl}-oxamic acid ethyl ester, MS Calc.: 476.5 Found: 475.2 (M−1).

EXAMPLE 2-9

N-{4-[3-(Bicyclo[2.2.1]hept-2-ylcarbamoyl)-4-hydroxy-phenoxy]-3,5-dimethyl-phenyl}-oxamic acid ethyl ester, MS Calc.: 466.5 Found: 465.2 (M−1).

EXAMPLE 2-10

N-{4-[3-(4-Chloro-benzylcarbamoyl)-4-hydroxy-phenoxy]-3,5-dimethyl-phenyl}-oxamic acid ethyl ester, MS Calc.: 497.0 Found: 495.2 (M−1).

EXAMPLE 2-11

N-{4-[3-(1-Cyclohexyl-(1R)-ethylcarbamoyl)-4-hydroxy-phenoxy]3,5-dimethyl-phenyl}-oxamic acid ethyl ester, MS Calc.: 482.6 Found: 483.3 (M+1).

EXAMPLE 2-12

N-{4-[4-Hydroxy-3-(1-naphthalen-2-yl-(1R)-ethylcarbamoyl)-phenoxy]-3,5-dimethyl-phenyl}-oxamic acid ethyl ester, MS Calc.: 526.6 Found: 525.4 (M−1).

EXAMPLE 2-13

N-[4-(3-Cyclobutylcarbamoyl-4-hydroxy-phenoxy)-3,5-dimethyl-phenyl]-oxamic acid ethyl ester, MS Calc.: 426.5 Found: 425.3 (M−1).

EXAMPLE 2-14

N-[4-(3-Cyclopentylcarbamoyl-4-hydroxy-phenoxy)-3,5-dimethyl-phenyl]-oxamic acid ethyl ester, MS Calc.: 440.5 Found: 439.3 (M−1).

EXAMPLE 2-15

N-{4-[4-Hydroxy-3-(1-isopropyl-2-methyl-propylcarbamoyl)-phenoxy]-3,5-dimethyl-phenyl}-oxamic acid ethyl ester, MS Calc.: 470.6 Found: 469.2 (M−1).

EXAMPLE 2-16

N-{4-[4-Hydroxy-3-(pyrrolidine-1-carbonyl)-phenoxy]-3,5-dimethyl-phenyl}-oxamic acid ethyl ester, MS Calc.: 426.5 Found: 425.3 (M−1).

EXAMPLE 2-17

N-{4-[4-Hydroxy-3-(morpholine-4-carbonyl)-phenoxy]-3,5-dimethyl-phenyl}-oxamic acid ethyl ester, MS Calc.: 442.5 Found: 441.3 (M−1).

EXAMPLE 2-18

N-{4-[4-Hydroxy-3-(1-naphthalen-1-yl-(1R)ethylcarbamoyl)-phenoxy]-3,5-dimethyl-phenyl}-oxamic acid, MS Calc.: 498.5 Found: 497.2 (M−1).

EXAMPLE 2-19

N-{4-[4-Hydroxy-3-(1-phenyl-(1R)ethylcarbamoyl)-phenoxy]-3,5-dimethyl-phenyl}-oxamic acid, MS Calc.: 448.5 Found: 447.3 (M−1).

EXAMPLE 2-20

N-{4-[3-(Cyclopropyl-methyl-carbamoyl)-4-hydroxy-phenoxy]-3,5-dimethyl-pentyl}-oxamic acid, MS Calc.: 398.4 Found: 397.3 (M−1).

EXAMPLE 2-21

N-{4-[3-(Cyclobutyl-methyl-carbamoyl)-4-hydroxy-phenoxy]-3,5-dimethyl-phenyl}-oxamic acid, MS Calc.: 412.5 Found: 411.3 (M−1).

EXAMPLE 2-22

N-{4-[4-Hydroxy-3-(1-isopropyl-2-methyl-propylcarbamoyl)-phenoxy]-3,5-dimethyl-phenyl}-oxamic acid, MS Calc.: 442.5 Found: 441.3 (M−1).

EXAMPLE 2-23

N-{4-[3-(Cyclopentyl-methyl-carbamoyl)-4-hydroxy-phenoxy]-3,5-dimethyl-phenyl}-oxamic acid, MS Calc.: 426.5 Found: 425.3 (M−1).

EXAMPLE 2-24

N-{4-[3-(Cyclohexyl-methyl-carbamoyl)-4-hydroxy-phenoxy]-3,5-dimethyl-phenyl}-oxamic acid, MS Calc.: 440.5 Found: 439.3 (M−1).

EXAMPLE 2-25

N-{3-Chloro4-[4-hydroxy-3-(3-methyl-3-phenyl-piperidine-1-carbonyl)-phenoxy]-5-methyl-phenyl}-oxamic acid ethyl ester, MS Calc.: 551.0 Found: 549.2 (M−1).

EXAMPLE 2-26

N-{4-[3-(Azepane-1-carbonyl)-4-hydroxy-phenoxy]-3-chloro-5-methyl-phenyl}-oxamic acid ethyl ester, MS Calc.: 475.0 Found: 473.3 (M−1).

EXAMPLE 2-27

N-{3-Chloro-4-[3-(3,3-dimethyl-piperidine-1-carbonyl)-4-hydroxy-phenoxy]-5-methyl-phenyl}-oxamic acid ethyl ester, MS Calc.: 489.0 Found: 487.3 (M−1).

EXAMPLE 2-28

N-(3-Chloro-4-{4-hydroxy-3-[(thiophen-2-ylmethyl)-carbamoyl]-phenoxy}5-methyl-phenyl)-oxamic acid ethyl ester, MS Calc.: 489.0 Found: 487.2 (M−1).

EXAMPLE 2-29

N-{3-Chloro-4-[3-(2,3-dichloro-benzylcarbamoyl)-4-hydroxy-phenoxy]-5-methyl-phenyl}-oxamic acid ethyl ester, MS Calc.: 551.8 Found: 549.1 (M−1).

EXAMPLE 2-30

N-[3-Chloro-4-(3-cyclopropylcarbamoyl-4-hydroxy-phenoxy)-5-methyl-phenyl]-oxamic acid ethyl ester, MS Calc.: 432.9 Found: 431.2 (M−1).

EXAMPLE 2-31

N-{3-Chloro-4-[3-(2,3-dihydro-indole-1-carbonyl)-4-hydroxy-phenoxy]-methyl-phenyl}-oxamic acid ethyl ester, MS Calc.: 494.9 Found: 492.2 (M−1).

EXAMPLE 2-32

N-{3-Chloro-4-[3-(3,4-dihydro-2H-quinoline-1-carbonyl)-4-hydroxy-phenoxy]-5-methyl-phenyl}-oxamic acid ethyl ester, MS Calc.: 509.0 Found: 507.2 (M−1).

EXAMPLE 2-33

N-{3-Chloro-4-[3-(3,4-dihydro-1H-isoquinoline-2-carbonyl)-4-hydroxy-phenoxy]-5-methyl-phenyl-oxamic acid ethyl ester, MS Calc.: 509.0 Found: 507.3 (M−1).

EXAMPLE 2-34

N-{3-Chloro-4-[4-hydroxy-3-(indan-1-ylcarbamoyl)-phenoxy]-5-methyl-phenyl}-oxamic acid ethyl ester, MS Calc.: 509.0 Found: 507.3 (M−1).

EXAMPLE 2-35

N-{3-Chloro-4-[4-hydroxy-3-(indan-5-ylcarbamoyl)-phenoxy]-5-methyl-phenyl}-oxamic acid ethyl ester, MS Calc.: 509.0 Found: 507.2 (M−1).

EXAMPLE 2-36

N-{4-[3-(Bicyclo[2.2.1]hept-2-ylcarbamoyl)-4-hydroxy-phenoxy]-3-chloro-5-methyl-phenyl}-oxamic acid ethyl ester, MS Calc.: 487.0 Found: 485.1 (M−1).

EXAMPLE 2-37

N-{3-Chloro4-[3-(cyclohexylmethyl-carbamoyl)-4-hydroxy-phenoxy]-5-methyl-phenyl}-oxamic acid ethyl ester, MS Calc.: 489.0 Found: 487.3 (M−1).

EXAMPLE 2-38

N-{3-Chloro-4-[3-(1-cyclohexyl-(1R)ethylcarbamoyl)-4-hydroxy-phenoxy]-5-methyl-phenyl}-oxamic acid ethyl ester, MS Calc.: 503.0 Found: 501.3 (M−1).

EXAMPLE 2-39

N-{3-Chloro-4-[3-(1-cyclohexyl-(1S)ethylcarbamoyl)-4-hydroxy-phenoxy]-5-methyl-phenyl}-oxamic acid ethyl ester, MS Calc.: 503.0 Found: 501.4 (M−1).

EXAMPLE 2-40

N-{3-Chloro-4-[4-hydroxy-3-(piperidine-1-carbonyl)-phenoxy]-5-methyl-phenyl}-oxamic acid ethyl ester, MS Calc.: 460.9 Found: 459.3 (M−1).

EXAMPLE 2-41

N-{4-[3-(Azocane-1-carbonyl)-4-hydroxy-phenoxy]-3-chloro-5-methyl-phenyl}-oxamic acid ethyl ester, MS Calc.: 489.0 Found: 487.3 (M−1).

EXAMPLE 2-42

N-[3-Chloro-4-(3-cyclohexylcarbamoyl-4-hydroxy-phenoxy)-5-methyl-phenyl]-oxamic acid ethyl ester, MS Calc.: 475.0 Found: 473.3 (M−1).

EXAMPLE 2-43

N-{3-Chloro-4-[4-hydroxy-3-(1-phenyl-(1R)ethylcarbamoyl)-phenoxy]-5-methyl-phenyl}-oxamic acid ethyl ester, MS Calc.: 497.0 Found: 495.2 (M−1).

EXAMPLE 2-44

N-[3-Chloro-4-(4-hydroxy-3-propylcarbamoyl-phenoxy)-5-methyl-phenyl]-oxamic acid ethyl ester, MS Calc.: 434.9 Found: 433.2 (M−1).

EXAMPLE 2-45

N-[4-(3-Butylcarbamoyl-4-hydroxy-phenoxy)-3-chloro-5-methyl-phenyl]-oxamic acid ethyl ester, MS Calc.: 448.9 Found: 447.3 (M−1).

EXAMPLE 2-46

N-[3-Chloro-4-(4-hydroxy-3-pentylcarbamoyl-phenoxy)-5-methyl-phenyl]-oxamic acid ethyl ester, MS Calc.: 462.9 Found: 461.2 (M−1).

EXAMPLE 2-47

N-[3-Chloro-4-(3-hexylcarbamoyl-4-hydroxy-phenoxy)-5-methyl-phenyl]-oxamic acid ethyl ester, MS Calc.: 477.0 Found: 475.2 (M−1).

EXAMPLE 2-48

N-{3-Chloro-4-[3-(1,1-dimethyl-propylcarbamoyl)-4-hydroxy-phenoxy]-5-methyl-phenyl}-oxamic acid ethyl ester, MS Calc.: 462.9 Found: 461.2 (M−1).

EXAMPLE 2-49

N-[3-Chloro-4-(3-diisopropylcarbamoyl-4-hydroxy-phenoxy)-5-methyl-phenyl]-oxamic acid ethyl ester, MS Calc.: 477.0 Found: 475.3 (M−1).

EXAMPLE 2-50

N-{3-Chloro-4-[3-(2,2-dimethyl-propylcarbamoyl)-4-hydroxy-phenoxy]-5-methyl-phenyl}-oxamic acid ethyl ester, MS Calc.: 462.9 Found: 461.2 (M−1).

EXAMPLE 2-51

N-{3-Chloro-4-[3-(1,2-dimethyl-propylcarbamoyl)-4-hydroxy-phenoxy]-5-methyl-phenyl}-oxamic acid ethyl ester, MS Calc.: 462.9 Found: 461.2 (M−1).

EXAMPLE 2-52

N-{3-Chloro-4-[4-hydroxy-3-(1-phenyl-(1S)ethylcarbamoyl)-phenoxy]-5-methyl-phenyl}-oxamic acid ethyl ester, MS Calc.: 497.0 Found: 495.3 (M−1).

EXAMPLE 2-53

N-{3-Chloro-4-[3-(ethyl-methyl-carbamoyl)-4-hydroxy-phenoxy]-5-methyl-phenyl}-oxamic acid ethyl ester, MS Calc.: 434.9 Found: 433.3 (M−1).

EXAMPLE 2-54

N-{3-Chloro-4-[4-hydroxy-3-(methyl-propyl-carbamoyl)-phenoxy]-5-methyl-phenyl}-oxamic acid ethyl ester, MS Calc.: 448.9 Found: 447.2 (M−1).

EXAMPLE 2-55

N-{3-Chloro-4-[3-(ethyl-isopropyl-carbamoyl)-4-hydroxy-phenoxy]-5-methyl-phenyl}-oxamic acid ethyl ester, MS Calc.: 462.2 Found: 461.2 (M−1).

EXAMPLE 2-56

N-{3-Chloro-4-[3-(cyclobutyl-methyl-carbamoyl)-4-hydroxy-phenoxy]-5-methyl-phenyl}-oxamic acid ethyl ester, MS Calc.: 460.9 Found: 459.3 (M−1).

EXAMPLE 2-57

N-{4-[3-(Azepane-1-carbonyl)-4-hydroxy-phenoxy]-3-chloro-5-methyl-phenyl}-oxamic acid, MS Calc.: 446.9 Found: 445.3 (M−1).

EXAMPLE 2-58

N-{3-Chloro-4-[3-(1-cyclohexyl-(1S)ethylcarbamoyl)-4-hydroxy-phenoxy]-5-methyl-phenyl}-oxamic acid, MS Calc.: 475.0 Found: 473.2 (M−1).

EXAMPLE 2-59

N-{3-Chloro-4-[3-(cyclobutyl-methyl-carbamoyl)-4-hydroxy-phenoxy]-5-methyl-phenyl}-oxamic acid, MS Calc.: 432.9 Found: 431.3 (M−1).

EXAMPLE 2-60

N-{4-[3-(Bicyclo[2.2.1]hept-2-ylcarbamoyl)-4-hydroxy-phenoxy]-3,5-dichloro-phenyl}-oxamic acid ethyl ester, MS Calc.: 507.4 Found: 505.0 (M−1).

EXAMPLE 2-61

N-{4-[3-(Bicyclo[2.2.1]hept-2-ylcarbamoyl)-4-hydroxy-phenoxy]-3,5-dichloro-phenyl}-oxamic acid ethyl ester, MS Calc.: 507.4 Found: 505.1 (M−1).

EXAMPLE 2-62

N-(3,5-Dichloro-4-{4-hydroxy-3-[(thiophen-2-ylmethyl)-carbamoyl]-phenoxy}-phenyl)-oxamic acid ethyl ester, MS Calc.: 509.4 Found: 507.1 (M−1).

EXAMPLE 2-63

N-{3,5-Dichloro-4-[3-(2-chloro-benzylcarbamoyl)-4-hydroxy-phenoxy]-phenyl}-oxamic acid ethyl ester, MS Calc.: 537.8 Found: 535.0 (M−1).

EXAMPLE 2-64

N-{3,5-Dichloro-4-[4-hydroxy-3-(3-methyl-3-phenyl-piperidine-1-carbonyl)-phenoxy]-phenyl}-oxamic acid ethyl ester, MS Calc.: 571.5 Found: 569.2 (M−1).

EXAMPLE 2-65

N-{3,5-Dichloro-4-[3-(3,4-dihydro-1H-isoquinoline-2-carbonyl)-4-hydroxy-phenoxy]-phenyl}-oxamic acid ethyl ester, MS Calc.: 529.4 Found: 527.2 (M−1).

EXAMPLE 2-66

N-{3,5-Dichloro-4-[4-hydroxy-3-(indan-1-ylcarbamoyl)-phenoxy]-phenyl}-oxamic acid ethyl ester, MS Calc.: 529.4 Found: 527.2 (M−1).

EXAMPLE 2-67

N-(4-{3-[(Benzo[1,3]dioxol-5-ylmethyl)-carbamoyl]-4-hydroxy-phenoxy}-3,5-dichloro-phenyl)-oxamic acid ethyl ester, MS Calc.: 547.4 Found: 545.2 (M−1).

EXAMPLE 2-68

N-{4-[3-(Azepane-1-carbonyl)-4-hydroxy-phenoxy]-3,5-dichloro-phenyl}-oxamic acid ethyl ester, MS Calc.: 495.4 Found: 493.3 (M−1).

EXAMPLE 2-69

N-{3,5-Dichloro-4-[4-hydroxy-3-(4-methyl-piperidine-1-carbonyl)-phenoxy]-phenyl}-oxamic acid ethyl ester, MS Calc.: 495.4 Found: 493.2 (M−1).

EXAMPLE 2-70

N-{3,5-Dichloro-4-[3-(4-fluoro-phenylcarbamoyl)-4-hydroxy-phenoxy]-phenyl}-oxamic acid ethyl ester, MS Calc.: 507.3 Found: 505.1 (M−1).

EXAMPLE 2-71

N-{3,5-Dichloro-4-[3-(cyclohexylmethyl-carbamoyl)-4-hydroxy-phenoxy]-phenyl}-oxamic acid ethyl ester, MS Calc.: 509.4 Found: 507.2 (M−1).

EXAMPLE 2-72

N-{3,5-Dichloro-4-[3-(1-cyclohexyl-(1R)ethylcarbamoyl)-4-hydroxy-phenoxy]-phenyl}-oxamic acid ethyl ester, MS Calc.: 523.4 Found: 521.2 (M−1).

EXAMPLE 2-73

N-(3,5-Dichloro-4-[3-(1-cyclohexyl-(1S)ethylcarbamoyl)-4-hydroxy-phenoxy]-phenyl}-oxamic acid ethyl ester, MS Calc.: 523.4 Found: 521.2 (M−1).

EXAMPLE 2-74

N-{3,5-Dichloro-4-[4-hydroxy-3-(piperidine-1-carbonyl)-phenoxy]-phenyl}-oxamic acid ethyl ester, MS Calc.: 481.3 Found: 481.2 (M−1).

EXAMPLE 2-75

N-{3,5-Dichloro-4-[4-hydroxy-3-(3-methyl-piperidine-1-carbonyl)-phenoxy]-phenyl}-oxamic acid ethyl ester, MS Calc.: 495.3 Found: 493.1 (M−1).

EXAMPLE 2-76

N-{4-[3-(Biphenyl-3-ylcarbamoyl)-4-hydroxy-phenoxy]-3,5-dichloro-phenyl}-oxamic acid ethyl ester, MS Calc.: 565.4 Found: 563.2 (M−1).

EXAMPLE 2-77

N-[3,5-Dichloro-4-(3-cyclopropylcarbamoyl-4-hydroxy-phenoxy)-phenyl]-oxamic acid ethyl ester, MS Calc.: 453.3 Found: 453.2 (M−1).

EXAMPLE 2-78

N-{3,5-Dichloro-4-[3-(2,3-dichloro-benzylcarbamoyl)-4-hydroxy-phenoxy]-phenyl}-oxamic acid ethyl ester, MS Calc.: 572.2 Found: 571.0 (M−1).

EXAMPLE 2-79

N-[3,5-Dichloro-4-(3-cyclobutylcarbamoyl-4-hydroxy-phenoxy)-phenyl]-oxamic acid ethyl ester, MS Calc.: 467.3 Found: 465.2 (M−1).

EXAMPLE 2-80

N-[3,5-Dichloro-4-(3-cyclopentylcarbamoyl-4-hydroxy-phenoxy)-phenyl]-oxamic acid ethyl ester, MS Calc.: 481.3 Found: 479.2 (M−1).

EXAMPLE 2-81

N-(3,5-Dichloro-4-{4-hydroxy-3-[(naphthalen-1-ylmethyl)-carbamoyl]-phenoxy}-phenyl)-oxamic acid ethyl ester, MS Calc.: 533.4 Found: 551.1 (M−1).

EXAMPLE 2-82

N-{3,5-Dichloro-4-[3-(4-fluoro-benzylcarbamoyl)-4-hydroxy-phenoxy]-phenyl}-oxamic acid ethyl ester, MS Calc.: 521.3 Found: 519.2 (M−1).

EXAMPLE 2-83

N-{4-[3-(Azocane-1-carbonyl)-4-hydroxy-phenoxy]-3,5-dichloro-phenyl}-oxamic acid ethyl ester, MS Calc.: 509.4 Found: 507.2 (M−1).

EXAMPLE 2-84

N-{3,5-Dichloro-4-[4-hydroxy-3-(1,2,3,4-tetrahydro-naphthalen-1-ylcarbamoyl)-phenoxy]-phenyl}-oxamic acid ethyl ester, MS Calc.: 543.4 Found: 541.2 (M−1).

EXAMPLE 2-85

N-{3,5-Dichloro-4-[4-hydroxy-3-(1-isopropyl-2-methyl-propylcarbamoyl)-phenoxy]-phenyl}-oxamic acid ethyl ester, MS Calc.: 511.4 Found: 509.2 (M−1).

EXAMPLE 2-86

N-{3,5-Dichloro-4-[4-hydroxy-3-(6-methoxy-3,4-dihydro-2H-quinoline-1-carbonyl)-phenoxy]-phenyl}-oxamic acid ethyl ester, MS Calc.: 559.4 Found: 556.4 (M−1).

EXAMPLE 2-87

N-{3,5-Dichloro-4-[4-hydroxy-3-(6-methyl-3,4-dihydro-2H-quinoline-1-carbonyl)-phenoxy]-phenyl}-oxamic acid ethyl ester, MS Calc.: 543.4 Found: 541.1 (M−1).

EXAMPLE 2-88

N-{3,5-Dichloro-4-[4-hydroxy-3-(4-isopropyl-benzylcarbamoyl)-phenoxy]-phenyl}-oxamic acid ethyl ester, MS Calc.: 545.4 Found: 545.0 (M−1).

EXAMPLE 2-89

N-{3,5-Dichloro-4-[3-(4-chloro-benzylcarbamoyl)-4-hydroxy-phenoxy]-phenyl}-oxamic acid ethyl ester, MS Calc.: 537.8 Found: 535.0 (M−1).

EXAMPLE 2-90

N-{3,5-Dichloro-4-[4-hydroxy-3-((1R)indan-1-ylcarbamoyl)-phenoxy]-phenyl)-oxamic acid ethyl ester, MS Calc.: 529.4 Found: 527.1 (M−1).

EXAMPLE 2-91

N-{3,5-Dichloro-4-[4-hydroxy-3-((1S)indan-1-ylcarbamoyl)-phenoxy]-phenyl}-oxamic acid ethyl ester, MS Calc.: 529.4 Found: 527.1 (M−1).

EXAMPLE 2-92

N-{3,5-Dichloro-4-[4-hydroxy-3-(1-phenyl-(1R)ethylcarbamoyl)-phenoxy]-phenyl}-oxamic acid ethyl ester, MS Calc.: 517.4 Found: 514.8 (M−1).

EXAMPLE 2-93

N-{3,5-Dichloro-4-[4-hydroxy-3-(1-naphthalen-1-yl-(1S)ethylcarbamoyl)-phenoxy]-phenyl}-oxamic acid ethyl ester, MS Calc.: 567.4 Found: 564.8 (M−1).

EXAMPLE 2-94

N-{3,5-Dichloro-4-[3-(3,4-difluoro-benzylcarbamoyl)-4-hydroxy-phenoxy]-phenyl}-oxamic acid ethyl ester, MS Calc.: 539.3 Found: 536.7 (M−1).

EXAMPLE 2-95

N-{3,5-Dichloro-4-[3-(3-chloro-4-fluoro-benzylcarbamoyl)-4-hydroxy-phenoxy]-phenyl}-oxamic acid ethyl ester, MS Calc.: 555.8 Found: 555.1 (M−1).

EXAMPLE 2-96

N-{3,5-Dichloro-4-[3-(2-chloro-4-fluoro-benzylcarbamoyl)-4-hydroxy-phenoxy]-phenyl}-oxamic acid ethyl ester, MS Calc.: 555.8 Found: 553.0 (M−1).

EXAMPLE 2-97

N-{3,5-Dichloro-4-[4-hydroxy-3-(1-naphthalen-2-yl-(1R)ethylcarbamoyl)-phenoxy]-phenyl}-oxamic acid ethyl ester, MS Calc.: 567.4 Found: 565.1 (M−1).

EXAMPLE 2-98

N-{3,5-Dichloro-4-[3-(2,4-dichloro-benzylcarbamoyl)-4-hydroxy-phenoxy]-phenyl}-oxamic acid ethyl ester, MS Calc.: 572.2 Found: 572.9 (M+1).

EXAMPLE 2-99

N-{3,5-Dichloro-4-[3-(3,4-dichloro-benzylcarbamoyl)-4-hydroxy-phenoxy]-phenyl}-oxamic acid ethyl ester, MS Calc.: 572.2 Found: 571.1 (M−1).

EXAMPLE 2-100

N-3,5-Dichloro-4-[3-(4-chloro-3-trifluoromethyl-benzylcarbamoyl)-4-hydroxy-phenoxy]-phenyl}-oxamic acid ethyl ester, MS Calc.: 605.8 Found: 606.9 (M+1).

EXAMPLE 2-101

N-{3,5-Dichloro-4-[3-(4-chloro-2-fluoro-benzylcarbamoyl)-4-hydroxy-phenoxy]-phenyl}-oxamic acid ethyl ester, MS Calc.: 555.8 Found: 553.1 (M−1).

EXAMPLE 2-102

N-{4-[3-(4-tert-Butyl-benzylcarbamoyl)-4-hydroxy-phenoxy]-3,5-dichloro-phenyl}-oxamic acid ethyl ester, MS Calc.: 559.5 Found: 557.2 (M−1).

EXAMPLE 2-103

N-[3,5-Dichloro-4-(3-cyclohexylcarbamoyl-4-hydroxy-phenoxy)-phenyl]-oxamic acid ethyl ester, MS Calc.: 495.4 Found: 493.2 (M−1).

EXAMPLE 2-104

N-[3,5-Dichloro-4-(4-hydroxy-3-isopropylcarbamoyl-phenoxy)-phenyl]-oxamic acid ethyl ester, MS Calc.: 455.3 Found: 453.1 (M−1).

EXAMPLE 2-105

N-{3,5-Dichloro-4-[4-hydroxy-3-(isopropyl-methyl-carbamoyl)-phenoxy]-phenyl}-oxamic acid ethyl ester, MS Calc.: 469.3 Found: 467.2 (M−1).

EXAMPLE 2-106

N-{3,5-Dichloro-4-[3-(cyclopropylmethyl-carbamoyl)-4-hydroxy-phenoxy]-phenyl}-oxamic acid ethyl ester, MS Calc.: 467.3 Found: 465.2 (M−1).

EXAMPLE 2-107

N-{3,5-Dichloro-4-[3-(4-fluoro-benzylcarbamoyl)-4-hydroxy-phenoxy]-phenyl}-oxamic acid, MS Calc.: 493.3 Found: 491.1 (M−1).

EXAMPLE 2-108

N-[3,5-Dichloro-4-(3-dimethylcarbamoyl-4-hydroxy-phenoxy)-phenyl]-oxamic acid, MS Calc.: 413.2 Found: 413.2 (M−1).

EXAMPLE 2-109

N-{3,5-Dichloro-4-[4-hydroxy-3-(1-isopropyl-2-methyl-propylamino-carbonyl)-phenoxy]-phenyl}-oxamic acid, MS Calc.: 483.4 Found: 481.2 (M−1).

EXAMPLE 3

N{3,5-Dichloro-4-[4-hydroxy-3-(indan-1-ylaminomethyl)-phenoxy]-phenyl}-oxamic Acid Ethyl Ester

Step A

To a solution of 2', 6'-dichloro-4-methoxy-4'-nitrodiphenyl ether (10 g, 31.8 mmol) in chloroform (200 mL) at 0° C. was added dropwise borontribromide (1N in $CH_2Cl_2$, 63.7 mL, 63.7 mmol). After stirring at RT for 3 h, the reaction was quenched with $H_2O$ (200 mL). The mixture was stirred at RT for 1 h, and the phases were separated. The aqueous phase was extracted with chloroform (2×150 mL). The combined organic phases were washed with $H_2O$ (1×200 mL), saturated aqueous $NaHCO_3$ (1×200 mL), brine (1×200 mL), dried over $Na_2SO_4$, filtered and concentrated to afford a brown solid. The crude product was used in the next step without further purification. NMR (400 MHz, $CD_3OD$) d 8.28 (s, 2H), 6.67–6.70 (m, 2H), 6.61–6.64 (m, 2H). MS Calc.: 299.0, Found: 298.2 (M−1).

Step B

To a solution of 2', 6'-dichloro-4-hydroxy-4'-nitrodiphenyl ether (9.5 g, 32 mmol) in a mixture of EtOAC (50 mL) and MeOH (150 mL) was added 0.48 g of 10% Pd/C. The mixture was hydrogenated under 40 psi of pressure at RT for 5 h. The solution was filtered through Celite® and concentrated to give a brown solid. NMR (400 MHz, CD$_3$OD) d 6.71 (s, 2H), 6.66–6.68 (m, 2H), 6.59–6.61 (m, 2H). MS Calc.: 269.0, Found: 268.2 (M−1).

Step C

A mixture of 2', 6'-dichloro-4-hydroxy-4'-aminodiphenyl ether (8.6 g, 31.8 mmol) and diethyl oxalate (69.8 g, 47.8 mmol) was stirred at 140° C. for 2 h to give a brown solution. The excess diethyl oxalate was removed under reduced pressure and the resulting oily brown solid was triturated with a mixture of CH$_2$Cl$_2$/hexane (1/19, 200 mL) for 1 h. The solid was collected by filtration, washed with CH$_2$Cl$_2$/hexane and dried under vacuum to give a tan solid. The product was used in the next step without further purification. NMR (400 MHz, CDCl$_3$) d 7.68 (s, 2H), 6.59–6.61 (m, 2H), 6.53–6.55 (m, 2H), 4.25–4.30 (q, 2H), 1.27–1.31 (t, 3H). MS Calc.: 369.0, Found: 367.5 (M−1).

Step D

A mixture of N-[3,5-dichloro-4-(4-hydroxy-phenoxy)-phenyl]-oxamic acid ethyl ester (500 mg, 1.35 mmol), TFA (5.0 mL) and hexamethylenetetramine (284 mg, 2.03 mmol) was stirred at 75° C. for 1 h to give a red-brown solution. The solution was cooled to RT. TFA was removed under reduced pressure and 20 mL of H$_2$O was added to the remaining brown oil. After stirring for 20 min at RT, the mixture was extracted with EtOAc (2×20 mL). The aqueous phase was basified with saturated aqueous NaHCO$_3$ and extracted with an additional EtOAc (2×20 mL). The combined EtOAc extracts were washed with saturated aqueous NaHCO$_3$ (2×30 mL), H$_2$O (50 mL), 1 N HCl (2×50 mL), brine (50 mL), dried over Na$_2$SO$_4$, filtered and concentrated to give a brown solid. The crude product was purified by flash column chromatography to afford a white solid. NMR (400 MHz, CDCl$_3$) d 10.72 (s, 1H), 9.77 (s, 1H), 8.90 (s, 1H), 7.71 (s, 2H), 7.14–7.17 (dd, 1H), 6.96–6.98 (d, 1H), 6.89–6.90 (d, 1H), 4.42–4.47 (q, 2H), 1.23–1.27 (t, 3H). MS Calc.: 397.0, Found: 395.7 (M−1).

Step E

To a mixture of N-[3,5-dichloro-4-(3-formyl-4-hydroxy-phenoxy)-phenyl]-oxamic acid ethyl ester (30 mg, 0.08 mmol) and aminoindan (10 mg, 0.08 mmol) in dichloroethane (1.0 mL) was added sodium triacetoxyborohydride (22.4 mg, 0.11 mmol) and acetic acid (4.5 mg, 0.08 mmol) in single portions. After stirring at RT for 3 h, the solution became clear and yellow. The solution was quenched with saturated aqueous NaHCO$_3$ (5 mL) and extracted with Et$_2$O (3×10 mL). The combined extracts were dried over Na$_2$SO$_4$, filtered and concentrated to give the crude product as a yellow glass. The crude product was purified by preparative TLC (5% Et$_2$O in CH$_2$Cl$_2$) to afford the title compound as an off-white solid. NMR (400 MHz, CDCl$_3$) d 8.94 (s, 1H), 7.74 (s, 2H), 7.36–7.37 (d, 1H), 7.19–7.25 (m, 4H), 6.75–6.77 (d, 1H), 6.61–6.64 (dd, 1H), 6.54–6.55 (d, 1H), 4.40–4.46 (q, 2H), 4.30–4.33 (t, 1H), 4.05–4.08 (d, 1H), 3.95–3.98 (d, 1H), 2.98–3.06 (m, 1H), 2.81–2.88 (m, 1H), 2.42–2.51 (m, 1H), 1.88–1.96 (m, 1H), 1.41–1.45 (t, 3H). MS Calc.: 514.20, Found: 513.1 (M−1).

Using the appropriate starting materials, EXAMPLES 3-1 to 3-54 were prepared in an analogous manner to that described in EXAMPLE 3.

EXAMPLE 3-1

N-{4-[3-(2,3-Dihydro-indol-1-ylmethyl)-4-hydroxy-phenoxy]-3,5-dimethyl-phenyl}-oxamic acid ethyl ester, MS Calc.: 460.5 Found: 459.3 (M−1).

EXAMPLE 3-2

N-{4-[3-(3,3-Dimethyl-piperidin-1-ylmethyl)-4-hydroxy-phenoxy]-3,5-dimethyl-phenyl}-oxamic acid ethyl ester, MS Calc.: 454.6 Found: 453.3 (M−1).

EXAMPLE 3-3

N-{4-[4-Hydroxy-3-(3-methyl-3-phenyl-piperidin-1-ylmethyl)-phenoxy]-3,5-dimethyl-phenyl}-oxamic acid ethyl ester, MS Calc.: 516.6 Found: 515.3 (M−1).

EXAMPLE 3-4

N-{4-[3-(3,4-Dihydro-1H-isoquinolin-2-ylmethyl)-4-hydroxy-phenoxy]-3,5-dimethyl-phenyl}-oxamic acid ethyl ester, MS Calc.: 474.6 Found: 473.3 (M−1).

EXAMPLE 3-5

N-(4-{3-[(4-Fluoro-benzylamino)-methyl]-4-hydroxy-phenoxy}-3,5-dimethyl-phenyl)-oxamic acid ethyl ester, MS Calc.: 466.5 Found: 465.2 (M−1).

EXAMPLE 3-6

N-(4-{3-[(4-Chloro-benzylamino)-methyl]-4-hydroxy-phenoxy}-3,5-dimethyl-phenyl)-oxamic acid ethyl ester, MS Calc.: 483.0 Found: 481.3 (M−1).

EXAMPLE 3-7

N-(4-{4-Hydroxy-3-[(4-isopropyl-benzylamino)-methyl]-phenoxy}-3,5-dimethyl-phenyl)-oxamic acid ethyl ester, MS Calc.: 490.6 Found: 489.2 (M−1).

EXAMPLE 3-8

N-[4-(3-Azepan-1-ylmethyl-4-hydroxy-phenoxy)-3,5-dimethyl-phenyl]-oxamic acid ethyl ester, MS Calc.: 440.5 Found: 439.3 (M−1).

EXAMPLE 3-9

N-[4-(3-{[(Benzo[1,3]dioxol-5-ylmethyl)-amino]-methyl}-4-hydroxy-phenoxy)-3,5-dimethyl-phenyl]-oxamic acid ethyl ester, MS Calc.: 492.5 Found: 491.3 (M−1).

EXAMPLE 3-10

N-(4-{4-Hydroxy-3-[(1,2,3,4-tetrahydro-naphthalen-1-ylamino)-methyl]-phenoxy}-3,5-dimethyl-phenyl)-oxamic acid ethyl ester, MS Calc.: 488.6 Found: 487.4 (M−1).

EXAMPLE 3-11

N-[4-(3-Dimethylaminomethyl-4-hydroxy-phenoxy)-3,5-dimethyl-phenyl]-oxamic acid ethyl ester, MS Calc.: 386.5 Found: 385.3 (M−1).

EXAMPLE 3-12

N-(4-{4-Hydroxy-3-[(methyl-propyl-amino)-methyl]-phenoxy}-3,5-dimethyl-phenyl)-oxamic acid ethyl ester, MS Calc.: 414.9 Found: 413.4 (M−1).

EXAMPLE 3-13

N-[4-(3-Cyclopropylaminomethyl-4-hydroxy-phenoxy)-3,5-dimethyl-phenyl]-oxamic acid ethyl ester, MS Calc.: 398.5 Found: 397.4 (M−1).

EXAMPLE 3-14

N-[4-(4-Hydroxy-3-morpholin-4-ylmethyl-phenoxy)-3,5-dimethyl-phenyl]-oxamic acid ethyl ester, MS Calc.: 428.5 Found: 427.3 (M−1).

EXAMPLE 3-15

N-(4-{4-Hydroxy-3-[(isopropyl-methyl-amino)-methyl]-phenoxy}-3,5-dimethyl-phenyl)-oxamic acid ethyl ester, MS Calc.: 414.5 Found: 413.5 (M−1).

EXAMPLE 3-16

N-{4-[4-Hydroxy-3-(isopropylamino-methyl)-phenoxy]-3,5-dimethyl-phenyl}-oxamic acid ethyl ester, MS Calc.: 400.5 Found: 399.4 (M−1).

EXAMPLE 3-17

N-[4-(3-Cyclobutylaminomethyl-4-hydroxy-phenoxy)-3,5-dimethyl-phenyl]-oxamic acid ethyl ester, MS Calc.: 412.5 Found: 411.4 (M−1).

EXAMPLE 3-18

N-[4-(3-Cyclopentylaminomethyl-4-hydroxy-phenoxy)-3,5-dimethyl-phenyl]-oxamic acid ethyl ester, MS Calc.: 426.5 Found: 425.4 (M−1).

EXAMPLE 3-19

N-{3-Chloro-4-[3-(3,3-dimethyl-piperidin-1-ylmethyl)-4-hydroxy-phenoxy]-5-methyl-phenyl}-oxamic acid methyl ester, MS Calc.: 461.0 Found: 461.1 (M+1).

EXAMPLE 3-20

N-{3-Chloro-4-[3-(2,3-dihydro-indol-1-ylmethyl)-4-hydroxy-phenoxy]-5-methyl-phenyl}-oxamic acid methyl ester, MS Calc.: 467.0 Found: 467.2 (M+1).

EXAMPLE 3-21

N-(3-Chloro-4-{3-[(4-fluoro-benzylamino)-methyl]-4-hydroxy-phenoxy}-5-methyl-phenyl)-oxamic acid ethyl ester, MS Calc.: 486.9 Found: 485.2 (M−1).

EXAMPLE 3-22

N-{3-Chloro-4-[4-hydroxy-3-(3-methyl-3-phenyl-piperidin-1-ylmethyl)-phenoxy]-5-methyl-phenyl}-oxamic acid ethyl ester, MS Calc.: 537.1 Found: 535.2 (M−1).

EXAMPLE 3-23

N-(3-Chloro-4-{3-[(4-chloro-benzylamino)-methyl]-4-hydroxy-phenoxy}-5-methyl-phenyl)-oxamic acid ethyl ester, MS Calc.: 503.4 Found: 501.1 (M−1).

EXAMPLE 3-24

N-(3-Chloro-4-{4-hydroxy-3-[(4-isopropyl-benzyl-amino)-methyl]-phenoxy}-5-methyl-phenyl)-oxamic acid ethyl ester, MS Calc.: 511.2 Found: 509.2 (M−1).

EXAMPLE 3-25

N-{3-Chloro-4-[3-(3,4-dihydro-1H-isoquinolin-2-ylmethyl)-4-hydroxy-phenoxy]-5-methyl-phenyl}-oxamic acid ethyl ester, MS Calc.: 495.0 Found: 493.2 (M−1).

EXAMPLE 3-26

N-[4-(3-Azepan-1-ylmethyl-4-hydroxy-phenoxy)-3-chloro-5-methyl-phenyl]-oxamic acid ethyl ester, MS Calc.: 461.0 Found: 459.2 (M−1).

EXAMPLE 3-27

N-[4-(3-{[(Benzo[1,3]dioxol-5-ylmethyl)-amino]-methyl}-4-hydroxy-phenoxy)-3-chloro-5-methyl-phenyl]-oxamic acid ethyl ester, MS Calc.: 513.0 Found: 511.2 (M−1).

EXAMPLE 3-28

N-(3-Chloro-4-{4-hydroxy-3-[(1,2,3,4-tetrahydro-naphthalen-1-ylamino)-methyl]-phenoxy}-5-methyl-phenyl)-oxamic acid ethyl ester, MS Calc.: 509.0 Found: 507.3 (M−1).

EXAMPLE 3-29

N-[3-Chloro-4-(3-dimethylaminomethyl-4-hydroxy-phenoxy)-5-methyl-phenyl]-oxamic acid ethyl ester, MS Calc.: 406.9 Found: 405.3 (M−1).

EXAMPLE 3-30

N-(3-Chloro-4-{4-hydroxy-3-[(methyl-propyl-amino)-methyl]-phenoxy}-5-methyl-phenyl)-oxamic acid ethyl ester, MS Calc.: 434.9 Found: 433.3 (M−1).

EXAMPLE 3-31

N-[3-Chloro-4-(3-cyclopropylaminomethyl-4-hydroxy-phenoxy)-5-methyl-phenyl]-oxamic acid ethyl ester, MS Calc.: 418.9 Found: 417.3 (M−1).

EXAMPLE 3-32

N-{3,5-Dichloro-4-[3-(2,3-dihydro-indol-1-ylmethyl)-4-hydroxy-phenoxy]-phenyl}-oxamic acid methyl ester, MS Calc.: 487.3 Found: 487.2 (M+1).

EXAMPLE 3-33

N-{3,5-Dichloro-4-[3-(3,3-dimethyl-piperidin-1-ylmethyl)-4-hydroxy-phenoxy]-phenyl}-oxamic acid methyl ester, MS Calc.: 481.4 Found: 481.2 (M+1).

EXAMPLE 3-34

N-{3,5-Dichloro-4-[4-hydroxy-3-(indan-1-ylamino-methyl)-phenoxy]-phenyl}-oxamic acid methyl ester, MS Calc.: 501.4 Found: 499.1 (M−1).

EXAMPLE 3-35

N-{3,5-Dichloro-4-[3-(3,4-dihydro-1H-isoquinolin-2-ylmethyl)-4-hydroxy-phenoxyl]-phenyl}-oxamic acid methyl ester, MS Calc.: 501.4 Found: 501.1 (M+1).

EXAMPLE 3-36

N-[4-(3-Azepan-1-ylmethyl-4-hydroxy-phenoxy)-3,5-dichloro-phenyl]-oxamic acid methyl ester, MS Calc.: 467.4 Found: 465.1 (M−1).

EXAMPLE 3-37

N-(3,5-Dichloro-4-{3-[(1-cyclohexyl-(1R)ethylamino)-methyl]-4-hydroxy-phenoxy}-phenyl)-oxamic acid ethyl ester, MS Calc.: 509.4 Found: 507.2 (M−1).

EXAMPLE 3-38

N-{4-[3-(Bicyclo[2.2.1]hept-2-ylaminomethyl)-4-hydroxy-phenoxy]-3,5-dichloro-phenyl}-oxamic acid ethyl ester, MS Calc.: 493.4 Found: 491.2 (M−1).

EXAMPLE 3-39

N-{3,5-Dichloro-4-[4-hydroxy-3-(3-methyl-3-phenyl-piperidin-1-ylmethyl)-phenoxy]-phenyl}-oxamic acid ethyl ester, MS Calc.: 557.5 Found: 555.1 (M−1).

EXAMPLE 3-40

N-(3,5-Dichloro-4-{3-[(4-fluoro-benzylamino)-methyl]-4-hydroxy-phenoxy}-phenyl)-oxamic acid ethyl ester, MS Calc.: 507.35 Found: 505.0 (M−1).

EXAMPLE 3-41

N-(3,5-Dichloro-4-{4-hydroxy-3-[(1-phenyl-(1R)ethylamino)-methyl]-phenoxy}-phenyl)-oxamic acid ethyl ester, MS Calc.: 503.4 Found: 501.0 (M−1).

EXAMPLE 3-42

N-(3,5-Dichloro-4-{4-hydroxy-3-[(1-phenyl-(1S)ethylamino)-methyl]-phenoxy}-phenyl)-oxamic acid ethyl ester, MS Calc.: 503.4 Found: 501.0 (M−1).

EXAMPLE 3-43

N-[3,5-Dichloro-4-(4-hydroxy-3-{[(naphthalen-1-ylmethyl)-amino]-methyl}-phenoxy)-phenyl]-oxamic acid ethyl ester, MS Calc.: 539.4 Found: 536.7 (M−1).

EXAMPLE 3-44

N-(3,5-Dichloro-4-{4-hydroxy-3-[(1-naphthalen-1-yl-(1R)ethylamino)-methyl]-phenoxy}-phenyl)-oxamic acid ethyl ester, MS Calc.: 553.5 Found: 550.8 (M−1).

EXAMPLE 3-45

N-(3,5-Dichloro-4-{4-hydroxy-3-[(1,2,3,4-tetrahydro-naphthalen-1-ylamino)-methyl]-phenoxy}-phenyl)-oxamic acid ethyl ester, MS Calc.: 529.4 Found: 526.8 M−1).

EXAMPLE 3-46

N-[3,5-Dichloro-4-(3-cyclohexylaminomethyl-4-hydroxy-phenoxy)-phenyl]-oxamic acid ethyl ester, MS Calc.: 481.4 Found: 478.8 (M−1).

EXAMPLE 3-47

N-[3,5-Dichloro-4-(3-cyclopentylaminomethyl-4-hydroxy-phenoxy)-phenyl]-oxamic acid ethyl ester, MS Calc.: 467.4 Found: 465.1 (M−1).

EXAMPLE 3-48

N-[4-(3-{[(Benzo[1,3]dioxol-5-ylmethyl)-amino]-methyl}-4-hydroxy-phenoxy)-3,5-dichloro-phenyl]-oxamic acid ethyl ester, MS Calc.: 533.4 Found: 531.0 (M−1).

EXAMPLE 3-49

N-(3,5-Dichloro-4-{3-[(4-chloro-benzylamino)-methyl]-4-hydroxy-phenoxy}-phenyl)-oxamic acid ethyl ester, MS Calc.: 523.8 Found: 521.1 (M−1).

EXAMPLE 3-50

N-(3,5-Dichloro-4-{4-hydroxy-3-[(4-isopropyl-benzylamino)-methyl]-phenoxy}-phenyl)-oxamic acid ethyl ester, MS Calc.: 531.4 Found: 529.2 (M−1).

EXAMPLE 3-51

N-[3,5-Dichloro-4-(4-hydroxy-3-methylaminomethyl-phenoxy)-phenyl]-oxamic acid ethyl ester, MS Calc.: 413.3 Found: 411.2 (M−1).

EXAMPLE 3-52

N-[3,5-Dichloro-4-(3-cyclopropylaminomethyl-4-hydroxy-phenoxy)-phenyl]-oxamic acid ethyl ester, MS Calc.: 439.3 Found: 437.3 (M−1).

EXAMPLE 3-53

N-[3,5-Dichloro-4-(4-hydroxy-3-morpholin-4-ylmethyl-phenoxy)-phenyl]-oxamic acid ethyl ester, MS Calc.: 469.3 Found: 467.3 (M−1).

EXAMPLE 3-54

N-[3,5-Dichloro-4-(3-cyclobutylaminomethyl-4-hydroxy-phenoxy)-phenyl]-oxamic acid ethyl ester, MS Calc.: 453.3 Found: 451.3 (M−1).

EXAMPLE 4

N-{4-[4-Hydroxy-3-(isopropylmethylcarbamoyl)-phenoxy]-3,5-dimethyl-phenyl}-oxamide A solution of N-{4-[4-hydroxy-3-(isopropylmethylcarbamoyl)-phenoxy]-3,5-dimethyl-phenyl}-oxamic acid ethyl ester (7.1 mg, 0.017 mmol) in 1 mL of EtOH in the presence of magnesium sulfate (10 mg) at 0° C. was bubbled in $NH_3$ gas for 10 min. The solution was allowed to warm to RT. After stirring at RT for 0.5 h, the solution was diluted with 2 mL of $CH_2Cl_2$ and filtered. The filtrate was concentrated to give the title compound as a white solid. MS Calc.: 399.5 Found: 398.4 (M−1).

Using the appropriate starting materials, EXAMPLES 4-1 to 4-10 were prepared in an analogous manner to that described in EXAMPLE 4.

EXAMPLE 4-1

N-{4-[4-Hydroxy-3-(1-isopropyl-2-methyl-propylcarbamoyl)-phenoxy]-3,5-dimethyl-phenyl}-oxamide, MS Calc.: 441.5 Found: 440.5 (M−1).

EXAMPLE 4-2

N-[3,5-Dichloro-4-(3-cyclohexylcarbamoyl-4-hydroxy-phenoxy)-phenyl]-oxamide, MS Calc.: 465.1 Found: 464.2 (M−1).

EXAMPLE 4-3

N-{3-Chloro-4-[4-hydroxy-3-(morpholine-4-sulfonyl)-phenoxy]-5-methyl-phenyl}-oxamide, MS Calc.: 469.1 Found: 468.2 (M−1).

EXAMPLE 4-4

N-[4-(3-Benzenesulfonyl-4-hydroxy-phenoxy)-3,5-dichloro-phenyl]-oxamide, MS Calc.: 480.0 Found: 479.2 (M−1).

EXAMPLE 4-5

N-{3-Chloro-4-[3-(cyclobutylmethylcarbamoyl)-4-hydroxy-phenoxy]-5-methyl-phenyl}-oxamide, MS Calc.: 431.1 Found: 430.3 (M−1).

EXAMPLE 4-6

N-{3-Chloro-4-[3-(cyclopropylmethyl-amino-sulfonyl)-4-hydroxy-phenoxy]-5-methyl-phenyl}-oxamide, MS Calc.: 453.1 Found: 452.3 (M−1).

EXAMPLE 4-7

N-{3-Chloro-4-[4-hydroxy-3-(methylpropylsulfamoyl)-phenoxy]-5-methyl-phenyl}-oxamide, MS Calc.: 455.1 Found: 454.2 (M−1).

EXAMPLE 4-8

N-{4-[4-Hydroxy-3-(pyrrolidine-1-carbonyl)-phenoxy]-3,5-dimethyl-phenyl}-oxamide, MS Calc.: 397.4 Found: 396.3 (M−1).

EXAMPLE 4-9

N-[3-Chloro-4-(3-cyclopropylsulfamoyl-4-hydroxy-phenoxy)-5-methyl-phenyl]-oxamide, MS Calc.: 439.1 Found: 438.2 (M−1).

EXAMPLE 4-10

N-{4-[3-(Cyclobutyl-methyl-carbamoyl)-4-hydroxy-phenoxy]-3,5-dimethyl-phenyl}-oxamide, MS Calc.: 411.5 Found: 410.3 (M−1).

EXAMPLE 5

N-{3,5-Dichloro-4-[3-(4-chloro-benzenesulfonyl)-4-hydroxy-phenoxy]-phenyl}-oxamic acid ethyl ester

Step A

A mixture of 2',6'-dichloro-4-methoxy-4'-nitrodiphenyl ether (250 mg, 0.80 mmol), p-chlorobenzene sulfonic acid (90%, 290 mg, 1.4 mmol) and Eaton's reagent was stirred at 80° C. for 5 h and cooled to RT. The reaction mixture was quenched by adding dropwise into 30 mL of ice water. A white precipitate formed. The precipitate was collected by filtration and taken up in $CH_2Cl_2$, dried and concentrated. The product was purified by preparative TLC (25% EtOAc in Hex). NMR (400 MHz, $CDCl_3$) d 8.29–8.30 (s, 2H), 7.83–7.86 (d, 2H), 7.53–754 (d, 1H), 7.42–7.46 (d, 2H), 7.04–7.07 (dd, 1H), 6.82–6.87 (d, 1H), 3.73 (s, 3H). MS Calc.: 486.9, Found: 486.0 (M−1).

Step B

The title compound of this EXAMPLE 5 can be prepared from the product of Step A via demethylation, hydrogenation, and oxamate formation according to the methods analogous to those described in the present disclosure and known procedures. NMR (400 MHz, $CDCl_3$) d 8.95 (s, 1H), 8.68 (broad s, 1H), 7.80–7.82 (d, 2H), 7.76 (s, 2H), 7.49–7.51 (d, 2H), 7.06 (d, 1H), 7.00–7.02 (dd, 1H), 6.93–6.95 (d, 1H), 4.43 (q, 2H), 1.44 (t, 3H). MS Calc.: 543.0 Found: 542.1 (M−1).

Using the appropriate starting materials, EXAMPLES 5-1 to 5-12 were prepared in an analogous manner to that described in EXAMPLE 5.

EXAMPLE 5-1

N-{3,5-Dichloro-4-[3-(4-chloro-benzenesulfonyl)-4-hydroxy-phenoxy]-phenyl}-oxamic acid, MS Calc.: 514.9 Found: 513.0 (M−1).

EXAMPLE 5-2

N-{3-Chloro-4-[3-(4-chloro-benzenesulfonyl)-4-hydroxy-phenoxy]-5-methyl-phenyl}-oxamic acid, MS Calc.: 495.0 Found: 494.1 (M−1).

EXAMPLE 5-3

N-{3-Chloro-4-[3-(4-chloro-benzenesulfonyl)-4-hydroxy-phenoxy]-5-methyl-phenyl}-oxamide, MS Calc.: 494.0 Found: 493.2 (M−1).

EXAMPLE 5-4

N-[4-(3-Benzenesulfonyl-4-hydroxy-phenoxy)-3,5-dichloro-phenyl]-oxamic acid ethyl ester, MS Calc.: 509.0 Found: 508.2 (M−1).

EXAMPLE 5-5

N-[4-(3-Benzenesulfonyl-4-hydroxy-phenoxy)-3,5-dichloro-phenyl]-oxamic acid, MS Calc.: 481.0 Found: 480.2 (M−1).

EXAMPLE 5-6

N-[4-(3-Benzenesulfonyl-4-hydroxy-phenoxy)-3,5-dichloro-phenyl]-oxamide, MS Calc.: 480.0 Found: 479.2 (M−1).

EXAMPLE 5-7

N-{3,5-Dichloro-4-[4-hydroxy-3-(naphthalene-1-sulfonyl)-phenoxy]-phenyl}-oxamic acid ethyl ester, MS Calc.: 559.0 Found: 558.2 (M−1).

EXAMPLE 5-8

N-{3,5-Dichloro-4-[4-hydroxy-3-(naphthalene-1-sulfonyl)-phenoxy]-phenyl}-oxamic acid, MS Calc.: 531.0 Found: 530.1 (M−1).

EXAMPLE 5-9

N-{3,5-Dichloro-4-[4-hydroxy-3-(naphthalene-2-sulfonyl)-phenoxy]-phenyl}-oxamic acid ethyl ester, MS Calc.: 559.0 Found: 558.2 (M−1).

EXAMPLE 5-10

N-{3,5-Dichloro-4-[4-hydroxy-3-(naphthalene-2-sulfonyl)-phenoxy]-phenyl}-oxamic acid, MS Calc.: 559.0 Found: 558.2 (M−1).

EXAMPLE 5-11

N-{3,5-Dichloro-4-[4-hydroxy-3-(toluene-4-sulfonyl)-phenoxy]-phenyl}-oxamic acid, MS Calc.: 495.0 Found: 494.1 (M−1).

EXAMPLE 5-12

N-{3,5-Dichloro-4-[4-hydroxy-3-(toluene-4-sulfonyl)-phenoxy]-phenyl}-oxamide, MS Calc.: 494.0 Found: 493.0 (M−1).

EXAMPLE 6

N-[3,5-Dichloro-4-(3-cyclopropylmethanesulfonyl-4-hydroxy-phenoxy)-phenyl]-oxamic acid ethyl ester

Step A

On cooling with an ice bath, 2',6'-dichloro-4-methoxy-4'-nitrodiphenyl ether (5 g, 16 mmol) was added portionwise to chlorosulfonic acid (14 g, 120 mmol). The resulting reddish-brown solution was allowed to warm to RT and stirred at RT for 1 h. The reaction mixture was added dropwise into ice water (200 mL), extracted with EtOAc (3×200 mL), dried and concentrated to give a tan solid. The solid was added in portions to a solution of $Na_2SO_3$ (6 g, 48 mmol) in $H_2O$ (12 mL). The solution was made basic by addition of 32% aqueous NaOH and the pH was adjusted to 9.0. After stirring at 65° C. for 2 h then at 25° C. for 19 h, the solution was acidified with 1N HCl and a precipitate formed. The precipitate was collected by filtration, washed with water and dried to afford the product. MS Calc.: 377.0 Found: 376.1 (M−1).

Step B

To a solution of sodium ethoxide (0.29 mmol) in EtOH at RT was added 2-methoxy-4-(2',6'-dichloro-4'-nitro-phenoxy)-benzenesulfinic acid (100 mg, 0.26 mmol), the product of Step A, and cyclopropylmethyl bromide (143 mg, 1.1 mmol). The resulting mixture was stirred at reflux for 18 h and cooled to RT. To the solution was added 1N HCl (5 mL), followed by extraction with EtOAc (3×10 mL). The combined extracts were dried and concentrated. The crude product was purified by preparative TLC (EtOAc:Hex, 1:1) to give a solid. MS Calc.: 431.0, Found: 431.0 (M).

Step C

The title compound of this EXAMPLE 6 can be prepared from the product of Step B via demethylation, hydrogenation, and oxamate formation according to procedures analogous to those described in EXAMPLE 1. NMR (400 MHz, CDCl$_3$) d 8.93(s, 1H), 8.68 (s, 1H), 7.75 (s, 2H), 7.10–7.13 (m, 1H), 6.96–6.99 (m, 2H), 4.41 (q, 2H), 3.01 (d, 2H), 1.41 (t, 3H), 0.95–0.99 (m, 1H), 0.54–0.58 (m, 2H), 0.11–0.14 (m, 2H). MS Calc.: 487.0 Found: 485.9 (M–1).

Using the appropriate starting materials, EXAMPLES 6-1 to 6-13 were prepared in an analogous manner to that described in EXAMPLE 6.

EXAMPLE 6-1

N-[4-(4-Hydroxy-3-methanesulfonyl-phenoxy)-3,5-dimethyl-phenyl]-oxamic acid, MS Calc.: 379.1 Found: 378.2 (M–1).

EXAMPLE 6-2

N-[3,5-Dichloro-4-(3-ethanesulfonyl-4-hydroxy-phenoxy)-phenyl]-oxamic acid, MS Calc.: 433.0 Found: 432.0 (M–1).

EXAMPLE 6-3

N-{3,5-Dichloro-4-[4-hydroxy-3-(propane-2-sulfonyl)-phenoxy]-phenyl}-oxamic acid ethyl ester, MS Calc.: 475.0 Found: 474.0 (M–1).

EXAMPLE 6-4

N-[3,5-Dichloro-4-(3-cyclobutylmethanesulfonyl-4-hydroxy-phenoxy)-phenyl]-oxamic acid ethyl ester, MS Calc.: 501.0 Found: 499.9 (M–1).

EXAMPLE 6-5

N-[3,5-Dichloro-4-(3-cyclohexylmethanesulfonyl-4-hydroxy-phenoxy)-phenyl]-oxamic acid ethyl ester, MS Calc.: 529.1 Found: 528.0 (M–1).

EXAMPLE 6-6

N-[3,5-Dichloro-4-(3-cyclopentanesulfonyl-4-hydroxy-phenoxy)-phenyl]-oxamic acid ethyl ester, MS Calc.: 501.0 Found: 499.9 (M–1).

EXAMPLE 6-7

N-{4-[3-(Butane-1-sulfonyl)-4-hydroxy-phenoxy]-3,5-dichloro-phenyl}-oxamic acid, MS Calc.: 461.0 Found: 460.2 (M–1).

EXAMPLE 6-8

N-[3,5-Dichloro-4-(4-hydroxy-3-phenylmethanesulfonyl-phenoxy)-phenyl]-oxamic acid, MS Calc.: 495.0 Found: 493.9 (M–1).

EXAMPLE 6-9

N-{3,5-Dichloro-4-[4-hydroxy-3-(propane-1-sulfonyl)-phenoxy]-phenyl}-oxamic acid, MS Calc.: 447.0 Found: 446.0 (M–1).

EXAMPLE 6-10

N-{3,5-Dichloro-4-[3-(4-fluoro-phenylmethanesulfonyl)-4-hydroxy-phenoxy]-phenyl}-oxamic acid, MS Calc.: 513.0 Found: 512.0 (M–1).

EXAMPLE 6-11

N-[3,5-Dichloro-4-(3-cyclopropylmethanesulfonyl-4-hydroxy-phenoxy)-phenyl]-oxamic acid, MS Calc.: 459.0 Found: 458.2 (M–1).

EXAMPLE 6-12

N-[3,5-Dichloro-4-(3-cyclobutylmethanesulfonyl-4-hydroxy-phenoxy)-phenyl]-oxamic acid, MS Calc.: 473.0 Found: 472.2 (M–1).

EXAMPLE 6-13

N-[4-(3-Cyclopropylmethanesulfonyl-4-hydroxy-phenoxy)-3,5-dimethyl-phenyl]-oxamic acid, MS Calc.: 419.1 Found: 418.0 (M–1).

EXAMPLE 7

4-(3-Phenoxy-4-methoxyphenoxy)-3,5-dimethylnitrobenzene

Step A

To a cooled (0° C.), stirred solution of 3-benzyloxy-4-methoxybenzaldehyde (10 g) in MeOH (100 mL) was added hydrogen peroxide (5.5 mL of 30% aqueous) dropwise. After having been warmed to RT, concentrated sulfuric acid (1 mL) was added and the resulting solution was allowed to stir for 1.5 h. The reaction mixture was partitioned between ethyl ether/saturated aqueous sodium bicarbonate, another organic layer was dried over sodium sulfate and concentrated in vacuo to afford an oil. Flash chromatography (20% ethyl acetate/hexanes) afforded 3-benzyloxy-4-methoxyphenol (5.8 g).

Step B

To a solution of 3-benzyloxy-4-methoxyphenol (3 g) in DMSO (2 mL) was added potassium t-butoxide (1.6 g). After 30 min, 4-chloro-3,5-dimethylnitrobenzene (2 g) was added and the resulting solution was heated at 80° C. for 2 h. The reaction mixture was partitioned between ethyl acetate and 1N aqueous NaOH, and the organic layer was washed with water, brine, dried over sodium sulfate and concentrated in vacuo to afford 4-(3-benzyloxy-4-methoxyphenoxy)-3,5-dimethylnitrobenzene (1.9 g) as an orange solid.

Step C

A solution of 4-(3-benzyloxy-4-methoxyphenoxy)-3,5-dimethylnitrobenzene (1.65 g), TFA (3.5 mL) and thioanisole (2.2 mL) were stirred for 4 h. The reaction was partitioned between ethyl acetate and water, the organic layer dried over sodium sulfate and concentrated in vacuo. Flash chromatography afforded 4-(3-hydroxy-4-methoxyphenoxy)-3,5-dimethylnitrobenzene (1.2 g) as a yellow oil.

Step D

A solution of 4-(3-hydroxy-4-methoxyphenoxy)-3,5-dimethylnitrobenzene (150 mg), phenylboronic acid (190 mg), copper (II) acetate (189 mg) and TEA (0.22 mL) in dichloromethane (4 mL) was stirred for 6 h. The reaction was diluted into ethyl acetate, washed with 1N hydrochloric acid, dried over sodium sulfate and concentrated in vacuo. The resulting oil was flash chromatographed (10% DEE/petroleum ether) to afford 4-(3-phenoxy-4- methoxyphenoxy)-3,5-dimethylnitrobenzene (130 mg) as a colorless solid.

Using the appropriate starting materials, EXAMPLES 7-1 to 7-9 were prepared in an analogous manner to that described in EXAMPLE 7.

EXAMPLE 7-1

N-[3,5-Dichloro-4-(4-hydroxy-3-phenoxy-phenoxy)-phenyl-oxamic acid ethyl ester, MS found: 460.

EXAMPLE 7-2

N-{3,5-Dichloro-4-[3-(4-chloro-phenoxy)-4-hydroxy-phenoxy]-phenyl}-oxamic acid ethyl ester, MS found: 495.

EXAMPLE 7-3

N-{3,5-Dichloro-4-[3-(4-chloro-phenoxy)-4-hydroxy-phenoxy]-phenyl}-oxamic acid, MS found: 467.

EXAMPLE 7-4

N-[3,5-Dichloro-4-(4-hydroxy-3-phenoxy-phenoxy)-phenyl]-oxamic acid, MS found: 432.

EXAMPLE 7-5

N-{3,5-Dichloro-4-[3-(4-fluoro-phenoxy)-4-hydroxy-phenoxy]-phenyl}-oxamic acid ethyl ester, MS found: 478.

EXAMPLE 7-6

N-{3,5-Dichloro-4-[3-(4-fluoro-phenoxy)-4-hydroxy-phenoxy]-phenyl}-oxamic acid, MS found: 450.

EXAMPLE 7-7

N-{4-[3-(4-Fluoro-phenoxy)-4-hydroxy-phenoxy]-3,5-dimethyl-phenyl}-oxamic acid, MS found: 410.

EXAMPLE 7-8

N-[4-(4-Hydroxy-3-phenoxy-phenoxy)-3,5-dimethyl-phenyl]-oxamic acid, MS found: 392.

EXAMPLE 7-9

N-{4-[3-(4-Chloro-phenoxy)-4-hydroxy-phenoxy]-3,5-dimethyl-phenyl}-oxamic acid, MS found: 426.

EXAMPLE 8

2,2-Dimethyl-7-hydroxy-4-methoxyindane

Step A

To a cooled (0° C.), stirred solution of 4,7-dimethoxyindan-1-one (1 g) in THF (20 mL) was added lithium hexamethyldisilizane (6.2 mL of a 1M solution in THF). After 45 min, methyl iodide (0.4 mL) was added and the resulting mixture was allowed to stir at RT for 3 h.

Step B

After stirring at RT, following the addition of the first equivalent of methyl iodide, the reaction mixture was recooled to 0° C. and an additional portion of lithium hexamethyidisilizane (6.2 mL) was added. After 45 min, methyl iodide (0.4 mL) was added and the resulting mixture was allowed to stir at RT for 3 h. The reaction was quenched with saturated aqueous ammonium chloride, extracted with ethyl acetate, the organic layer dried over sodium sulfate and concentrated to a dark oil. Flash chromatography (hexanes:chloroform) afforded 2,2-dimethyl-4,7-dimethoxyindan-1-one (1.0 g) as a brown oil.

Step C

To a cooled (−78° C.), stirred solution of 2,2-dimethyl-4,7-dimethoxy-indan-1-one (1 g) in dichloromethane (20 mL) was added boron trichloride (9 mL of a 1M solution in dichloromethane) over a 5 min period. The reaction was allowed to warm to RT, stirred for 3 h, then recooled to −78° C., quenched with ice, allowed to warm to RT and stirred for 1 h. The reaction was extracted with dichloromethane, the organic layers dried over sodium sulfate, concentrated in vacuo and flash chromatographed to afford 2,2-dimethyl-7-hydroxy-4-methoxyindan-1-one (0.85 g) as a tan oil.

Step D

To a stirred solution of 2,2-dimethyl-7-hydroxy-4-methoxyindan-1-one (500 mg) and methanesulfonic acid (466 mg) in dichloromethane (12 mL) was added triethylsilane (564 mg). Every 0.5 h, over a 3 h period, additional portions of methanesulfonic acid and triethylsilane were added. The reaction was partitioned between water and dichloromethane, the organic layer dried over sodium sulfate, concentrated in vacuo and the resulting oil flash chromatographed (1:1, chloroform:hexanes) to afford 2,2-dimethyl-7-hydroxy-4-methoxyindane (230 mg) as a colorless waxy solid.

Using the appropriate starting materials, EXAMPLES 8-1 to 8-8 were prepared using methods analogous to those described in EXAMPLE 8 and by SCHEMES K and L.

EXAMPLE 8-1

N-[3-Chloro-4-(7-hydroxy-2,2-dimethyl-indan-4-yloxy)-5-methyl-phenyl]-oxamic acid, melting point found: 226–229° C. (dec).

EXAMPLE 8-2

N-[4-(7-Hydroxy-indan-4-yloxy)-3,5-dimethyl-phenyl]-oxamic acid, MS Found: 340.

EXAMPLE 8-3

N-[3-Chloro-4-(7-hydroxy-indan-4-yloxy)-5-methyl-phenyl]-oxamic acid, MS Found: 360.

EXAMPLE 8-4

N-[4-(7-Hydroxy-indan-4-yloxy)-3,5-dimethyl-phenyl]-oxamic acid ethyl ester, MS Found: 368.

EXAMPLE 8-5

N-[4-(7-Hydroxy-indan-4-yloxy)-3,5-dimethyl-phenyl]-oxamide, MS Found: 339.

EXAMPLE 8-6

N-[3-Chloro-4-(7-hydroxy-indan-4-yloxy)-5-methyl-phenyl]-oxamide, MS Found: 360.

EXAMPLE 8-7

N-[3-Chloro-4-(4-hydroxy-5,6,7,8-tetrahydro-naphthalen-1-yloxy)-5-methyl-phenyl]-oxamic acid, MS Found: 374.

EXAMPLE 8-8

N-[3-Chloro-4-(4-hydroxy-5,6,7,8-tetrahydro-naphthalen-1-yloxy)-5-methyl-phenyl]-oxamide, MS Found: 373.

EXAMPLE 9

N-{3-Chloro-4-[3-(4-fluoro-phenoxymethyl)-4-hydroxy-phenoxy]-5-methyl-phenyl}-oxamic acid ethyl ester

Step A

To a cooled (−78° C.), stirred solution of 5-(2-chloro-6-methyl-4-nitro-phenoxy)-2-methoxy-benzaldehyde (10 g) in dichloromethane (300 mL) was added boron tribromide (23.3 g) dropwise. The reaction was allowed to warm to ambient temperature, stirred for 1.5 h, ice was added to quench the reaction and work up was done with ethyl acetate/water. The organic layer was dried over sodium sulfate, concentrated in vacuo and the resulting oil filtered through a plug of silica gel (eluting with chloroform) to afford 5-(2-chloro-6-methyl-4-nitro-phenoxy)-2-hydroxy-benzaldehyde (8.65 g) as an off-white solid.

Step B

To a cooled (0° C.), stirred solution of 5-(2-chloro-6-methyl-4-nitro-phenoxy)-2-hydroxy-benzaldehyde (8.6 g) in DMF (130 mL) was added sodium hydride (1.3 g of 60% in oil), the cooling bath was removed after 5 min and the thick mixture allowed to stir at RT for 45 min. Trimethyl-siloxyethoxymethyl chloride (5.59 g) was added and stirring was continued for 16 h. The reaction was quenched with half-saturated ammonium chloride, extracted with ethyl acetate, the combined organic layers dried over sodium sulfate and concentrated in vacuo to afford a brown oil. Flash chromatography (10–20% ethyl acetate:hexanes) afforded 5-(2-chloro-6-methyl-4-nitro-phenoxy)-2-(2-trimethylsilanyl-ethoxymethoxy)-benzaldehyde (12.1 g) as an off-white solid.

Step C

To a cooled (−78° C.), stirred solution of 5-(2-chloro-6-methyl-4-nitro-phenoxy)-2-(2-trimethylsilanyl-ethoxymethoxy)-benzaldehyde (10 g) in THF (200 mL) was added diisobutylaluminum hydride (46 mL of a 1M solution in THF). After 30 min, 0.5M sodium potassium tartrate (100 mL) was added and the resulting mixture was allowed to warm to RT. Extraction with ethyl acetate, drying over sodium sulfate and concentration in vacuo afforded [5-(2-chloro-6-methyl-4-nitro-phenoxy)-2-(2-trimethylsilanyl-ethoxymethoxy)-phenyl]-MeOH (10.6 g), which was taken on to Step D without further purification.

Step D

To a solution of [5-(2-chloro-6-methyl-4-nitro-phenoxy)-2-(2-trimethylsilanyl-ethoxymethoxy)-phenyl]-MeOH (250 mg), triphenyl-phosphine (300 mg) and p-fluorophenol (95 mg) was added 1,1'-(azodicarbonyl)dipiperdine (214 mg). After 18 h, hexanes were added, solids filtered, washed with further portions of hexanes and the filtrate was concentrated in vacuo. Residue was flash chromatographed (hexanes-2% ethyl acetate/hexanes) to afford {2-[4-(2-chloro-6-methyl-4-nitro-phenoxy)-2-(4-fluoro-phenoxymethyl)-phenoxymethoxy]-ethyl}-trimethylsilane (300 mg) as an oil.

Step E

To a stirred solution of {2-[4-(2-chloro-6-methyl-4-nitro-phenoxy)-2-(4-fluoro-phenoxymethyl)-phenoxymethoxy]-ethyl}-trimethylsilane (280 mg) in MeOH (2.5 mL)/THF (0.2 mL) was added 6% sulfuric acid in MeOH (2.5 mL) and the resulting solution was stirred for 1 h. The reaction was quenched with 1N aqueous sodium bicarbonate, extracted with ethyl acetate, the organic layer dried over sodium sulfate and concentrated in vacuo. Flash chromatography (15% ethyl acetatelhexanes) afforded 4-(2-chloro-6-methyl-4-nitro-phenoxy)-2-(4-fluorophen-oxymethyl)-phenol (170 mg) as a yellow semi-solid.

Step F

To a warm (100° C.) solution of 4-(2-chloro-6-methyl-4-nitro-phenoxy)-2-(4-fluorophenoxymethyl)-phenol (100 mg) in glacial acetic acid (2.5 mL) was added zinc dust (243 mg) and heating was continued for 30 min. The reaction mixture was cooled, diluted with ethyl acetate and filtered through Celite®. The filtrate was washed with 1M aqueous sodium bicarbonate, dried over sodium sulfate, concentrated in vacuo and flashed chromatographed (30% ethyl acetate/hexanes) to afford 4-(4-amino-2-chloro-6-methyl-phenoxy)-2-(4-fluoro-phenoxymethyl)-phenol (90 mg) as a tan solid.

Step G

A solution of 4-(4-amino-2-chloro-6-methyl-phenoxy)-2-(4-fluoro-phenoxy-methyl)-phenol (90 mg) in diethyloxy-late (1 mL) was heated at 125° C. for 18 h. The resulting solution was flash chromatographed (30% ethyl acetate/hexanes) to afford N-{3-chloro-4-[3-(4-fluoro-phenoxymethyl)-4-hydroxy-phenoxy]-5-methyl-phenyl}-oxamic acid ethyl ester (70 mg).

Using the appropriate starting materials, EXAMPLE 9-1 was prepared in an analogous manner to that described in EXAMPLE 9.

EXAMPLE 9-1

N-[3-Chloro-4-(4-hydroxy-3-phenoxymethyl-phenoxy)-5-methyl-phenyl]-oxamic acid ethyl ester, MS Found: 454.

EXAMPLE 10

N-[3,5-Dichloro-4-(1H-indol-5-yloxy)-phenyl]-oxamic acid ethyl ester

Step A

Potassium carbonate (0.71 g, 5.12 mmol) was added to a solution of 5-hydroxyindole (0.62 g, 4.66 mmol) and 3,5-dichloro-4-iodonitrobenzene (1.48 g, 4.66 mmol) in N-methylpyrrolidone (10 mL). The resulting mixture was stirred at 125° C. for 3 h and cooled to RT. The mixture was poured into 1N HCl (100 mL) and extracted with $CH_2Cl_2$ (3×25 mL). The combined organic extracts were washed with 1N HCl (2×50 mL), $H_2O$ (3×100 mL), brine (1×100 mL), and then dried and concentrated. The residue was purified by preparative TLC (35% $CH_2Cl_2$ in hexanes) to give a yellow solid. MS Calc.: 322 Found: 321.2. (M−1).

Step B

The title compound of EXAMPLE 10 was prepared from the product of Step A via hydrogenation and oxamate formation. MS Calc.: 392.0 Found: 391.2. (M−1).

Using the appropriate starting materials, EXAMPLES 10-1 to 10-7 were prepared in an analogous manner to that described in EXAMPLE 10.

EXAMPLE 10-1

N-[3,5-Dichloro-4-(1H-indol-5-yloxy)-phenyl]-oxamic acid ethyl ester, MS Calc.: 392.0 Found: 391.2. (M−1).

EXAMPLE 10-2

N-[3,5-Dichloro-4-(1H-indol-5-yloxy)-phenyl]-oxamic acid, MS Calc.: 364.0 Found: 363.1 (M−1).

EXAMPLE 10-3

N-[3,5-Dichloro-4-(1H-indol-5-yloxy)-phenyl]-oxamide, MS Calc.: 372.1 Found: 371.2 (M−1).

EXAMPLE 10-4

N-[3-Chloro-4-(1H-indol-5-yloxy)-5-methyl-phenyl]-oxamic acid, MS Calc.: 344.1 Found: 343.2 (M−1).

EXAMPLE 10-5

N-[3-Chloro-4-(1H-indol-5-yloxy)-5-methyl-phenyl]-oxamide, MS Calc.: 343.1 Found: 342.2 (M−1).

EXAMPLE 10-6

N-[3,5-Dichloro-4-(2-methyl-1H-indol-5-yloxy)-phenyl]-oxamic acid ethyl ester, MS Calc.: 406.0 Found: 405.2 (M−1).

EXAMPLE 10-7

N-[3,5-Dichloro-4-(2-methyl-1H-indol-5-yloxy)-phenyl]-oxamic acid, MS Calc.: 378.0 Found: 377.1 (M−1).

EXAMPLE 11

N-[3,5-Dichloro-4-(4-fluoro-3-methyl-phenoxy)-phenyl]-oxamic acid

Step A

A mixture of 3-methyl-4-fluorophenol (99 mg, 0.79 mmol), potassium hydroxide (53 mg, 0.94 mmol), 4-iodo-3,5-dichloro-nitrobenzene (250 mg, 0.79 mmol) and 4A° molecular sieves (75 mg) in N-methylpyrolidinone (3 mL) was stirred at 130° C. for 2 h. The reaction mixture was poured into ice cold 1 N HCl (20 mL) and EtOAc (25 mL) was added. The EtOAc phase was separated and washed with 1N HCl (3×25 mL) and brine (25 mL). The EtOAc solution was dried over $Na_2SO_4$, filtered and concentrated. The residue was purified by preparative TLC (Hexanes: $CH_2Cl_2$=7:3) to afford 3,5-dichloro-4-(4-fluoro-3-methyl-phenoxy)-nitrobenzene (207 mg). MS Calc.: 315.0 Found: 315.0 (M).

Step B

N-[3,5-Dichloro-4-(4-fluoro-3-methyl-phenoxy)-phenyl]-oxamic acid ethyl ester was prepared from 3,5-dichloro-4-(4-fluoro-3-methyl-phenoxy)-nitrobenzene via hydrogenation and acylation. MS Calc.: 385.0 Found: 384.0 (M−1).

Step C

N-[3,5-Dichloro-4-(4-fluoro-3-methyl-phenoxy)-phenyl]-oxamic acid was prepared from N-[3,5-dichloro-4-(4-fluoro-3-methyl-phenoxy)-phenyl]-oxamic acid ethyl ester via hydrolysis. MS Calc.: 357.0 Found: 356.2 (M−1).

Using the appropriate starting materials, EXAMPLES 11-1 to 11-13 were prepared in an analogous manner to that described in EXAMPLE 11.

EXAMPLE 11-1

N-[4-(4-Fluoro-phenoxy)-3,5-dimethyl-phenyl]-oxamic acid, MS Calc.: 303.1 Found: 302.2 (M−1).

EXAMPLE 11-2

N-[3,5-Dichloro-4-(4-fluoro-phenoxy)-phenyl]-oxamic acid ethyl ester, MS Calc.: 371.0 Found: 369.9 (M−1).

EXAMPLE 11-3

N-[3,5-Dichloro-4-(3,4-difluoro-phenoxy)-phenyl]-oxamic acid ethyl ester, MS Calc.: 389.0 Found: 387.9 (M−1).

EXAMPLE 11-4

N-[3,5-Dichloro-4-(3-chloro-4-fluoro-phenoxy)-phenyl]-oxamic acid ethyl ester, MS Calc.: 405.0 Found: 403.9 (M−1).

EXAMPLE 11-5

N-[4-(3,4-Difluoro-phenoxy)-3,5-dimethyl-phenyl]-oxamic acid, MS Calc.: 321.1 Found: 320.1 (M−1).

EXAMPLE 11-6

N-[4-(3-Chloro-4-fluoro-phenoxy)-3,5-dimethyl-phenyl]-oxamic acid, MS Calc.: 337.1 Found: 335.9 (M−1).

EXAMPLE 11-7

N-[4-(4-Fluoro-3-methyl-phenoxy)-3,5-dimethyl-phenyl]-oxamic acid, MS Calc.: 317.1 Found: 316.1 (M−1).

EXAMPLE 11-8

N-[3,5-Dichloro-4-(4-fluoro-phenoxy)-phenyl]-oxamic acid, MS Calc.: 343.0 Found: 342.1 (M−1).

EXAMPLE 11-9

N-[3,5-Dichloro-4-(3,4-difluoro-phenoxy)-phenyl]-oxamic acid, MS Calc.: 361.0 Found: 360.1 (M−1).

EXAMPLE 11-10

N-[3,5-Dichloro-4-(3-chloro-4-fluoro-phenoxy)-phenyl]-oxalamic acid, MS Calc.: 376.9 Found: 376.1 (M−1).

EXAMPLE 11-11

N-{4-[3-(Cyclobutyl-methyl-carbamoyl)-4-fluoro-phenoxy]-3,5-dimethyl-phenyl}-oxalamic acid ethyl ester, MS Calc.: 442.2 Found: 441.1 (M−1).

EXAMPLE 11-12

N-{4-[3-(Cyclobutyl-methyl-carbamoyl)-4-fluoro-phenoxy]-3,5-dimethyl-phenyl}-oxalamic acid, MS Calc.: 414.2 Found: 413.3 (M−1).

EXAMPLE 11-13

N-[4-(4-Fluoro-phenoxy)-3,5-dimethyl-phenyl]-oxalamic acid ethyl ester, MS Calc.: 331.1 Found: 330.2 (M−1).

What is claimed is:
1. A compound of the Formula

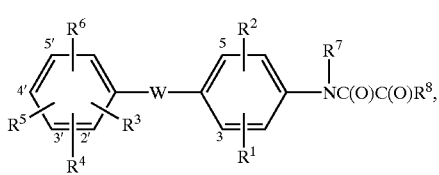

(I)

a prodrug thereof, a geometric or optical isomer thereof, or a pharmaceutically acceptable salt of said compound, said prodrug, or said isomer, wherein:

$R^1$, $R^2$ and $R^3$ are each independently hydrogen, halogen, $C_{1-6}$ alkyl, trifluoromethyl, —CN, —OCF$_3$ or —OC$_{1-6}$ alkyl;

$R^4$ is hydrogen, $C_{1-12}$ alkyl optionally substituted with one to three substituents independently selected from Group Z, $C_{2-12}$ alkenyl, halogen, —CN, aryl, heteroaryl, $C_{3-10}$ cycloalkyl, heterocycloalkyl, —S(O)$_2$NR$^9$R$^{10}$, —C(O)NR$^9$R$^{10}$, —(C$_{1-6}$ alkyl)-NR$^9$R$^{10}$, —NR$^9$C(O)R$^{10}$, —NR$^9$C(O)NR$^9$R$^{10}$, —NR$^9$S(O)$_2$R$^{10}$, —(C$_{1-6}$ alkyl)-OR$^{11}$, —OR$^{11}$ or —S(O)$_a$R$^{12}$, provided that, where $R^5$ is not fluoro, $R^4$ is —S(O)$_2$NR$^9$R$^{10}$, —C(O)NR$^9$R$^{10}$, —(C$_{1-6}$ alkyl)-NR$^9$R$^{10}$, —NR$^9$C(O)R$^{10}$, —NR$^9$C(O)NR$^9$R$^{10}$, —NR$^9$S(O)$_2$R$^{10}$, —(C$_{1-6}$ alkyl)-OR$^{11}$, —OR$^{11}$ or —S(O)$_a$R$^{12}$;

$R^5$ is fluoro, hydroxy, $C_{1-4}$ alkoxy or OC(O)R$^9$;

or $R^4$ and $R^5$ may be taken together to form a heterocyclic ring B selected from the group consisting of —CR$^9$=CR$^{10}$—NH—, —N=CR$^9$—NH—, —CR$^9$=CH—O— and —CR$^9$=CH—S—;

$R^6$ is hydrogen, halogen, $C_{1-4}$ alkyl or trifluoromethyl;

$R^7$ is hydrogen or $C_{1-6}$ alkyl;

$R^8$ is —OR$^9$ or —NR$^{19}$R$^{20}$;

$R^9$ and $R^{10}$ for each occurrence are independently (A) hydrogen, (B) $C_{1-12}$ alkyl optionally substituted with one or more substituents independently selected from Group V, (C) $C_{2-12}$ alkenyl, (D) $C_{3-10}$ cycloalkyl optionally substituted with one or more substituents independently selected from $C_{1-6}$ alkyl, $C_{2-5}$ alkynyl, $C_{3-10}$ cycloalkyl, —CN, —NR$^{13}$R$^{14}$, oxo, —OR$^{18}$, —COOR$^{18}$ or aryl optionally substituted with X and Y, (E) aryl optionally substituted with X and Y, or (F) het optionally substituted with X and Y;

or $R^9$ and $R^{10}$ for any occurrence may be taken together to form a heterocyclic ring C optionally further containing a second heterogroup selected from the group consisting of —O—, —NR$^{13}$— and —S—, and optionally further substituted with one or more substituents independently selected from $C_{1-5}$ alkyl, oxo, —NR$^{13}$R$^{14}$, —OR$^{18}$, —C(O)$_2$R$^{18}$, —CN, —C(O)R$^9$, aryl optionally substituted with X and Y, het optionally substituted with X and Y, $C_{5-6}$ spirocycloalkyl, and a carbocyclic ring B selected from the group consisting of 5-, 6-, 7- and 8-membered partially and fully saturated, and unsaturated carbocyclic rings, and including any bicyclic group in which said carbocyclic ring B is fused to a carbocyclic ring C selected from the group consisting of 5-, 6-, 7- and 8-membered partially and fully saturated, and unsaturated carbocyclic rings;

$R^{11}$ is $C_{1-12}$ alkyl optionally substituted with one or more substituents independently selected from Group V, $C_{2-12}$ alkenyl, $C_{3-10}$ cycloalkyl, trifluoromethyl, difluoromethyl, monofluoromethyl, aryl optionally substituted with X and Y, het optionally substituted with X and Y, —C(O)NR$^9$R$^{10}$ or —C(O)R$^9$;

$R^{12}$ is $C_{1-12}$ alkyl optionally substituted with one or more substituents independently selected from Group V, $C_{2-12}$ alkenyl, $C_{3-10}$ cycloalkyl, aryl optionally substituted with X and Y, or het optionally substituted with X and Y;

$R^{13}$ and $R^{14}$ for each occurrence are independently hydrogen, $C_{1-6}$ alkyl, $C_{2-6}$ alkenyl, —(C$_{1-6}$ alkyl)-C$_{1-6}$ alkoxy, aryl optionally substituted with X and Y, het optionally substituted with X and Y, —(C$_{1-4}$ alkyl)-aryl optionally substituted with X and Y, —(C$_{1-4}$ alkyl)-heterocycle optionally substituted with X and Y, —(C$_{1-4}$ alkyl)-hydroxy, —(C$_{1-4}$ alkyl)-halo, —(C$_{1-4}$ alkyl)-poly-halo, —(C$_{1-4}$ alkyl)-CONR$^{15}$R$^{16}$ or $C_{3-10}$ cycloalkyl;

$R^{15}$ and $R^{16}$ for each occurrence are independently hydrogen, $C_{1-6}$ alkyl, $C_{3-10}$ cycloalkyl or aryl optionally substituted with X and Y;

$R^{18}$ is hydrogen, $C_{1-6}$ alkyl, $C_{2-6}$ alkenyl, —(C$_{1-6}$ alkyl)-C$_{1-6}$ alkoxy, aryl optionally substituted with X and Y, het optionally substituted with X and Y, —(C$_{1-4}$ alkyl)-aryl optionally substituted with X and Y, —(C$_{1-4}$ alkyl)-heterocycle optionally substituted with X and Y, —(C$_{1-4}$ alkyl)-hydroxy, —(C$_{1-4}$ alkyl)-halo, —(C$_{1-4}$ alkyl)-poly-halo, —(C$_{1-4}$ alkyl)-CONR$^{15}$R$^{16}$, —(C$_{1-4}$ alkyl)-(C$_{1-4}$ alkoxy) or $C_{3-10}$ cycloalkyl;

$R^{19}$ is hydrogen or $C_{1-6}$ alkyl;

$R^{20}$ is hydrogen or $C_{1-6}$ alkyl;

W is O, S(O)$_d$, CH$_2$ or NR$^9$;

Group Z is $C_{2-6}$ alkenyl, $C_{2-6}$ alkynyl, halogen, —CF$_3$, —OCF$_3$, hydroxy, oxo, —CN, aryl, heteroaryl, $C_{3-10}$ cycloalkyl, hetercycloalkyl, —S(O)$_a$R$^{12}$, —S(O)$_2$NR$^9$R$^{10}$, —C(O)R$^9$R$^{10}$, and —NR$^9$R$^{10}$;

Group V is halogen, —NR$^{13}$R$^{14}$, —OCF$_3$, —OR$^9$, oxo, trifluoromethyl, —CN, $C_{3-10}$ cycloalkyl, aryl optionally substituted with X and Y, and het optionally substituted with X and Y;

het for each occurrence is a heterocyclic ring D selected from the group consisting of 4-, 5-, 6-, 7- and 8-membered partially and fully saturated, and unsaturated, heterocyclic rings containing from one to four heteroatoms independently selected from the group consisting of N, O and S, and including any bicyclic group in which said heterocyclic ring D is fused to a benzene ring or a heterocyclic ring E selected from the group consisting of 4-, 5-, 6-, 7- and 8-membered partially and fully saturated, and unsaturated, heterocyclic rings containing from one to four heteroatoms independently selected from the group consisting of N, O and S;

X and Y for each occurrence are independently (A) hydrogen, (B) halogen, (C) trifluoromethyl, (D) —OCF$_3$, (E) —CN, (F) $C_{1-6}$ alkyl optionally substituted with one or more substituents independently selected from the group consisting of halogen, —OCF$_3$, —CF$_3$ and phenyl, (G) $C_{1-6}$ alkoxy, (H) aryl optionally substituted with one or more substituents independently selected from the group consisting of halogen, —OCF$_3$, —CF$_3$, $C_{1-4}$ alkyl and $C_{1-4}$ alkoxy, (I) —C(O)$_2$R$^{13}$, (J) —C(O)NR$^{13}$R$^{14}$, (K) —C(O)R$^{13}$, (L) —NR$^{13}$C(O)NR$^{13}$R$^{14}$ and (M) —NR$^{13}$C(O)R$^{14}$;

or X and Y for any occurrence in the same variable may be taken together to form (a) a carbocyclic ring D of the formula —(CH$_2$)$_e$— or (b) a heterocyclic ring F selected from the group consisting of —O(CH$_2$)$_f$O—, (CH$_2$)$_g$NH— and —CH=CHNH—;

a and d are each independently 0, 1 or 2;

f and g are each independently 2, 3, 4, 5 or 6; and e is 3, 4, 5, 6 or 7.

2. A compound or pharmaceutically acceptable salt as defined in claim 1 wherein W is oxygen.

3. A compound or pharmaceutically acceptable salt as defined in claim 2 wherein R$^1$ is located at the 3 position, R$^2$ is located at the 5 position, R$^3$ is located at the 2' position, R$^4$ is located at the 3' position, R$^5$ is located at the 4' position, and R$^6$ is located at the 5' position.

4. A compound or pharmaceutically acceptable salt as defined in claim 1 wherein R$^1$ and R$^2$ are each independently methyl, bromo or chloro, and R$^8$ is hydroxy, methoxy, ethoxy, isopropoxy, NH$_2$ or NH(CH$_3$).

5. A compound or pharmaceutically acceptable salt as defined in claim 4 wherein R$^4$ is S(O)$_2$NR$^9$R$^{10}$, and R$^{10}$ is hydrogen or methyl.

6. A compound or pharmaceutically acceptable salt as defined in claim 5 wherein R$^1$ is chloro, R$^2$ is methyl, R$^8$ is ethoxy, R$^9$ is ethyl and R$^{10}$ is hydrogen.

7. A compound or pharmaceutically acceptable salt as defined in claim 5 wherein R$^1$ is chloro, R$^2$ is methyl, R$^8$ is hydroxy, R$^9$ is ethyl and R$^{10}$ is hydrogen.

8. A compound or pharmaceutically acceptable salt as defined in claim 5 wherein R$^1$ is chloro, R$^2$ is methyl, R$^8$ is ethoxy, R$^9$ is n-butyl and R$^{10}$ is hydrogen.

9. A compound or pharmaceutically acceptable salt as defined in claim 5 wherein R$^1$ is chloro, R$^2$ is methyl, R$^8$ is hydroxy, R$^9$ is n-butyl and R$^{10}$ is hydrogen.

10. A compound or pharmaceutically acceptable salt as defined in claim 5 wherein R$^1$ is chloro, R$^2$ is methyl, R$^8$ is ethoxy, R$^9$ is —CH$_2$-cyclopropyl and R$^{10}$ is hydrogen.

11. A compound or pharmaceutically acceptable salt as defined in claim 5 wherein R$^1$ is chloro, R$^2$ is methyl, R$^8$ is hydroxy, R$^9$ is —CH$_2$-cyclopropyl and R$^{10}$ is hydrogen.

12. A compound or pharmaceutically acceptable salt as defined in claim 5 wherein R$^1$ is chloro, R$^2$ is methyl, R$^8$ is isopropoxy, R$^9$ is cyclopropyl and R$^{10}$ is hydrogen.

13. A compound or pharmaceutically acceptable salt as defined in claim 5 wherein R$^1$ is chloro, R$^2$ is methyl, R$^8$ is hydroxy, R$^9$ is cyclopropyl and R$^{10}$ is hydrogen.

14. A compound or pharmaceutically acceptable salt as defined in claim 4 wherein R$^4$ is S(O)$_2$NR$^9$R$^{10}$, and R$^9$ and R$^{10}$ are taken together with the nitrogen atom to which they are attached to form N(CH$_2$)$_4$, N(CH$_2$)$_5$, morpholine or

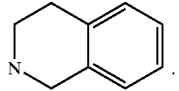

15. A compound or pharmaceutically acceptable salt as defined in claim 14 wherein R$^9$ and R$^{10}$ are taken together with the nitrogen atom to which they are attached to form N(CH$_2$)$_4$.

16. A compound or pharmaceutically acceptable salt as defined in claim 14 wherein R$^9$ and R$^{10}$ are taken together with the nitrogen atom to which they are attached to form

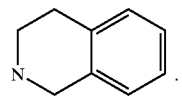

17. A compound or pharmaceutically acceptable salt as defined in claim 5 wherein R$^9$ is hydrogen, isopropyl, —CH$_2$-2-thienyl, —CH$_2$-cyclopropyl, cyclopropyl, —(CH$_2$)$_2$OH, exo-2-norbornyl, methyl, ethyl, 4-fluorophenyl, cyclobutyl, cyclopentyl, cyclohexyl, n-propyl, n-butyl, n-pentyl, n-hexyl, n-octyl or n-decyl.

18. A compound or pharmaceutically acceptable salt as defined in claim 17 wherein R$^1$ is chloro, R$^2$ is methyl, R$^8$ is hydroxy, R$^9$ is cyclopropyl and R$^{10}$ is hydrogen.

19. A compound or pharmaceutically acceptable salt as defined in claim 17 wherein R$^1$ is chloro, R$^2$ is methyl, R$^8$ is ethoxy, R$^9$ is cyclopropyl and R$^{10}$ is hydrogen.

20. A compound or pharmaceutically acceptable salt as defined in claim 17 wherein R$^1$ is methyl, R$^2$ is methyl, R$^8$ is hydroxy, R$^9$ is cyclopropyl and R$^{10}$ is methyl.

21. A compound or pharmaceutically acceptable salt as defined in claim 17 wherein R$^1$ is methyl, R$^2$ is methyl, R$^8$ is ethoxy, R$^9$ is cyclopropyl and R$^{10}$ is methyl.

22. A compound or pharmaceutically acceptable salt as defined in claim 17 wherein R$^1$ is methyl, R$^2$ is methyl, R$^8$ is hydroxy, R$^9$ is cyclobutyl and R$^{10}$ is methyl.

23. A compound or pharmaceutically acceptable salt as defined in claim 17 wherein R$^1$ is methyl, R$^2$ is methyl, R$^8$ is ethoxy, R$^9$ is cyclobutyl and R$^{10}$ is methyl.

24. A compound or pharmaceutically acceptable salt as defined in claim 17 wherein R$^1$ is methyl, R$^2$ is methyl, R$^8$ is hydroxy, R$^9$ is cyclopropyl and R$^{10}$ is hydrogen.

25. A compound or pharmaceutically acceptable salt as defined in claim 17 wherein R$^1$ is methyl, R$^2$ is methyl, R$^8$ is ethoxy, R$^9$ is cyclopropyl and R$^{10}$ is hydrogen.

26. A compound or pharmaceutically acceptable salt as defined in claim 17 wherein R$^1$ is methyl, R$^2$ is methyl, R$^8$ is hydroxy, R$^9$ is cyclobutyl and R$^{10}$ is hydrogen.

27. A compound or pharmaceutically acceptable salt as defined in claim 17 wherein R$^1$ is methyl, R$^2$ is methyl, R$^8$ is ethoxy, R$^9$ is cyclobutyl and R$^{10}$ is hydrogen.

28. A compound or pharmaceutically acceptable salt as defined in claim 4 wherein R$^4$ is —C(O)NR$^9$R$^{10}$, and R$^{10}$ is hydrogen, methyl or ethyl.

29. A compound or pharmaceutically acceptable salt as defined in claim 28 wherein R$^9$ is methyl, ethyl, isopropyl, n-propyl, isobutyl, n-butyl, n-pentyl, n-hexyl, 4-fluorophenyl, —CH$_2$-2-thienyl, cyclopropyl, —CH$_2$-cyclopropyl, cyclobutyl, cyclopentyl, cyclohexyl, —CH$_2$-cyclohexyl, endo-2-norbornyl, exo-2-norbornyl, (S)-1-phenylethyl, (R)-1-phenylethyl, —CH$_2$-2-chlorophenyl, —CH$_2$-4-chlorophenyl, —CH$_2$-4-fluorophenyl, —CH$_2$-3-chloro-4-fluorophenyl, —CH$_2$-2-chloro-4-fluorophenyl, —CH$_2$-2-fluoro-4-chlorophenyl, —CH$_2$-3,4-difluorophenyl, —CH$_2$-4-isopropylphenyl, —CH$_2$-2,3-dichlorophenyl, —CH$_2$-2,4-dichlorophenyl, —CH$_2$-3,4-dichlorophenyl, —CH$_2$-3-trifluoromethyl-4-chlorophenyl, 4-phenylphenyl, 3-(2,4-dimethyl)pentyl, (R)-1-(1-naphthyl)ethyl, 1,1-dimethylpropyl, 1,2-dimethylpropyl, 2,2-dimethylpropyl, (R)-1-(2-naphthyl)ethyl, (R)-2-(1-naphthyl)ethyl, —CH$_2$-(1-naphthyl), (R)-1-cyclohexylethyl, (S)-1-cyclohexylethyl, —CH$_2$-3,4-methylenedioxyphenyl, —CH$_2$-4-t-butylphenyl, —CH$_2$-2,3-dichlorophenyl, 1-indanyl, (R)-1-indanyl, (S)-1-indanyl, 5-indanyl, 1-(1,2,3,4-tetrahydronaphthyl) or (R)-1-cyclohexylethyl.

30. A compound or pharmaceutically acceptable salt as defined in claim 29 wherein R$^1$ is chloro, R$^2$ is chloro, R$^8$ is ethoxy, R$^9$ is 3-(2,4-dimethyl)pentyl and R$^{10}$ is hydrogen.

31. A compound or pharmaceutically acceptable salt as defined in claim 29 wherein $R^1$ is chloro, $R^2$ is chloro, $R^8$ is hydroxy, $R^9$ is 3-(2,4-dimethyl)pentyl and $R^{10}$ is hydrogen.

32. A compound or pharmaceutically acceptable salt as defined in claim 29 wherein $R^1$ is methyl, $R^2$ is methyl, $R^8$ is hydroxy, $R^9$ is cyclopropyl and $R^{10}$ is methyl.

33. A compound or pharmaceutically acceptable salt as defined in claim 29 wherein $R^1$ is methyl, $R^2$ is methyl, $R^8$ is ethoxy, $R^9$ is cyclopropyl and $R^{10}$ is methyl.

34. A compound or pharmaceutically acceptable salt as defined in claim 29 wherein $R^1$ is methyl, $R^2$ is methyl, $R^8$ is hydroxy, $R^9$ is cyclobutyl and $R^{10}$ is methyl.

35. A compound or pharmaceutically acceptable salt as defined in claim 29 wherein $R^1$ is methyl, $R^2$ is methyl, $R^8$ is ethoxy, $R^9$ is cyclobutyl and $R^{10}$ is methyl.

36. A compound or pharmaceutically acceptable salt as defined in claim 29 wherein $R^1$ is methyl, $R^2$ is methyl, $R^8$ is hydroxy, $R^9$ is 3-(2,4-dimethyl)pentyl and $R^{10}$ is hydrogen.

37. A compound or pharmaceutically acceptable salt as defined in claim 29 wherein $R^1$ is methyl, $R^2$ is methyl, $R^8$ is ethoxy, $R^9$ is 3-(2,4-dimethyl)pentyl and $R^{10}$ is hydrogen.

38. A compound or pharmaceutically acceptable salt as defined in claim 29 wherein $R^1$ is methyl, $R^2$ is methyl, $R^8$ is hydroxy, $R^9$ is n-pentyl and $R^{10}$ is methyl.

39. A compound or pharmaceutically acceptable salt as defined in claim 29 wherein $R^1$ is methyl, $R^2$ is methyl, $R^8$ is ethoxy, $R^9$ is n-pentyl and $R^{10}$ is methyl.

40. A compound or pharmaceutically acceptable salt as defined in claim 29 wherein $R^1$ is methyl, $R^2$ is methyl, $R^8$ is hydroxy, $R^9$ is isopropyl and $R^{10}$ is methyl.

41. A compound or pharmaceutically acceptable salt as defined in claim 29 wherein $R^1$ is methyl, $R^2$ is methyl, $R^8$ is ethoxy, $R^9$ is isopropyl and $R^{10}$ is methyl.

42. A compound or pharmaceutically acceptable salt as defined in claim 29 wherein $R^1$ is methyl, $R^2$ is methyl, $R^8$ is hydroxy, $R^9$ is cyclobutyl and $R^{10}$ is methyl.

43. A compound or pharmaceutically acceptable salt as defined in claim 29 wherein $R^1$ is methyl, $R^2$ is methyl, $R^8$ is ethoxy, $R^9$ is cyclobutyl and $R^{10}$ is methyl.

44. A compound or pharmaceutically acceptable salt as defined in claim 29 wherein $R^1$ is methyl, $R^2$ is methyl, $R^8$ is $NH_2$, $R^9$ is cyclobutyl and $R^{10}$ is methyl.

45. A compound or pharmaceutically acceptable salt as defined in claim 29 wherein $R^1$ is chloro, $R^2$ is chloro, $R^8$ is hydroxy, $R^9$ is cyclobutyl and $R^{10}$ is methyl.

46. A compound or pharmaceutically acceptable salt as defined in claim 29 wherein $R^1$ is chloro, $R^2$ is chloro, $R^8$ is ethoxy, $R^9$ is cyclobutyl and $R^{10}$ is methyl.

47. A compound or pharmaceutically acceptable salt as defined in claim 1 wherein $R^4$ is —C(O)$NR^9R^{10}$, and $R^9$ and $R^{10}$ are taken together with the nitrogen atom to which they are attached to form $N(CH_2)_7$, $N(CH_2)_6$, $N(CH_2)_5$, $N(CH_2)_4$, morpholine,

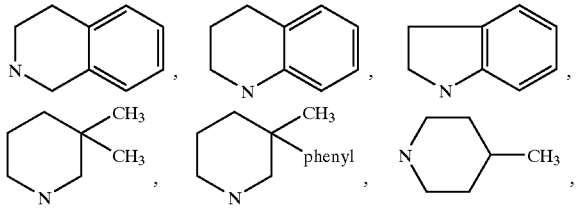

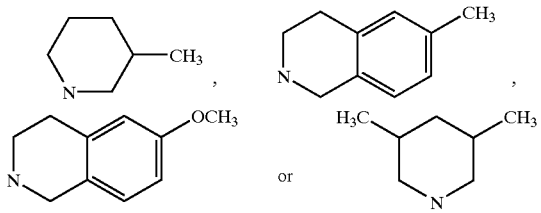

48. A compound or pharmaceutically acceptable salt as defined in claim 4 wherein $R^4$ is —$CH_2NR^9R^{10}$, and $R^{10}$ is hydrogen, methyl or —$COCH_3$.

49. A compound or pharmaceutically acceptable salt as defined in claim 48 wherein $R^9$ is methyl, n-propyl, isopropyl, cyclopropyl, cyclobutyl, cyclopentyl, cyclohexyl, exo-2-norbornyl, —$CH_2$-4-fluorophenyl, —$CH_2$-4-chlorophenyl, —$CH_2$-4-isopropylphenyl, —$CH_2$-3,4-methylenedioxyphenyl, (R)-1-(1-naphthyl)ethyl, (R)-1-phenylethyl, (S)-1-phenylethyl, (R)-1-cyclohexylethyl, 1-(1,2,3,4-tetrahydronaphthyl), 1-indanyl or —$CH_2$-(1-naphthyl).

50. A compound or pharmaceutically acceptable salt as defined in claim 4 wherein $R^4$ is —$CH_2NR^9R^{10}$ wherein $R^9$ and $R^{10}$ are taken together with the nitrogen atom to which they are attached to form $N(CH_2)_6$, morpholine,

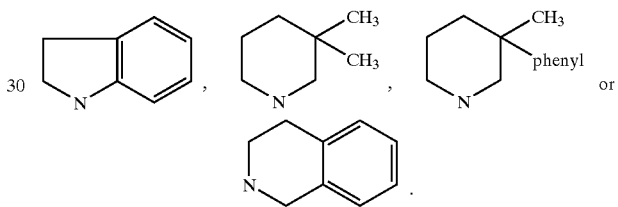

51. A compound or pharmaceutically acceptable salt as defined in claim 4 wherein $R^4$ is —$NHCOR^9$.

52. A compound or pharmaceutically acceptable salt as defined in claim 51 wherein $R^9$ is cyclopropyl or cyclobutyl.

53. A compound or pharmaceutically acceptable salt as defined in claim 4 wherein $R^4$ is —$S(O)_2R^{12}$.

54. A compound or pharmaceutically acceptable salt as defined in claim 53 wherein $R^{12}$ is 4-chlorophenyl, phenyl, 1-naphthyl, 2-naphthyl, $CH_2$-cyclopropyl, isopropyl, $CH_2$-cyclobutyl, $CH_2$-cyclohexyl, cyclopentyl, $CH_2$-4-fluorophenyl, 4-tolyl, methyl, ethyl, n-butyl, $CH_2$-phenyl or n-propyl.

55. A compound or pharmaceutically acceptable salt as defined in claim 54 wherein $R^1$ is chloro, $R^2$ is chloro, $R^8$ is hydroxy and $R^{12}$ is ethyl.

56. A compound or pharmaceutically acceptable salt as defined in claim 54 wherein $R^1$ is chloro, $R^2$ is chloro, $R^8$ is ethoxy and $R^{12}$ is ethyl.

57. A compound or pharmaceutically acceptable salt as defined in claim 54 wherein $R^1$ is chloro, $R^2$ is chloro, $R^8$ is hydroxy and $R^{12}$ is —$CH_2$-cyclobutyl.

58. A compound or pharmaceutically acceptable salt as defined in claim 54 wherein $R^1$ is chloro, $R^2$ is chloro, $R^8$ is hydroxy and $R^{12}$ is —$CH_2$-cyclobutyl.

59. A compound or pharmaceutically acceptable salt as defined in claim 54 wherein $R^1$ is chloro, $R^2$ is chloro, $R^8$ is hydroxy and $R^{12}$ is —$CH_2$-cyclohexyl.

60. A compound or pharmaceutically acceptable salt as defined in claim 54 wherein $R^1$ is chloro, $R^2$ is chloro, $R^8$ is ethoxy and $R^{12}$ is —$CH_2$-cyclohexyl.

61. A compound or pharmaceutically acceptable salt as defined in claim 54 wherein $R^1$ is chloro, $R^2$ is chloro, $R^8$ is hydroxy and $R^{12}$ is cyclopentyl.

62. A compound or pharmaceutically acceptable salt as defined in claim 54 wherein $R^1$ is chloro, $R^2$ is chloro, $R^8$ is ethoxy and $R^{12}$ is cyclopentyl.

63. A compound or pharmaceutically acceptable salt as defined in claim 54 wherein $R^1$ is chloro, $R^2$ is chloro, $R^8$ is hydroxy, and $R^{12}$ is —$CH_2$-cyclopropyl.

64. A compound or pharmaceutically acceptable salt as defined in claim 54 wherein $R^1$ is chloro, $R^2$ is chloro, $R^8$ is ethoxy, and $R^{12}$ is —$CH_2$-cyclopropyl.

65. A compound or pharmaceutically acceptable salt as defined in claim 54 wherein $R^1$ is chloro, $R^2$ is chloro, $R^8$ is hydroxy, and $R^{12}$ is —$CH_2$-cyclobutyl.

66. A compound or pharmaceutically acceptable salt as defined in claim 54 wherein $R^1$ is chloro, $R^2$ is chloro, $R^8$ is ethoxy, and $R^{12}$ is —$CH_2$-cyclobutyl.

67. A compound or pharmaceutically acceptable salt as defined in claim 54 wherein $R^1$ is methyl, $R^2$ is methyl, $R^8$ is hydroxy, and $R^{12}$ is —$CH_2$-cyclopropyl.

68. A compound or pharmaceutically acceptable salt as defined in claim 54 wherein $R^1$ is methyl, $R^2$ is methyl, $R^8$ is ethoxy, and $R^{12}$ is —$CH_2$-cyclopropyl.

69. A compound or pharmaceutically acceptable salt as defined in claim 3 wherein $R^1$ and $R^2$ are each independently methyl, bromo or chloro, $R^3$ is hydrogen, $R^4$ and $R^5$ are taken together to form $R^6$ is hydrogen, $R^7$ is hydrogen, $R^8$ is ethoxy, hydroxy or $NH_2$, and $R^{10}$ is hydrogen or methyl.

70. A compound or pharmaceutically acceptable salt as defined in claim 4 wherein $R^3$ is hydrogen, and $R^4$ is —$OR^{11}$.

71. A compound or pharmaceutically acceptable salt as defined in claim 70 wherein $R^{11}$ is phenyl, 4-chlorophenyl or 4-fluorophenyl.

72. A compound or pharmaceutically acceptable salt as defined in claim 4 wherein $R^3$ is hydrogen, and $R^4$ is —($C_{1-6}$ alkyl)-$OR^{11}$.

73. A compound or pharmaceutically acceptable salt as defined in claim 72 wherein $R^4$ is —$CH_2$—$OR^{11}$.

74. A compound or pharmaceutically acceptable salt as defined in claim 73 wherein $R^{11}$ is phenyl or 4-fluorophenyl.

75. A compound or pharmaceutically acceptable salt as defined in claim 1 wherein $R^8$ is —$OR^9$.

76. A compound or pharmaceutically acceptable salt as defined in claim 75 wherein $R^9$ is $C_{1-12}$ alkyl.

77. A compound or pharmaceutically acceptable salt as defined in claim 76 wherein $R^9$ is methyl.

78. A compound or pharmaceutically acceptable salt as defined in claim 76 wherein $R^9$ is ethyl.

79. A compound or pharmaceutically acceptable salt as defined in claim 76 wherein $R^9$ is isopropyl.

80. A pharmaceutically acceptable salt as defined in claim 1 wherein said salt is a potassium salt.

81. A pharmaceutically acceptable salt as defined in claim 1 wherein said salt is a sodium salt.

82. A compound as defined in claim 1 selected from the group consisting of:
N-[3-chloro-4-(3-cyclopropylsulfamoyl-4-hydroxy-phenoxy)-5-methyl-phenyl]-oxamic acid,
N-[4-(3-cyclopropylsulfamoyl-4-hydroxy-phenoxy)-3,5-dimethyl-phenyl]-oxamic acid,
N-{4-[3-(cyclobutyl-methyl-carbamoyl)-4-hydroxy-phenoxy]-3,5-dimethyl-phenyl}-oxamic acid,
N-{3-chloro-4-[3-(cyclobutyl-methyl-carbamoyl)-4-hydroxy-phenoxy]-5-methyl-phenyl}-oxamic acid,
N-{3,5-dichloro-4-[3-(cyclobutyl-methyl-carbamoyl)-4-hydroxy-phenoxy]-phenyl}-oxamic acid,
N-[3,5-dichloro-4-(3-cyclopentanesulfonyl-4-hydroxy-phenoxy)-phenyl]-oxamic acid,
N-[3,5-dichloro-4-(3-cyclopropylmethanesulfonyl-4-hydroxy-phenoxy)-phenyl]-oxamic acid,
N-[3,5-dichloro-4-(3-cyclobutylmethanesulfonyl-4-hydroxy-phenoxy)-phenyl]-oxamic acid,
N-[4-(3-cyclopropylmethanesulfonyl-4-hydroxy-phenoxy)-3,5-dimethyl-phenyl]-oxamic acid,
N-[3-chloro-4-(3-cyclobutylmethanesulfonyl-4-hydroxy-phenoxy)-5-methyl-phenyl]-oxamic acid,
N-[4-(3-cyclobutylmethanesulfonyl-4-hydroxy-phenoxy)-3,5-dimethyl-phenyl]-oxamic acid,
N-[4-(3-cyclopentylmethanesulfonyl-4-hydroxy-phenoxy)-3,5-dimethyl-phenyl]-oxamic acid,
N-[3-chloro-4-(3-cyclopentylmethanesulfonyl-4-hydroxy-phenoxy)-5-methyl-phenyl]-oxamic acid,
N-[3,5-dichloro-4-(3-cyclopentylmethanesulfonyl-4-hydroxy-phenoxy)-phenyl]-oxamic acid,
N-[4-(3-cyclohexylmethanesulfonyl-4-hydroxy-phenoxy)-3,5-dimethyl-phenyl]-oxamic acid,
N-[3-chloro-4-(3-cyclohexylmethanesulfonyl-4-hydroxy-phenoxy)-5-methyl-phenyl]-oxamic acid,
N-[3,5-dichloro-4-(3-cyclohexylmethanesulfonyl-4-hydroxy-phenoxy)-phenyl]-oxamic acid,
N-[3,5-dichloro-4-[3-(4-fluoro-benzenesulfonyl)-4-hydroxy-phenoxy)-phenyl]-oxamic acid,
N-{4-[3-(4-fluoro-benzenesulfonyl)-4-hydroxy-phenoxy]-3,5-dimethyl-phenyl}-oxamic acid and
N-{3-chloro-4-[3-(4-fluoro-benzenesulfonyl)-4-hydroxy-phenoxy]-5-methyl-phenyl}-oxamic acid.

83. A pharmaceutically acceptable salt of each of said compounds as defined in claim 82 wherein said salt is a potassium salt.

84. A pharmaceutically acceptable salt of each of said compounds as defined in claim 82 wherein said salt is a sodium salt.

85. A compound as defined in claim 1 selected from the group consisting of
N-[3-chloro-4-(3-cyclopropylsulfamoyl-4-hydroxy-phenoxy)-5-methyl-phenyl]-oxamic acid methyl ester,
N-[4-(3-cyclopropylsulfamoyl-4-hydroxy-phenoxy)-3,5-dimethyl-phenyl]-oxamic acid methyl ester,
N-{4-[3-(cyclobutyl-methyl-carbamoyl)-4-hydroxy-phenoxy]-3,5-dimethyl-phenyl}-oxamic acid methyl ester,
N-{3-chloro-4-[3-(cyclobutyl-methyl-carbamoyl)-4-hydroxy-phenoxy]-5-methyl-phenyl}-oxamic acid methyl ester,
N-{3,5-dichloro-4-[3-(cyclobutyl-methyl-carbamoyl)-4-hydroxy-phenoxy]-phenyl}-oxamic acid methyl ester,
N-[3,5-dichloro-4-(3-cyclopentanesulfonyl-4-hydroxy-phenoxy)-phenyl]-oxamic acid methyl ester,
N-[3,5-dichloro-4-(3-cyclopropylmethanesulfonyl-4-hydroxy-phenoxy)-phenyl]-oxamic acid methyl ester,
N-[3,5-dichloro-4-(3-cyclobutylmethanesulfonyl-4-hydroxy-phenoxy)-phenyl]-oxamic acid methyl ester,
N-[4-(3-cyclopropylmethanesulfonyl-4-hydroxy-phenoxy)-3,5-dimethyl-phenyl]-oxamic acid methyl ester,
N-[3-chloro-4-(3-cyclobutylmethanesulfonyl-4-hydroxy-phenoxy)-5-methyl-phenyl]-oxamic acid methyl ester,
N-[4-(3-cyclobutylmethanesulfonyl-4-hydroxy-phenoxy)-3,5-dimethyl-phenyl]-oxamic acid methyl ester, N-[4-(3-cyclopentylmethanesulfonyl-4-hydroxy-phenoxy)-3,5-dimethyl-phenyl]-oxamic acid methyl ester,
N-[3-chloro-4-(3-cyclopentylmethanesulfonyl-4-hydroxy-phenoxy)-5-methyl-phenyl]-oxamic acid methyl ester,
N-[3,5-dichloro-4-(3-cyclopentylmethanesulfonyl-4-hydroxy-phenoxy)-phenyl]-oxamic acid methyl ester,
N-[4-(3-cyclohexylmethanesulfonyl-4-hydroxy-phenoxy)-3,5-dimethyl-phenyl]-oxamic acid methyl ester,
N-[3-chloro-4-(3-cyclohexylmethanesulfonyl-4-hydroxy-phenoxy)-5-methyl-phenyl]-oxamic acid methyl ester,
N-[3,5-dichloro-4-(3-cyclohexylmethanesulfonyl-4-hydroxy-phenoxy)-phenyl]-oxamic acid methyl ester,
N-[3,5-dichloro-4-[3-(4-fluoro-benzenesulfonyl)-4-hydroxy-phenoxy)-phenyl]-oxamic acid methyl ester,
N-{4-[3-(4-fluoro-benzenesulfonyl)-4-hydroxy-phenoxy]-3,5-dimethyl-phenyl}-oxamic acid methyl ester and
N-{3-chloro-4-[3-(4-fluoro-benzenesulfonyl)-4-hydroxy-phenoxy]-5-methyl-phenyl}-oxamic acid methyl ester.

86. A compound as defined in claim 1 selected from the group consisting of
N-[3-chloro-4-(3-cyclopropylsulfamoyl-4-hydroxy-phenoxy)-5-methyl-phenyl]-oxamic acid ethyl ester,
N-[4-(3-cyclopropylsulfamoyl-4-hydroxy-phenoxy)-3,5-dimethyl-phenyl]-oxamic acid ethyl ester,
N-{4-[3-(cyclobutyl-methyl-carbamoyl)-4-hydroxy-phenoxy]-3,5-dimethyl-phenyl}-oxamic acid ethyl ester,
N-{3-chloro-4-[3-(cyclobutyl-methyl-carbamoyl)-4-hydroxy-phenoxy]-5-methyl-phenyl}-oxamic acid ethyl ester,
N-{3,5-dichloro-4-[3-(cyclobutyl-methyl-carbamoyl)-4-hydroxy-phenoxy]-phenyl}-oxamic acid ethyl ester,
N-[3,5-dichloro-4-(3-cyclopentanesulfonyl-4-hydroxy-phenoxy)-phenyl]-oxamic acid ethyl ester,
N-[3,5-dichloro-4-(3-cyclopropylmethanesulfonyl-4-hydroxy-phenoxy)-phenyl]-oxamic acid ethyl ester,
N-[3,5-dichloro-4-(3-cyclobutylmethanesulfonyl-4-hydroxy-phenoxy)-phenyl]-oxamic acid ethyl ester,
N-[4-(3-cyclopropylmethanesulfonyl-4-hydroxy-phenoxy)-3,5-dimethyl-phenyl]-oxamic acid ethyl ester,
N-[3-chloro-4-(3-cyclobutylmethanesulfonyl-4-hydroxy-phenoxy)-5-methyl-phenyl]-oxamic acid ethyl ester,
N-[4-(3-cyclobutylmethanesulfonyl-4-hydroxy-phenoxy)-3,5-dimethyl-phenyl]-oxamic acid ethyl ester,
N-[4-(3-cyclopentylmethanesulfonyl-4-hydroxy-phenoxy)-3,5-dimethyl-phenyl]-oxamic acid ethyl ester,
N-[3-chloro-4-(3-cyclopentylmethanesulfonyl-4-hydroxy-phenoxy)-5-methyl-phenyl]-oxamic acid ethyl ester,
N-[3,5-dichloro-4-(3-cyclopentylmethanesulfonyl-4-hydroxy-phenoxy)-phenyl]-oxamic acid ethyl ester,
N-[4-(3-cyclohexylmethanesulfonyl-4-hydroxy-phenoxy)-3,5-dimethyl-phenyl]-oxamic acid ethyl ester,
N-[3-chloro-4-(3-cyclohexylmethanesulfonyl-4-hydroxy-phenoxy)-5-methyl-phenyl]-oxamic acid ethyl ester,
N-[3,5-dichloro-4-(3-cyclohexylmethanesulfonyl-4-hydroxy-phenoxy)-phenyl]-oxamic acid ethyl ester,
N-[3,5-dichloro-4-[3-(4-fluoro-benzenesulfonyl)-4-hydroxy-phenoxy)-phenyl]-oxamic acid ethyl ester,
N-{4-[3-(4-fluoro-benzenesulfonyl)-4-hydroxy-phenoxy]-3,5-dimethyl-phenyl}-oxamic acid ethyl ester and
N-{3-chloro-4-[3-(4-fluoro-benzenesulfonyl)-4-hydroxy-phenoxy]-5-methyl-phenyl}-oxamic acid ethyl ester.

87. A compound as defined in claim 1 selected from the group consisting of
N-[3-chloro-4-(3-cyclopropylsulfamoyl-4-hydroxy-phenoxy)-5-methyl-phenyl]-oxamic acid isopropyl ester,
N-[4-(3-cyclopropylsulfamoyl-4-hydroxy-phenoxy)-3,5-dimethyl-phenyl]-oxamic acid isopropyl ester,
N-{4-[3-(cyclobutyl-methyl-carbamoyl)-4-hydroxy-phenoxy]-3,5-dimethyl-phenyl}-oxamic acid isopropyl ester,
N-{3-chloro-4-[3-(cyclobutyl-methyl-carbamoyl)-4-hydroxy-phenoxy]-5-methyl-phenyl}-oxamic acid isopropyl ester,
N-{3,5-dichloro-4-[3-(cyclobutyl-methyl-carbamoyl)-4-hydroxy-phenoxy]-phenyl}-oxamic acid isopropyl ester,
N-[3,5-dichloro-4-(3-cyclopentanesulfonyl-4-hydroxy-phenoxy)-phenyl]-oxamic acid isopropyl ester,
N-[3,5-dichloro-4-(3-cyclopropylmethanesulfonyl-4-hydroxy-phenoxy)-phenyl]-oxamic acid isopropyl ester,
N-[3,5-dichloro-4-(3-cyclobutylmethanesulfonyl-4-hydroxy-phenoxy)-phenyl]-oxamic acid isopropyl ester,
N-[4-(3-cyclopropylmethanesulfonyl-4-hydroxy-phenoxy)-3,5-dimethyl-phenyl]-oxamic acid isopropyl ester,
N-[3-chloro-4-(3-cyclobutylmethanesulfonyl-4-hydroxy-phenoxy)-5-methyl-phenyl]-oxamic acid isopropyl ester,
N-[4-(3-cyclobutylmethanesulfonyl-4-hydroxy-phenoxy)-3,5-dimethyl-phenyl]-oxamic acid isopropyl ester,
N-[4-(3-cyclopentylmethanesulfonyl-4-hydroxy-phenoxy)-3,5-dimethyl-phenyl]-oxamic acid isopropyl ester,
N-[3-chloro-4-(3-cyclopentylmethanesulfonyl-4-hydroxy-phenoxy)-5-methyl-phenyl]-oxamic acid isopropyl ester,
N-[3,5-dichloro-4-(3-cyclopentylmethanesulfonyl-4-hydroxy-phenoxy)-phenyl]-oxamic acid isopropyl ester,
N-[4-(3-cyclohexylmethanesulfonyl-4-hydroxy-phenoxy)-3,5-dimethyl-phenyl]-oxamic acid isopropyl ester,
N-[3-chloro-4-(3-cyclohexylmethanesulfonyl-4-hydroxy-phenoxy)-5-methyl-phenyl]-oxamic acid isopropyl ester,
N-[3,5-dichloro-4-(3-cyclohexylmethanesulfonyl-4-hydroxy-phenoxy)-phenyl]-oxamic acid isopropyl ester,
N-[3,5-dichloro-4-[3-(4-fluoro-benzenesulfonyl)-4-hydroxy-phenoxy)-phenyl]-oxamic acid isopropyl ester,
N-{4-[3-(4-fluoro-benzenesulfonyl)-4-hydroxy-phenoxy]-3,5-dimethyl-phenyl}-oxamic acid isopropyl ester and
N-{3-chloro-4-[3-(4-fluoro-benzenesulfonyl)-4-hydroxy-phenoxy]-5-methyl-phenyl}-oxamic acid isopropyl ester.

88. A compound as defined in claim 1 selected from the group consisting of
N-{3,5-dichloro-4-[4-hydroxy-3-(pyrrolidine-1-sulfonyl)-phenoxy]-phenyl}-oxamic acid,
N-[4-(3-cyclopropylsulfamoyl-4-hydroxy-phenoxy)-3,5-dimethyl-phenyl]-oxamic acid ethyl ester,
N-[4-(4-hydroxy-3-methylsulfamoyl-phenoxy)-3,5-dimethyl-phenyl]-oxamic acid ethyl ester,
N-{4-[3-(4-fluoro-phenylsulfamoyl)-4-hydroxy-phenoxy]-3,5-dimethyl-phenyl}-oxamic acid ethyl ester,
N-[4-(3-dimethylsulfamoyl-4-hydroxy-phenoxy)-3,5-dimethyl-phenyl]-oxamic acid ethyl ester,
N-{4-[3-(cyclopropyl-methyl-sulfamoyl)-4-hydroxy-phenoxy]-3,5-dimethyl-phenyl}-oxamic acid ethyl ester,
N-{4-[3-(cyclobutyl-methyl-sulfamoyl)-4-hydroxy-phenoxy]-3,5-dimethyl-phenyl}-oxamic acid ethyl ester,
N-[4-(3-cyclobutylsulfamoyl-4-hydroxy-phenoxy)-3,5-dimethyl-phenyl]-oxamic acid ethyl ester,
N-[4-(3-cyclopentylsulfamoyl-4-hydroxy-phenoxy)-3,5-dimethyl-phenyl]-oxamic acid ethyl ester,
N-{4-[4-hydroxy-3-(pyrrolidine-1-sulfonyl)-phenoxy]-3,5-dimethyl-phenyl}-oxamic acid ethyl ester,
N-{4-[4-hydroxy-3-(piperidine-1-sulfonyl)-phenoxy]-3,5-dimethyl-phenyl}-oxamic acid ethyl ester,
N-[4-(3-cyclohexylsulfamoyl-4-hydroxy-phenoxy)-3,5-dimethyl-phenyl]-oxamic acid ethyl ester,
N-[4-(4-hydroxy-3-propylsulfamoyl-phenoxy)-3,5-dimethyl-phenyl]-oxamic acid ethyl ester,
N-[4-(3-butylsulfamoyl-4-hydroxy-phenoxy)-3,5-dimethyl-phenyl]-oxamic acid ethyl ester, N-{4-[3-(cyclopropyl-methyl-sulfamoyl)-4-hydroxy-phenoxy]-3,5-dimethyl-phenyl}-oxamic acid,
N-{4-[3-(cyclobutyl-methyl-sulfamoyl)-4-hydroxy-phenoxy]-3,5-dimethyl-phenyl}-oxamic acid,
N-[4-(3-cyclopropylsulfamoyl-4-hydroxy-phenoxy)-3,5-dimethyl-phenyl]-oxamic acid,
N-[4-(3-cyclobutylsulfamoyl-4-hydroxy-phenoxy)-3,5-dimethyl-phenyl]-oxamic acid,
N-[3-chloro-4-(3-cyclopropylsulfamoyl-4-hydroxy-phenoxy)-5-methyl-phenyl]-oxamic acid ethyl ester,
N-[3-chloro-4-(3-cyclobutylsulfamoyl-4-hydroxy-phenoxy)-5-methyl-phenyl]-oxamic acid ethyl ester,
N-[3-chloro-4-(3-cyclopentylsulfamoyl-4-hydroxy-phenoxy)-5-methyl-phenyl]-oxamic acid ethyl ester,
N-[3-chloro-4-(3-cyclohexylsulfamoyl-4-hydroxy-phenoxy)-5-methyl-phenyl]-oxamic acid ethyl ester,
N-[3-chloro-4-(4-hydroxy-3-sulfamoyl-phenoxy)-5-methyl-phenyl]-oxamic acid ethyl ester,
N-{3-chloro-4-[4-hydroxy-3-(piperidine-1-sulfonyl)-phenoxy]-5-methyl-phenyl}-oxamic acid ethyl ester,
N-{3-chloro-4-[3-(4-fluoro-phenylsulfamoyl)-4-hydroxy-phenoxy]-5-methyl-phenyl}-oxamic acid ethyl ester,
N-[3-chloro-4-(3-dimethylsulfamoyl-4-hydroxy-phenoxy)-5-methyl-phenyl]-oxamic acid ethyl ester,
N-[3-chloro-4-(4-hydroxy-3-methylsulfamoyl-phenoxy)-5-methyl-phenyl]-oxamic acid ethyl ester,
N-[3-chloro-4-(4-hydroxy-3-propylsulfamoyl-phenoxy)-5-methyl-phenyl]-oxamic acid ethyl ester,
N-[3-chloro-4-(4-hydroxy-3-pentylsulfamoyl-phenoxy)-5-methyl-phenyl]-oxamic acid ethyl ester,
N-[3-chloro-4-(3-hexylsulfamoyl-4-hydroxy-phenoxy)-5-methyl-phenyl]-oxamic acid ethyl ester,
N-[3-chloro-4-(4-hydroxy-3-octylsulfamoyl-phenoxy)-5-methyl-phenyl]-oxamic acid ethyl ester,
N-[3-chloro-4-(3-decylsulfamoyl-4-hydroxy-phenoxy)-5-methyl-phenyl]-oxamic acid ethyl ester,
N-[4-(3-butylsulfamoyl-4-hydroxy-phenoxy)-3-chloro-5-methyl-phenyl]-oxamic acid ethyl ester,
N-{3-chloro-4-[3-(ethyl-methyl-sulfamoyl)-4-hydroxy-phenoxy]-5-methyl-phenyl}-oxamic acid ethyl ester,
N-{3-chloro-4-[4-hydroxy-3-(methyl-propyl-sulfamoyl)-phenoxy]-5-methyl-phenyl}-oxamic acid ethyl ester,
N-{4-[3-(butyl-methyl-sulfamoyl)-4-hydroxy-phenoxy]-3-chloro-5-methyl-phenyl}-oxamic acid ethyl ester,
N-{3-chloro-4-[4-hydroxy-3-(morpholine-4-sulfonyl)-phenoxy]-5-methyl-phenyl}-oxamic acid ethyl ester,
N-{3-chloro-4-[3-(cyclopropylmethyl-sulfamoyl)-4-hydroxy-phenoxy]-5-methyl-phenyl}-oxamic acid ethyl ester,
N-{3-chloro-4-[4-hydroxy-3-(2-hydroxy-ethylsulfamoyl)-phenoxy]-5-methyl-phenyl}-oxamic acid ethyl ester,
N-[3-chloro-4-(3-cyclopropylsulfamoyl-4-hydroxy-phenoxy)-5-methyl-phenyl]-oxamic acid isopropyl ester,
N-[3-chloro-4-(3-cyclopropylsulfamoyl-4-hydroxy-phenoxy)-5-methyl-phenyl]-oxamic acid,
N-[3-chloro-4-(3-cyclobutylsulfamoyl-4-hydroxy-phenoxy)-5-methyl-phenyl]-oxamic acid,
N-[3-chloro-4-(3-cyclopentylsulfamoyl-4-hydroxy-phenoxy)-5-methyl-phenyl]-oxamic acid,
N-[3-chloro-4-(3-cyclohexylsulfamoyl-4-hydroxy-phenoxy)-5-methyl-phenyl]-oxamic acid,
N-[3-chloro-4-(4-hydroxy-3-sulfamoyl-phenoxy)-5-methyl-phenyl]-oxamic acid,
N-{3-chloro-4-[3-(4-fluoro-phenylsulfamoyl)-4-hydroxy-phenoxy]-5-methyl-phenyl}-oxamic acid,
N-[3-chloro-4-(4-hydroxy-3-propylsulfamoyl-phenoxy)-5-methyl-phenyl]-oxamic acid,
N-[4-(3-butylsulfamoyl-4-hydroxy-phenoxy)-3-chloro-5-methyl-phenyl]-oxamic acid,
N-{3-chloro-4-[4-hydroxy-3-(morpholine-4-sulfonyl)-phenoxy]-5-methyl-phenyl}-oxamic acid,
N-{3,5-dichloro-4-[4-hydroxy-3-(pyrrolidine-1-sulfonyl)-phenoxy]-phenyl}-oxamic acid ethyl ester,
N-{3,5-dichloro-4-[3-(3,4-dihydro-1H-isoquinoline-2-sulfonyl)-4-hydroxy-phenoxy]-phenyl}-oxamic acid ethyl ester,
N-[3,5-dichloro-4-(3-cyclobutylsulfamoyl-4-hydroxy-phenoxy)-phenyl]-oxamic acid ethyl ester,
N-{4-[3-(bicyclo[2.2.1]hept-2-ylsulfamoyl)-4-hydroxy-phenoxy]-3,5-dichloro-phenyl}-oxamic acid ethyl ester,
N-(3,5-dichloro-4-{4-hydroxy-3-[(thiophen-2-ylmethyl)-sulfamoyl]-phenoxy}-phenyl)-oxamic acid ethyl ester,
N-[3,5-dichloro-4-(4-hydroxy-3-isopropylsulfamoyl-phenoxy)-phenyl]-oxamic acid ethyl ester,
N-[3,5-dichloro-4-(3-dimethylsulfamoyl-4-hydroxy-phenoxy)-phenyl]-oxamic acid ethyl ester,
N-{3,5-dichloro-4-[4-hydroxy-3-(pyrrolidine-1-sulfonyl)-phenoxy]-phenyl}-oxamic acid and
N-[3,5-dichloro-4-(4-hydroxy-3-isopropylsulfamoyl-phenoxy)-phenyl]-oxamic acid.

89. A compound as defined in claim 1 selected from the group consisting of
N-{3,5-dichloro-4-[3-(3,3-dimethyl-piperidine-1-carbonyl)-4-hydroxy-phenoxy]-phenyl}-oxamic acid ethyl ester,
N-{4-[3-(3,4-dihydro-1H-isoquinoline-2-carbonyl)-4-hydroxy-phenoxy]-3,5-dimethyl-phenyl}-oxamic acid ethyl ester,
N-{4-[3-(3,4-dihydro-2H-quinoline-1-carbonyl)-4-hydroxy-phenoxy]-3,5-dimethyl-phenyl}-oxamic acid ethyl ester,
N-{4-[3-(2,3-dihydro-indole-1-carbonyl)-4-hydroxy-phenoxy]-3,5-dimethyl-phenyl}-oxamic acid ethyl ester,
N-{4-[3-(3,3-dimethyl-piperidine-1-carbonyl)-4-hydroxy-phenoxy]-3,5-dimethyl-phenyl}-oxamic acid ethyl ester,
N-{4-[4-hydroxy-3-(3-methyl-3-phenyl-piperidine-1-carbonyl)-phenoxy]-3,5-dimethyl-phenyl}-oxamic acid ethyl ester,
N-{4-[3-(azepane-1-carbonyl)-4-hydroxy-phenoxy]-3,5-dimethyl-phenyl}-oxamic acid ethyl ester,
N-{4-[4-hydroxy-3-(1-naphthalen-1-yl-(1R)-ethylcarbamoyl)-phenoxy]-3,5-dimethyl-phenyl}-oxamic acid ethyl ester,
N-{4-[4-hydroxy-3-(1-phenyl-(1R)-ethylcarbamoyl)-phenoxy]-3,5-dimethyl-phenyl}-oxamic acid ethyl ester,
N-{4-[3-(bicyclo[2.2.1]hept-2-ylcarbamoyl)-4-hydroxy-phenoxy]-3,5-dimethyl-phenyl}-oxamic acid ethyl ester,
N-{4-[3-(4-chloro-benzylcarbamoyl)-4-hydroxy-phenoxy]-3,5-dimethyl-phenyl}-oxamic acid ethyl ester,
N-{4-[3-(1-cyclohexyl-(1R)-ethylcarbamoyl)-4-hydroxy-phenoxy]-3,5-dimethyl-phenyl}-oxamic acid ethyl ester,
N-{4-[4-hydroxy-3-(1-naphthalen-2-yl-(1R)-ethylcarbamoyl)-phenoxy]-3,5-dimethyl-phenyl}-oxamic acid ethyl ester,
N-[4-(3-cyclobutylcarbamoyl-4-hydroxy-phenoxy)-3,5-dimethyl-phenyl]-oxamic acid ethyl ester,
N-[4-(3-cyclopentylcarbamoyl-4-hydroxy-phenoxy)-3,5-dimethyl-phenyl]-oxamic acid ethyl ester,
N-{4-[4-hydroxy-3-(1-isopropyl-2-methyl-propylcarbamoyl)-phenoxy]-3,5-dimethyl-phenyl}-oxamic acid ethyl ester,
N-{4-[4-hydroxy-3-(pyrrolidine-1-carbonyl)-phenoxy]-3,5-dimethyl-phenyl}-oxamic acid ethyl ester,
N-{4-[4-hydroxy-3-(morpholine-4-carbonyl)-phenoxy]-3,5-dimethyl-phenyl}-oxamic acid ethyl ester, N-{4-[4-hydroxy-3-(1-naphthalen-1-yl-(1R)ethylcarbamoyl)-phenoxy]-3,5-dimethyl-phenyl}-oxamic acid,
N-{4-[4-hydroxy-3-(1-phenyl-(1R)ethylcarbamoyl)-phenoxy]-3,5-dimethyl-phenyl}-oxamic acid,
N-{4-[3-(cyclopropyl-methyl-carbamoyl)-4-hydroxy-phenoxy]-3,5-dimethyl-pentyl}-oxamic acid,
N-{4-[3-(cyclobutyl-methyl-carbamoyl)-4-hydroxy-phenoxy]-3,5-dimethyl-phenyl}-oxamic acid,
N-{4-[4-hydroxy-3-(1-isopropyl-2-methyl-propylcarbamoyl)-phenoxy]-3,5-dimethyl-phenyl}-oxamic acid,
N-{4-[3-(cyclopentyl-methyl-carbamoyl)-4-hydroxy-phenoxy]-3,5-dimethyl-phenyl}-oxamic acid,
N-{4-[3-(cyclohexyl-methyl-carbamoyl)-4-hydroxy-phenoxy]-3,5-dimethyl-phenyl}-oxamic acid,
N-{3-chloro-4-[4-hydroxy-3-(3-methyl-3-phenyl-piperidine-1-carbonyl)-phenoxy]-5-methyl-phenyl}-oxamic acid ethyl ester,
N-{4-[3-(azepane-1-carbonyl)-4-hydroxy-phenoxy]-3-chloro-5-methyl-phenyl}-oxamic acid ethyl ester,
N-{3-chloro-4-[3-(3,3-dimethyl-piperidine-1-carbonyl)-4-hydroxy-phenoxy]-5-methyl-phenyl}-oxamic acid ethyl ester,
N-(3-chloro-4-{4-hydroxy-3-[(thiophen-2-ylmethyl)-carbamoyl]-phenoxy}-5-methyl-phenyl)-oxamic acid ethyl ester,
N-{3-chloro-4-[3-(2,3-dichloro-benzylcarbamoyl)-4-hydroxy-phenoxy]-5-methyl-phenyl}-oxamic acid ethyl ester,
N-[3-chloro-4-(3-cyclopropylcarbamoyl-4-hydroxy-phenoxy)-5-methyl-phenyl]-oxamic acid ethyl ester,
N-{3-chloro-4-[3-(2,3-dihydro-indole-1-carbonyl)-4-hydroxy-phenoxy]-methyl-phenyl}-oxamic acid ethyl ester,
N-{3-chloro-4-[3-(3,4-dihydro-2H-quinoline-1-carbonyl)-4-hydroxy-phenoxy]-5-methyl-phenyl}-oxamic acid ethyl ester,
N-{3-chloro-4-[3-(3,4-dihydro-1H-isoquinoline-2-carbonyl)-4-hydroxy-phenoxy]-5-methyl-phenyl}-oxamic acid ethyl ester,
N-{3-chloro-4-[4-hydroxy-3-(indan-1-ylcarbamoyl)-phenoxy]-5-methyl-phenyl}-oxamic acid ethyl ester,
N-{3-chloro-4-[4-hydroxy-3-(indan-5-ylcarbamoyl)-phenoxy]-5-methyl-phenyl}-oxamic acid ethyl ester,
N-{4-[3-(bicyclo[2.2.1]hept-2-ylcarbamoyl)-4-hydroxy-phenoxy]-3-chloro-5-methyl-phenyl}-oxamic acid ethyl ester,
N-{3-chloro-4-[3-(cyclohexylmethyl-carbamoyl)-4-hydroxy-phenoxy]-5-methyl-phenyl}-oxamic acid ethyl ester,
N-{3-chloro-4-[3-(1-cyclohexyl-(1R)ethylcarbamoyl)-4-hydroxy-phenoxy]-5-methyl-phenyl}-oxamic acid ethyl ester,
N-{3-chloro-4-[3-(1-cyclohexyl-(1S)ethylcarbamoyl)-4-hydroxy-phenoxy]-5-methyl-phenyl}-oxamic acid ethyl ester,
N-{3-chloro-4-[4-hydroxy-3-(piperidine-1-carbonyl)-phenoxy]-5-methyl-phenyl}-oxamic acid ethyl ester,
N-{4-[3-(azocane-1-carbonyl)-4-hydroxy-phenoxy]-3-chloro-5-methyl-phenyl}-oxamic acid ethyl ester,
N-[3-chloro-4-(3-cyclohexylcarbamoyl-4-hydroxy-phenoxy)-5-methyl-phenyl]-oxamic acid ethyl ester,
N-{3-chloro-4-[4-hydroxy-3-(1-phenyl-(1R)ethylcarbamoyl)-phenoxy]-5-methyl-phenyl}-oxamic acid ethyl ester,
N-[3-chloro-4-(4-hydroxy-3-propylcarbamoyl-phenoxy)-5-methyl-phenyl]-oxamic acid ethyl ester,
N-[4-(3-butylcarbamoyl-4-hydroxy-phenoxy)-3-chloro-5-methyl-phenyl]-oxamic acid ethyl ester,
N-[3-chloro-4-(4-hydroxy-3-pentylcarbamoyl-phenoxy)-5-methyl-phenyl]-oxamic acid ethyl ester,
N-[3-chloro-4-(3-hexylcarbamoyl-4-hydroxy-phenoxy)-5-methyl-phenyl]-oxamic acid ethyl ester,
N-{3-chloro-4-[3-(1,1-dimethyl-propylcarbamoyl)-4-hydroxy-phenoxy]-5-methyl-phenyl}-oxamic acid ethyl ester,
N-[3-chloro-4-(3-diisopropylcarbamoyl-4-hydroxy-phenoxy)-5-methyl-phenyl]-oxamic acid ethyl ester,
N-{3-chloro-4-[3-(2,2-dimethyl-propylcarbamoyl)-4-hydroxy-phenoxy]-5-methyl-phenyl}-oxamic acid ethyl ester,
N-{3-chloro-4-[3-(1,2-dimethyl-propylcarbamoyl)-4-hydroxy-phenoxy]-5-methyl-phenyl}-oxamic acid ethyl ester,
N-{3-chloro-4-[4-hydroxy-3-(1-phenyl-(1S)ethylcarbamoyl)-phenoxy]-5-methyl-phenyl}-oxamic acid ethyl ester,
N-{3-chloro-4-[3-(ethyl-methyl-carbamoyl)-4-hydroxy-phenoxy]-5-methyl-phenyl}-oxamic acid ethyl ester,
N-{3-chloro-4-[4-hydroxy-3-(methyl-propyl-carbamoyl)-phenoxy]-5-methyl-phenyl}-oxamic acid ethyl ester,
N-{3-chloro-4-[3-(ethyl-isopropyl-carbamoyl)-4-hydroxy-phenoxy]-5-methyl-phenyl}-oxamic acid ethyl ester,
N-{3-chloro-4-[3-(cyclobutyl-methyl-carbamoyl)-4-hydroxy-phenoxy]-5-methyl-phenyl}-oxamic acid ethyl ester,
N-{4-[3-(azepane-1-carbonyl)-4-hydroxy-phenoxy]-3-chloro-5-methyl-phenyl}-oxamic acid,
N-{3-chloro-4-[3-(1-cyclohexyl-(1S)ethylcarbamoyl)-4-hydroxy-phenoxy]-5-methyl-phenyl}-oxamic acid,
N-{3-chloro-4-[3-(cyclobutyl-methyl-carbamoyl)-4-hydroxy-phenoxy]-5-methyl-phenyl}-oxamic acid,
N-{4-[3-(bicyclo[2.2.1]hept-2-ylcarbamoyl)-4-hydroxy-phenoxy]-3,5-dichloro-phenyl}-oxamic acid ethyl ester,
N-{4-[3-(bicyclo[2.2.1]hept-2-ylcarbamoyl)-4-hydroxy-phenoxy]-3,5-dichloro-phenyl}-oxamic acid ethyl ester,
N-(3,5-dichloro-4-{4-hydroxy-3-[(thiophen-2-ylmethyl)-carbamoyl]-phenoxy}-phenyl)-oxamic acid ethyl ester,
N-{3,5-dichloro-4-[3-(2-chloro-benzylcarbamoyl)-4-hydroxy-phenoxy]-phenyl}-oxamic acid ethyl ester,
N-{3,5-dichloro-4-[4-hydroxy-3-(3-methyl-3-phenyl-piperidine-1-carbonyl)-phenoxy]-phenyl}-oxamic acid ethyl ester,
N-{3,5-dichloro-4-[3-(3,4-dihydro-1H-isoquinoline-2-carbonyl)-4-hydroxy-phenoxy]-phenyl}-oxamic acid ethyl ester,
N-{3,5-dichloro-4-[4-hydroxy-3-(indan-1-ylcarbamoyl)-phenoxy]-phenyl}-oxamic acid ethyl ester,
N-(4-{3-[(benzo[1,3]dioxol-5-ylmethyl)-carbamoyl]-4-hydroxy-phenoxy}-3,5-dichloro-phenyl)-oxamic acid ethyl ester,
N-{4-[3-(azepane-1-carbonyl)-4-hydroxy-phenoxy]-3,5-dichloro-phenyl}-oxamic acid ethyl ester,
N-{3,5-dichloro-4-[4-hydroxy-3-(4-methyl-piperidine-1-carbonyl)-phenoxy]-phenyl}-oxamic acid ethyl ester,
N-{3,5-dichloro-4-[3-(4-fluoro-phenylcarbamoyl)-4-hydroxy-phenoxy]-phenyl}-oxamic acid ethyl ester,
N-{3,5-dichloro-4-[3-(cyclohexylmethyl-carbamoyl)-4-hydroxy-phenoxy]-phenyl}-oxamic acid ethyl ester,
N-{3,5-dichloro-4-[3-(1-cyclohexyl-(1R)ethylcarbamoyl)-4-hydroxy-phenoxy]-phenyl}-oxamic acid ethyl ester,
N-{3,5-dichloro-4-[3-(1-cyclohexyl-(1S)ethylcarbamoyl)-4-hydroxy-phenoxy]-phenyl}-oxamic acid ethyl ester,
N-{3,5-dichloro-4-[4-hydroxy-3-(piperidine-1-carbonyl)-phenoxy]-phenyl}-oxamic acid ethyl ester, N-{3,5-dichloro-4-[4-hydroxy-3-(3-methyl-piperidine-1-carbonyl)-phenoxy]-phenyl}-oxamic acid ethyl ester,
N-{4-[3-(biphenyl-3-ylcarbamoyl)-4-hydroxy-phenoxy]-3,5-dichloro-phenyl}-oxamic acid ethyl ester,
N-[3,5-dichloro-4-(3-cyclopropylcarbamoyl-4-hydroxy-phenoxy)-phenyl]-oxamic acid ethyl ester,
N-{3,5-dichloro-4-[3-(2,3-dichloro-benzylcarbamoyl)-4-hydroxy-phenoxy]-phenyl}-oxamic acid ethyl ester,
N-[3,5-dichloro-4-(3-cyclobutylcarbamoyl-4-hydroxy-phenoxy)-phenyl]-oxamic acid ethyl ester,
N-[3,5-dichloro-4-(3-cyclopentylcarbamoyl-4-hydroxy-phenoxy)-phenyl]-oxamic acid ethyl ester,
N-(3,5-dichloro-4-{4-hydroxy-3-[(naphthalen-1-ylmethyl)-carbamoyl]-phenoxy}-phenyl)-oxamic acid ethyl ester,
N-{3,5-dichloro-4-[3-(4-fluoro-benzylcarbamoyl)-4-hydroxy-phenoxy]-phenyl}-oxamic acid ethyl ester,
N-{4-[3-(azocane-1-carbonyl)-4-hydroxy-phenoxy]-3,5-dichloro-phenyl}-oxamic acid ethyl ester,
N-{3,5-dichloro-4-[4-hydroxy-3-(1,2,3,4-tetrahydro-naphthalen-1-ylcarbamoyl)-phenoxy]-phenyl}-oxamic acid ethyl ester,
N-{3,5-dichloro-4-[4-hydroxy-3-(1-isopropyl-2-methyl-propylcarbamoyl)-phenoxy]-phenyl}-oxamic acid ethyl ester,
N-{3,5-dichloro-4-[4-hydroxy-3-(6-methoxy-3,4-dihydro-2H-quinoline-1-carbonyl)-phenoxy]-phenyl}-oxamic acid ethyl ester,
N-{3,5-dichloro-4-[4-hydroxy-3-(6-methyl-3,4-dihydro-2H-quinoline-1-carbonyl)-phenoxy]-phenyl}-oxamic acid ethyl ester,
N-{3,5-dichloro-4-[4-hydroxy-3-(4-isopropyl-benzylcarbamoyl)-phenoxy]-phenyl}-oxamic acid ethyl ester,
N-{3,5-dichloro-4-[3-(4-chloro-benzylcarbamoyl)-4-hydroxy-phenoxy]-phenyl}-oxamic acid ethyl ester,
N-{3,5-dichloro-4-[4-hydroxy-3-((1R)indan-1-ylcarbamoyl)-phenoxy]-phenyl}-oxamic acid ethyl ester,
N-{3,5-dichloro-4-[4-hydroxy-3-((1S)indan-1-ylcarbamoyl)-phenoxy]-phenyl}-oxamic acid ethyl ester,
N-{3,5-dichloro-4-[4-hydroxy-3-(1-phenyl-(1R)ethylcarbamoyl)-phenoxy]-phenyl}-oxamic acid ethyl ester,
N-{3,5-dichloro-4-[4-hydroxy-3-(1-naphthalen-1-yl-(1S)ethylcarbamoyl)-phenoxy]-phenyl}-oxamic acid ethyl ester,
N-{3,5-dichloro-4-[3-(3,4-difluoro-benzylcarbamoyl)-4-hydroxy-phenoxy]-phenyl}-oxamic acid ethyl ester,
N-{3,5-dichloro-4-[3-(3-chloro-4-fluoro-benzylcarbamoyl)-4-hydroxy-phenoxy]-phenyl}-oxamic acid ethyl ester,
N-{3,5-dichloro-4-[3-(2-chloro-4-fluoro-benzylcarbamoyl)-4-hydroxy-phenoxy]-phenyl}-oxamic acid ethyl ester,
N-{3,5-dichloro-4-[4-hydroxy-3-(1-naphthalen-2-yl-(1R)ethylcarbamoyl)-phenoxy]-phenyl}-oxamic acid ethyl ester,
N-{3,5-dichloro-4-[3-(2,4-dichloro-benzylcarbamoyl)-4-hydroxy-phenoxy]-phenyl}-oxamic acid ethyl ester,
N-{3,5-dichloro-4-[3-(3,4-dichloro-benzylcarbamoyl)-4-hydroxy-phenoxy]-phenyl}-oxamic acid ethyl ester,
N-{3,5-dichloro-4-[3-(4-chloro-3-trifluoromethyl-benzylcarbamoyl)-4-hydroxy-phenoxy]-phenyl}-oxamic acid ethyl ester,
N-{3,5-dichloro-4-[3-(4-chloro-2-fluoro-benzylcarbamoyl)-4-hydroxy-phenoxy]-phenyl}-oxamic acid ethyl ester,
N-{4-[3-(4-tert-butyl-benzylcarbamoyl)-4-hydroxy-phenoxy]-3,5-dichloro-phenyl}-oxamic acid ethyl ester,
N-[3,5-dichloro-4-(3-cyclohexylcarbamoyl-4-hydroxy-phenoxy)-phenyl]-oxamic acid ethyl ester,
N-[3,5-dichloro-4-(4-hydroxy-3-isopropylcarbamoyl-phenoxy)-phenyl]-oxamic acid ethyl ester,
N-{3,5-dichloro-4-[4-hydroxy-3-(isopropyl-methyl-carbamoyl)-phenoxy]-phenyl}-oxamic acid ethyl ester,
N-{3,5-dichloro-4-[3-(cyclopropylmethyl-carbamoyl)-4-hydroxy-phenoxy]-phenyl}-oxamic acid ethyl ester,
N-{3,5-dichloro-4-[3-(4-fluoro-benzylcarbamoyl)-4-hydroxy-phenoxy]-phenyl}-oxamic acid,
N-[3,5-dichloro-4-(3-dimethylcarbamoyl-4-hydroxy-phenoxy)-phenyl]-oxamic acid and
N-{3,5-dichloro-4-[4-hydroxy-3-(1-isopropyl-2-methyl-propylamino-carbonyl)-phenoxy]-phenyl}-oxamic acid.

90. A compound as defined in claim 1 selected from the group consisting of
N-{3,5-dichloro-4-[4-hydroxy-3-(indan-1-ylaminomethyl)-phenoxy]-phenyl}-oxamic acid ethyl ester,
N-{4-[3-(2,3-dihydro-indol-1-ylmethyl)-4-hydroxy-phenoxy]-3,5-dimethyl-phenyl}-oxamic acid ethyl ester,
N-{4-[3-(3,3-dimethyl-piperidin-1-ylmethyl)-4-hydroxy-phenoxy]-3,5-dimethyl-phenyl}-oxamic acid ethyl ester,
N-{4-[4-hydroxy-3-(3-methyl-3-phenyl-piperidin-1-ylmethyl)-phenoxy]-3,5-dimethyl-phenyl}-oxamic acid ethyl ester,
N-{4-[3-(3,4-dihydro-1H-isoquinolin-2-ylmethyl)-4-hydroxy-phenoxy]-3,5-dimethyl-phenyl}-oxamic acid ethyl ester,
N-(4-{3-[(4-fluoro-benzylamino)-methyl]-4-hydroxy-phenoxy}-3,5-dimethyl-phenyl)-oxamic acid ethyl ester,
N-(4-{3-[(4-chloro-benzylamino)-methyl]-4-hydroxy-phenoxy}-3,5-dimethyl-phenyl)-oxamic acid ethyl ester,
N-(4-{4-hydroxy-3-[(4-isopropyl-benzylamino)-methyl]-phenoxy}-3,5-dimethyl-phenyl)-oxamic acid ethyl ester,
N-[4-(3-azepan-1-ylmethyl-4-hydroxy-phenoxy)-3,5-dimethyl-phenyl]-oxamic acid ethyl ester,
N-[4-(3-{[(benzo[1,3]dioxol-5-ylmethyl)-amino]-methyl}-4-hydroxy-phenoxy)-3,5-dimethyl-phenyl]-oxamic acid ethyl ester,
N-(4-{4-hydroxy-3-[(1,2,3,4-tetrahydro-naphthalen-1-ylamino)-methyl]-phenoxy}-3,5-dimethyl-phenyl)-oxamic acid ethyl ester,
N-[4-(3-dimethylaminomethyl-4-hydroxy-phenoxy)-3,5-dimethyl-phenyl]-oxamic acid ethyl ester,
N-(4-{4-hydroxy-3-[(methyl-propyl-amino)-methyl]-phenoxy}-3,5-dimethyl-phenyl)-oxamic acid ethyl ester,
N-[4-(3-cyclopropylaminomethyl-4-hydroxy-phenoxy)-3,5-dimethyl-phenyl]-oxamic acid ethyl ester,
N-[4-(4-hydroxy-3-morpholin-4-ylmethyl-phenoxy)-3,5-dimethyl-phenyl]-oxamic acid ethyl ester,
N-(4-{4-hydroxy-3-[(isopropyl-methyl-amino)-methyl]-phenoxy}-3,5-dimethyl-phenyl)-oxamic acid ethyl ester,
N-{4-[4-hydroxy-3-(isopropylamino-methyl)-phenoxy]-3,5-dimethyl-phenyl}-oxamic acid ethyl ester,
N-[4-(3-cyclobutylaminomethyl-4-hydroxy-phenoxy)-3,5-dimethyl-phenyl]-oxamic acid ethyl ester,
N-[4-(3-cyclopentylaminomethyl-4-hydroxy-phenoxy)-3,5-dimethyl-phenyl]-oxamic acid ethyl ester,
N-{3-chloro-4-[3-(3,3-dimethyl-piperidin-1-ylmethyl)-4-hydroxy-phenoxy]-5-methyl-phenyl}-oxamic acid methyl ester,
N-{3-chloro-4-[3-(2,3-dihydro-indol-1-ylmethyl)-4-hydroxy-phenoxy]-5-methyl-phenyl}-oxamic acid methyl ester,
N-(3-chloro-4-{3-[(4-fluoro-benzylamino)-methyl]-4-hydroxy-phenoxy}-5-methyl-phenyl)-oxamic acid ethyl ester,
N-{3-chloro-4-[4-hydroxy-3-(3-methyl-3-phenyl-piperidin-1-ylmethyl)-phenoxy]-5-methyl-phenyl}-oxamic acid ethyl ester, N-(3-chloro-4-{3-[(4-chloro-benzylamino)-methyl]-4-hydroxy-phenoxy}-5-methyl-phenyl)-oxamic acid ethyl ester,
N-(3-chloro-4-{4-hydroxy-3-[(4-isopropyl-benzylamino)-methyl]-phenoxy}-5-methyl-phenyl)-oxamic acid ethyl ester,
N-{3-chloro-4-[3-(3,4-dihydro-1H-isoquinolin-2-ylmethyl)-4-hydroxy-phenoxy]-5-methyl-phenyl}-oxamic acid ethyl ester,
N-[4-(3-azepan-1-ylmethyl-4-hydroxy-phenoxy)-3-chloro-5-methyl-phenyl]-oxamic acid ethyl ester,
N-[4-(3-{[(benzo[1,3]dioxol-5-ylmethyl)-amino]-methyl}-4-hydroxy-phenoxy)-3-chloro-5-methyl-phenyl]-oxamic acid ethyl ester,
N-(3-chloro-4-{4-hydroxy-3-[(1,2,3,4-tetrahydro-naphthalen-1-ylamino)-methyl]-phenoxy}-5-methyl-phenyl)-oxamic acid ethyl ester,
N-[3-chloro-4-(3-dimethylaminomethyl-4-hydroxy-phenoxy)-5-methyl-phenyl]-oxamic acid ethyl ester,
N-(3-chloro-4-{4-hydroxy-3-[(methyl-propyl-amino)-methyl]-phenoxy}-5-methyl-phenyl)-oxamic acid ethyl ester,
N-[3-chloro-4-(3-cyclopropylaminomethyl-4-hydroxy-phenoxy)-5-methyl-phenyl]-oxamic acid ethyl ester,
N-{3,5-dichloro-4-[3-(2,3-dihydro-indol-1-ylmethyl)-4-hydroxy-phenoxy]-phenyl}-oxamic acid methyl ester,
N-{3,5-dichloro-4-[3-(3,3-dimethyl-piperidin-1-ylmethyl)-4-hydroxy-phenoxy]-phenyl}-oxamic acid methyl ester,
N-{3,5-dichloro-4-[4-hydroxy-3-(indan-1-ylaminomethyl)-phenoxy]-phenyl}-oxamic acid methyl ester,
N-{3,5-dichloro-4-[3-(3,4-dihydro-1H-isoquinolin-2-ylmethyl)-4-hydroxy-phenoxy]-phenyl}-oxamic acid methyl ester,
N-[4-(3-azepan-1-ylmethyl-4-hydroxy-phenoxy)-3,5-dichloro-phenyl]-oxamic acid methyl ester,
N-(3,5-dichloro-4-{3-[(1-cyclohexyl-(1R)ethylamino)-methyl]-4-hydroxy-phenoxy}-phenyl)-oxamic acid ethyl ester,
N-{4-[3-(bicyclo[2.2.1]hept-2-ylaminomethyl)-4-hydroxy-phenoxy]-3,5-dichloro-phenyl}-oxamic acid ethyl ester,
N-3,5-dichloro-4-[4-hydroxy-3-(3-methyl-3-phenyl-piperidin-1-ylmethyl)-phenoxy]-phenyl}-oxamic acid ethyl ester,
N-(3,5-dichloro-4-{3-[(4-fluoro-benzylamino)-methyl]-4-hydroxy-phenoxy}-phenyl)-oxamic acid ethyl ester,
N-(3,5-dichloro-4-{4-hydroxy-3-[(1-phenyl-(1R)ethylamino)-methyl]-phenoxy}-phenyl)-oxamic acid ethyl ester,
N-(3,5-dichloro-4-{4-hydroxy-3-[(1-phenyl-(1S)ethylamino)-methyl]-phenoxy}-phenyl)-oxamic acid ethyl ester,
N-[3,5-dichloro-4-(4-hydroxy-3-{[(naphthalen-1-ylmethyl)-amino]-methyl}-phenoxy)-phenyl]-oxamic acid ethyl ester,
N-(3,5-dichloro-4-{4-hydroxy-3-[(1-naphthalen-1-yl-(1R)ethylamino)-methyl]-phenoxy}-phenyl)-oxamic acid ethyl ester,
N-(3,5-dichloro-4-{4-hydroxy-3-[(1,2,3,4-tetrahydro-naphthalen-1-ylamino)-methyl]-phenoxy}-phenyl)-oxamic acid ethyl ester,
N-[3,5-dichloro-4-(3-cyclohexylaminomethyl-4-hydroxy-phenoxy)-phenyl]-oxamic acid ethyl ester,
N-[3,5-dichloro-4-(3-cyclopentylaminomethyl-4-hydroxy-phenoxy)-phenyl]-oxamic acid ethyl ester,
N-[4-(3-{[(benzo[1,3]dioxol-5-ylmethyl)-amino]-methyl}-4-hydroxy-phenoxy)-3,5-dichloro-phenyl]-oxamic acid ethyl ester,
N-(3,5-dichloro-4-{3-[(4-chloro-benzylamino)-methyl]-4-hydroxy-phenoxy}-phenyl)-oxamic acid ethyl ester,
N-(3,5-dichloro-4-{4-hydroxy-3-[(4-isopropyl-benzylamino)-methyl]-phenoxy}-phenyl)-oxamic acid ethyl ester,
N-[3,5-dichloro-4-(4-hydroxy-3-methylaminomethyl-phenoxy)-phenyl]-oxamic acid ethyl ester,
N-[3,5-dichloro-4-(3-cyclopropylaminomethyl-4-hydroxy-phenoxy)-phenyl]-oxamic acid ethyl ester,
N-[3,5-dichloro-4-(4-hydroxy-3-morpholin-4-ylmethyl-phenoxy)-phenyl]-oxamic acid ethyl ester and
N-[3,5-dichloro-4-(3-cyclobutylaminomethyl-4-hydroxy-phenoxy)-phenyl]-oxamic acid ethyl ester.

91. A compound as defined in claim 1 selected from the group consisting of
N-{4-[4-hydroxy-3-(isopropylmethylcarbamoyl)-phenoxy]-3,5-dimethyl-phenyl}-oxamide,
N-{4-[4-hydroxy-3-(1-isopropyl-2-methyl-propylcarbamoyl)-phenoxy]-3,5-dimethyl-phenyl}-oxamide,
N-[3,5-dichloro-4-(3-cyclohexylcarbamoyl-4-hydroxy-phenoxy)-phenyl]-oxamide,
N-{3-chloro-4-[4-hydroxy-3-(morpholine-4-sulfonyl)-phenoxy]-5-methyl-phenyl}-oxamide,
N-[4-(3-benzenesulfonyl-4-hydroxy-phenoxy)-3,5-dichloro-phenyl]-oxamide,
N-{3-chloro-4-[3-(cyclobutylmethylcarbamoyl)-4-hydroxy-phenoxy]-5-methyl-phenyl}-oxamide,
N-{3-chloro-4-[3-(cyclopropylmethyl-amino-sulfonyl)-4-hydroxy-phenoxy]-5-methyl-phenyl}-oxamide,
N-{3-chloro-4-[4-hydroxy-3-(methylpropylsulfamoyl)-phenoxy]-5-methyl-phenyl}-oxamide,
N-{4-[4-hydroxy-3-(pyrrolidine-1-carbonyl)-phenoxy]-3,5-dimethyl-phenyl}-oxamide,
N-[3-chloro-4-(3-cyclopropylsulfamoyl-4-hydroxy-phenoxy)-5-methyl-phenyl]-oxamide and
N-{4-[3-(cyclobutyl-methyl-carbamoyl)-4-hydroxy-phenoxy]-3,5-dimethyl-phenyl}-oxamide.

92. A compound as defined in claim 1 selected from the group consisting of
N-{3,5-dichloro-4-[3-(4-chloro-benzenesulfonyl)-4-hydroxy-phenoxy]-phenyl}-oxamic acid ethyl ester,
N-{3,5-dichloro-4-[3-(4-chloro-benzenesulfonyl)-4-hydroxy-phenoxy]-phenyl}-oxamic acid,
N-{3-chloro-4-[3-(4-chloro-benzenesulfonyl)-4-hydroxy-phenoxy]-5-methyl-phenyl}-oxamic acid,
N-{3-chloro-4-[3-(4-chloro-benzenesulfonyl)-4-hydroxy-phenoxy]-5-methyl-phenyl}-oxamide,
N-[4-(3-benzenesulfonyl-4-hydroxy-phenoxy)-3,5-dichloro-phenyl]-oxamic acid ethyl ester,
N-[4-(3-benzenesulfonyl-4-hydroxy-phenoxy)-3,5-dichloro-phenyl]-oxamic acid,
N-[4-(3-benzenesulfonyl-4-hydroxy-phenoxy)-3,5-dichloro-phenyl]-oxamide,
N-{3,5-dichloro-4-[4-hydroxy-3-(naphthalene-1-sulfonyl)-phenoxy]-phenyl}-oxamic acid ethyl ester,
N-{3,5-dichloro-4-[4-hydroxy-3-(naphthalene-1-sulfonyl)-phenoxy]-phenyl}-oxamic acid,
N-{3,5-dichloro-4-[4-hydroxy-3-(naphthalene-2-sulfonyl)-phenoxy]-phenyl}-oxamic acid ethyl ester,
N-{3,5-dichloro-4-[4-hydroxy-3-(naphthalene-2-sulfonyl)-phenoxy]-phenyl}-oxamic acid,
N-{3,5-dichloro-4-[4-hydroxy-3-(toluene-4-sulfonyl)-phenoxy]-phenyl}-oxamic acid and
N-{3,5-dichloro-4-[4-hydroxy-3-(toluene-4-sulfonyl)-phenoxy]-phenyl}-oxamide.

93. A compound as defined in claim 1 selected from the group consisting of

N-[3,5-dichloro-4-(3-cyclopropylmethanesulfonyl-4-hydroxy-phenoxy)-phenyl]-oxamic acid ethyl ester,
N-[4-(4-hydroxy-3-methanesulfonyl-phenoxy)-3,5-dimethyl-phenyl]-oxamic acid,
N-[3,5-dichloro-4-(3-ethanesulfonyl-4-hydroxy-phenoxy)-phenyl]-oxamic acid,
N-{3,5-dichloro-4-[4-hydroxy-3-(propane-2-sulfonyl)-phenoxy]-phenyl}-oxamic acid ethyl ester,
N-[3,5-dichloro-4-(3-cyclobutylmethanesulfonyl-4-hydroxy-phenoxy)-phenyl]-oxamic acid ethyl ester,
N-[3,5-dichloro-4-(3-cyclohexylmethanesulfonyl-4-hydroxy-phenoxy)-phenyl]-oxamic acid ethyl ester,
N-[3,5-dichloro-4-(3-cyclopentanesulfonyl-4-hydroxy-phenoxy)-phenyl]-oxamic acid ethyl ester,
N-{4-[3-(butane-1-sulfonyl)-4-hydroxy-phenoxy]-3,5-dichloro-phenyl}-oxamic acid,
N-[3,5-dichloro-4-(4-hydroxy-3-phenylmethanesulfonyl-phenoxy)-phenyl]-oxamic acid,
N-{3,5-dichloro-4-[4-hydroxy-3-(propane-1-sulfonyl)-phenoxy]-phenyl}-oxamic acid,
N-{3,5-dichloro-4-[3-(4-fluoro-phenylmethanesulfonyl)-4-hydroxy-phenoxy]-phenyl}-oxamic acid,
N-[3,5-dichloro-4-(3-cyclopropylmethanesulfonyl-4-hydroxy-phenoxy)-phenyl]-oxamic acid,
N-[3,5-dichloro-4-(3-cyclobutylmethanesulfonyl-4-hydroxy-phenoxy)-phenyl]-oxamic acid and
N-[4-(3-cyclopropylmethanesulfonyl-4-hydroxy-phenoxy)-3,5-dimethyl-phenyl]-oxamic acid.

94. A compound as defined in claim 1 selected from the group consisting of
N-[3,5-dichloro-4-(4-hydroxy-3-phenoxy-phenoxy)-phenyl-oxamic acid ethyl ester,
N-{3,5-dichloro-4-[3-(4-chloro-phenoxy)-4-hydroxy-phenoxy]-phenyl}-oxamic acid ethyl ester,
N-{3,5-dichloro-4-[3-(4-chloro-phenoxy)-4-hydroxy-phenoxy]-phenyl}-oxamic acid,
N-[3,5-dichloro-4-(4-hydroxy-3-phenoxy-phenoxy)-phenyl]-oxamic acid,
N-{3,5-dichloro-4-[3-(4-fluoro-phenoxy)-4-hydroxy-phenoxy]-phenyl}-oxamic acid ethyl ester,
N-{3,5-dichloro-4-[3-(4-fluoro-phenoxy)-4-hydroxy-phenoxy]-phenyl}-oxamic acid,
N-{4-[3-(4-fluoro-phenoxy)-4-hydroxy-phenoxy]-3,5-dimethyl-phenyl}-oxamic acid,
N-[4-(4-hydroxy-3-phenoxy-phenoxy)-3,5-dimethyl-phenyl]-oxamic acid and
N-{4-[3-(4-chloro-phenoxy)-4-hydroxy-phenoxy]-3,5-dimethyl-phenyl}-oxamic acid.

95. A compound as defined in claim 1 selected from the group consisting of
N-{3-chloro-4-[3-(4-fluoro-phenoxymethyl)-4-hydroxy-phenoxy]-5-methyl-phenyl}-oxamic acid ethyl ester and
N-[3-chloro-4-(4-hydroxy-3-phenoxymethyl-phenoxy)-5-methyl-phenyl]-oxamic acid ethyl ester.

96. A compound as defined in claim 1 selected from the group consisting of
N-[3,5-dichloro-4-(1H-indol-5-yloxy)-phenyl]-oxamic acid ethyl ester,
N-[3,5-dichloro-4-(1H-indol-5-yloxy)-phenyl]-oxamic acid ethyl ester,
N-[3,5-dichloro-4-(1H-indol-5-yloxy)-phenyl]-oxamic acid,
N-[3,5-dichloro-4-(1H-indol-5-yloxy)-phenyl]-oxamide,
N-[3-chloro-4-(1H-indol-5-yloxy)-5-methyl-phenyl]-oxamic acid,
N-[3-chloro-4-(1H-indol-5-yloxy)-5-methyl-phenyl]-oxamide,
N-[3,5-dichloro-4-(2-methyl-1H-indol-5-yloxy)-phenyl]-oxamic acid ethyl ester and
N-[3,5-dichloro-4-(2-methyl-1H-indol-5-yloxy)-phenyl]-oxamic acid.

97. A compound as defined in claim 1 selected from the group consisting of
N-[3,5-dichloro-4-(4-fluoro-3-methyl-phenoxy)-phenyl]-oxamic acid,
N-[4-(4-fluoro-phenoxy)-3,5-dimethyl-phenyl]-oxamic acid,
N-[3,5-dichloro-4-(4-fluoro-phenoxy)-phenyl]-oxamic acid ethyl ester,
N-[3,5-dichloro-4-(3,4-difluoro-phenoxy)-phenyl]-oxamic acid ethyl ester,
N-[3,5-dichloro-4-(3-chloro-4-fluoro-phenoxy)-phenyl]-oxamic acid ethyl ester,
N-[4-(3,4-difluoro-phenoxy)-3,5-dimethyl-phenyl]-oxamic acid,
N-[4-(3-chloro-4-fluoro-phenoxy)-3,5-dimethyl-phenyl]-oxamic acid,
N-[4-(4-fluoro-3-methyl-phenoxy)-3,5-dimethyl-phenyl]-oxamic acid,
N-[3,5-dichloro-4-(4-fluoro-phenoxy)-phenyl]-oxamic acid,
N-[3,5-dichloro-4-(3,4-difluoro-phenoxy)-phenyl]-oxamic acid,
N-[3,5-dichloro-4-(3-chloro-4-fluoro-phenoxy)-phenyl]-oxalamic acid,
N-{4-[3-(cyclobutyl-methyl-carbamoyl)-4-fluoro-phenoxy]-3,5-dimethyl-phenyl}-oxalamic acid ethyl ester,
N-{4-[3-(cyclobutyl-methyl-carbamoyl)-4-fluoro-phenoxy]-3,5-dimethyl-phenyl}-oxalamic acid and
N-[4-(4-fluoro-phenoxy)-3,5-dimethyl-phenyl]-oxalamic acid ethyl ester.

98. A compound or pharmaceutically acceptable salt as defined in claim 3 wherein $R^5$ is fluoro.

99. A compound or pharmaceutically acceptable salt as defined in claim 98 wherein $R^4$ is hydrogen, fluoro, chloro, methyl or cyclobutyl-methyl-carbamoyl.

100. A compound or pharmaceutically acceptable salt as defined in claim 99 wherein $R^1$ and $R^2$ are each independently methyl or chloro.

101. A compound or pharmaceutically acceptable salt as defined in claim 100 wherein $R^1$ and $R^2$ are each methyl.

102. A compound or pharmaceutically acceptable salt as defined in claim 100 wherein $R^1$ and $R^2$ are each chloro.

103. A compound or pharmaceutically acceptable salt as defined in claim 100 wherein $R^7$ is hydrogen, and $R^8$ is hydrogen or —$OR^9$.

104. A compound or pharmaceutically acceptable salt as defined in claim 103 wherein $R^9$ is methyl or ethyl.

105. A compound as defined in claim 1 selected from the group consisting of:
N-[4-(4-fluoro-phenoxy)-3,5-dimethyl-phenyl]-oxamic acid,
N-[3,5-dichloro-4-(4-fluoro-phenoxy)-phenyl]-oxamic acid,
N-[3,5-dichloro-4-(3,4-difluoro-phenoxy)-phenyl]-oxamic acid,
N-[4-(3-methyl-4-Fluoro-phenoxy)-3,5-dichloro-phenyl]-oxamic acid,
N-[3,5-dichloro-4-(3-chloro-4-fluoro-phenoxy)-phenyl]-oxamic acid,
N-[4-(3,4-difluoro-phenoxy)-3,5-dimethyl-phenyl]-oxamic acid,
N-[4-(3-chloro-4-fluoro-phenoxy)-3,5-dimethyl-phenyl]-oxamic acid,
N-[4-(3-methyl-4-fluoro-phenoxy)-3,5-dimethyl-phenyl]-oxamic acid,
N-[3,5-dichloro-4-(4-fluoro-phenoxy)-phenyl]-oxamic acid, N-[3,5-dichloro-4-(3,4-difluoro-phenoxy)-phenyl]-oxamic acid,
N-{4-[3-(cyclobutyl-methyl-carbamoyl)-4-fluoro-phenoxy)-3,5-dimethyl-phenyl]-oxamic acid and
N-[4-(4-fluoro-phenoxy)-3,5-dimethyl-phenyl]-oxamic acid.

106. A pharmaceutically acceptable salt of each of said compounds as defined in claim 105 where said salt is independently a potassium salt or a sodium salt.

107. An ester of each of said compounds as defined in claim 105 where said ester is independently a methyl ester, an ethyl ester or an isopropyl ester.

108. A method of treating a condition selected from the group consisting of obesity, hyperlipidemia, glaucoma, cardiac arrhythmia, skin disorders, thyroid disease, hypothyroidism, diabetes mellitus, atherosclerosis, hypertension, coronary heart disease, hypercholesteremia, depression and osteoporosis, in a mammal which comprises administering to said mammal an effective treating amount of a compound, prodrug, isomer or pharmaceutically acceptable salt as defined in claim 1.

109. A method as defined in claim 108 further including administering an anorectic agent.

110. A method as defined in claim 108 further including administering a lipase inhibitor.

111. A method as defined in claim 109 further including administering a lipase inhibitor.

112. A method as defined in claim 108 wherein said condition is obesity.

113. A method as defined in claim 109 wherein said condition is obesity.

114. A method as defined in claim 110 wherein said condition is obesity.

115. A method as defined in claim 111 wherein said condition is obesity.

116. A pharmaceutical composition comprising a compound, prodrug, isomer or pharmaceutically acceptable salt as defined in claim 1, and a pharmaceutically acceptable vehicle, diluent or carrier.

117. A pharmaceutical composition as defined in claim 116 further including an anorectic agent.

118. A pharmaceutical composition as defined in claim 116 further including a lipase inhibitor.

119. A pharmaceutical composition as defined in claim 117 further including a lipase inhibitor.

120. A pharmaceutical composition for treating a condition selected from the group consisting of obesity, hyperlipidemia, glaucoma, cardiac arrhythmia, skin disorders, thyroid disease, hypothyroidism, diabetes mellitus, atherosclerosis, hypertension, coronary heart disease, hypercholesteremia, depression and osteoporosis, in a mammal comprising a compound, prodrug, isomer or pharmaceutically acceptable salt as defined in claim 1, and a pharmaceutically acceptable vehicle, diluent or carrier.

121. A pharmaceutical composition as defined in claim 120 further including an anorectic agent.

122. A pharmaceutical composition as defined in claim 120 further including a lipase inhibitor.

123. A pharmaceutical composition as defined in claim 121 further including a lipase inhibitor.

124. A pharmaceutical composition as defined in claim 120 wherein said condition is obesity.

125. A pharmaceutical composition as defined in claim 121 wherein said condition is obesity.

126. A pharmaceutical composition as defined in claim 122 wherein said condition is obesity.

127. A pharmaceutical composition as defined in claim 123 wherein said condition is obesity.

128. A kit for the treatment of a condition selected from the group consisting of obesity, hyperlipidemia, glaucoma, cardiac arrhythmia, skin disorders, thyroid disease, hypothyroidism, diabetes mellitus, atherosclerosis, hypertension, coronary heart disease, hypercholesteremia, depression and osteoporosis which comprises: a first compound, said first compound being a compound, prodrug, isomer, or pharmaceutically acceptable salt as defined in claim 1, and a pharmaceutically acceptable vehicle, carrier or diluent, in a first unit dosage form; a second compound, said second compound being an anorectic agent or a lipase inhibitor, and a pharmaceutically acceptable vehicle, carrier or diluent, in a second unit dosage form; and a container.

129. A kit as defined in claim 128 wherein said condition is obesity.

* * * * *